(12) United States Patent
Zhou et al.

(10) Patent No.: US 9,927,430 B2
(45) Date of Patent: Mar. 27, 2018

(54) PRO-SUBSTRATES FOR LIVE CELL APPLICATIONS

(71) Applicant: PROMEGA CORPORATION, Madison, WI (US)

(72) Inventors: Wenhui Zhou, San Luis Obispo, CA (US); Brock Binkowski, Sauk City, WI (US); Hui Wang, San Luis Obispo, CA (US); Braeden Butler, Madison, WI (US); Thomas Machleidt, Madison, WI (US); Keith Wood, Madison, WI (US)

(73) Assignee: PROMEGA CORPORATION, Madison, WI (US)

( * ) Notice: Subject to any disclaimer, the term of this patent is extended or adjusted under 35 U.S.C. 154(b) by 36 days.

(21) Appl. No.: 14/608,910

(22) Filed: Jan. 29, 2015

(65) Prior Publication Data

US 2015/0212078 A1  Jul. 30, 2015

Related U.S. Application Data

(60) Provisional application No. 61/933,210, filed on Jan. 29, 2014.

(51) Int. Cl.

| | |
|---|---|
| *C12Q 1/66* | (2006.01) |
| *G01N 33/68* | (2006.01) |
| *G01N 33/542* | (2006.01) |
| *C07D 487/04* | (2006.01) |
| *C07K 5/093* | (2006.01) |
| *C07K 5/113* | (2006.01) |
| *C07K 5/072* | (2006.01) |

(52) U.S. Cl.
CPC ......... *G01N 33/542* (2013.01); *C07D 487/04* (2013.01); *C07K 5/06113* (2013.01); *C07K 5/0819* (2013.01); *C07K 5/1021* (2013.01); *C12Q 1/66* (2013.01); *G01N 33/6845* (2013.01)

(58) Field of Classification Search
CPC ............. G01N 33/542; G01N 33/6845; C07D 487/04; C07K 5/0819; C07K 5/06113; C12Q 1/66

See application file for complete search history.

(56) References Cited

U.S. PATENT DOCUMENTS

| | | |
|---|---|---|
| 5,670,356 A | 9/1997 | Sherf et al. |
| 5,683,888 A | 11/1997 | Campbell |
| 5,837,465 A | 11/1998 | Squirrell et al. |

(Continued)

FOREIGN PATENT DOCUMENTS

| | | |
|---|---|---|
| CN | 1705680 | 12/2005 |
| CN | 101287842 | 10/2008 |

(Continued)

OTHER PUBLICATIONS

Angelucci, F. et al., "Schistosoma mansoni fatty acid binding protein: specificity and functional control as revealed by crystallographic structure," Biochem. (2004) 43:13000-13011.

(Continued)

*Primary Examiner* — Tracy Vivlemore
*Assistant Examiner* — Nam P Nguyen
(74) *Attorney, Agent, or Firm* — Michael Best & Friedrich LLP

(57) ABSTRACT

Provided are pro-substrates useful in assays of living cells. The pro-substrates can be used to detect the presence or absence of enzymes, such as luciferase, in living cells. The pro-substrates can be coelenterazine derivatives or analogs.

15 Claims, 16 Drawing Sheets

(56) References Cited

U.S. PATENT DOCUMENTS

| | | |
|---|---|---|
| 5,998,204 A | 12/1999 | Tsien et al. |
| 6,132,983 A | 10/2000 | Lowe et al. |
| 6,171,808 B1 | 1/2001 | Squirrell et al. |
| 6,265,177 B1 | 7/2001 | Squirrell et al. |
| 6,387,675 B1 | 5/2002 | Wood et al. |
| 6,544,754 B2 | 4/2003 | Inoye |
| 6,552,179 B1 | 4/2003 | Wood et al. |
| 6,602,677 B1 | 8/2003 | Wood et al. |
| 7,078,181 B2 | 7/2006 | Hawkins et al. |
| 7,108,996 B2 | 9/2006 | Hawkins et al. |
| 7,118,878 B1 | 10/2006 | Hawkins |
| 7,125,697 B2 | 10/2006 | Inouye |
| 7,238,842 B2 | 7/2007 | Wood et al. |
| 7,241,584 B2 | 7/2007 | Wood et al. |
| 7,268,229 B2 | 9/2007 | Wood et al. |
| 7,416,854 B2 | 8/2008 | Riss et al. |
| 7,425,436 B2 | 9/2008 | Darzins et al. |
| 7,429,472 B2 | 9/2008 | Darzins et al. |
| 7,537,912 B2 | 5/2009 | Wood et al. |
| 7,553,632 B2 | 6/2009 | Niles et al. |
| 7,692,002 B2 | 4/2010 | Alberto et al. |
| 7,692,022 B2 | 4/2010 | Cali et al. |
| 7,728,118 B2 | 6/2010 | Wood et al. |
| 7,741,067 B2 | 6/2010 | Hawkins et al. |
| 7,807,402 B2 | 10/2010 | Horn et al. |
| 7,867,726 B2 | 1/2011 | Wood et al. |
| 7,879,540 B1 | 2/2011 | Wood et al. |
| 7,888,086 B2 | 2/2011 | Darzins et al. |
| 7,906,282 B2 | 3/2011 | Wood et al. |
| 7,906,298 B1 | 3/2011 | Squirrell et al. |
| 7,935,803 B2 | 5/2011 | Darzins et al. |
| 7,951,550 B2 | 5/2011 | Cali et al. |
| 8,008,006 B2 | 8/2011 | Wood et al. |
| 8,030,017 B2 | 10/2011 | Wood et al. |
| RE42,931 E | 11/2011 | Wood et al. |
| 8,106,052 B2 | 1/2012 | Wood et al. |
| 8,168,405 B2 | 5/2012 | Darzins et al. |
| 8,183,007 B2 | 5/2012 | Zegzouti et al. |
| 8,183,036 B2 | 5/2012 | Fan et al. |
| 8,202,700 B2 | 6/2012 | Darzins et al. |
| 8,557,970 B2 | 10/2013 | Encell et al. |
| 8,809,529 B2 | 8/2014 | Klaubert et al. |
| 2003/0068801 A1 | 4/2003 | Wood et al. |
| 2003/0153090 A1 | 8/2003 | Wood et al. |
| 2003/0166905 A1 | 9/2003 | Wood et al. |
| 2003/0232404 A1 | 12/2003 | Wood et al. |
| 2004/0002127 A1 | 1/2004 | Inoue et al. |
| 2004/0096924 A1 | 5/2004 | Hawkins et al. |
| 2004/0096927 A1 | 5/2004 | Chittock et al. |
| 2004/0171099 A1 | 9/2004 | Cali et al. |
| 2004/0178545 A1 | 9/2004 | Cates |
| 2004/0214258 A1 | 10/2004 | Wood et al. |
| 2004/0224377 A1 | 11/2004 | Hawkins et al. |
| 2005/0026171 A1 | 2/2005 | Hawkins et al. |
| 2005/0153310 A1 | 7/2005 | Fan et al. |
| 2005/0164321 A1 | 7/2005 | Riss et al. |
| 2005/0272114 A1 | 12/2005 | Darzins et al. |
| 2006/0024808 A1 | 2/2006 | Darzins et al. |
| 2006/0051827 A1 | 3/2006 | Hawkins et al. |
| 2006/0068395 A1 | 3/2006 | Wood et al. |
| 2006/0127988 A1 | 6/2006 | Wood et al. |
| 2006/0183212 A1 | 8/2006 | Wood et al. |
| 2007/0015790 A1 | 1/2007 | Cali et al. |
| 2007/0087400 A1 | 4/2007 | Darzins et al. |
| 2008/0026407 A1 | 1/2008 | Wood et al. |
| 2008/0050760 A1 | 2/2008 | Wood et al. |
| 2008/0070299 A1 | 3/2008 | Wood et al. |
| 2008/0090291 A1 | 4/2008 | Wood et al. |
| 2008/0145882 A1 | 6/2008 | Darzins et al. |
| 2008/0248511 A1 | 10/2008 | Daily et al. |
| 2008/0268482 A1 | 10/2008 | Riss et al. |
| 2008/0274488 A1 | 11/2008 | Darzins et al. |
| 2008/0299593 A1 | 12/2008 | Cali et al. |
| 2009/0017482 A1 | 1/2009 | Riss et al. |
| 2009/0023173 A1 | 1/2009 | Cali et al. |
| 2009/0098627 A1 | 4/2009 | Darzins et al. |
| 2009/0137019 A1 | 5/2009 | Wood et al. |
| 2009/0253131 A1 | 10/2009 | Wigdal et al. |
| 2009/0275051 A1 | 11/2009 | Niles et al. |
| 2009/0305280 A1 | 12/2009 | Binkowski et al. |
| 2009/0311769 A1 | 12/2009 | Wood et al. |
| 2010/0047839 A1 | 2/2010 | Huang et al. |
| 2010/0075350 A1 | 3/2010 | Zegzouti et al. |
| 2010/0273186 A1 | 10/2010 | Wood et al. |
| 2010/0281552 A1 | 11/2010 | Encell |
| 2011/0003316 A1 | 1/2011 | Cali et al. |
| 2011/0039257 A1 | 2/2011 | Binkowski et al. |
| 2011/0081670 A1 | 4/2011 | Hawkins et al. |
| 2011/0171673 A1 | 7/2011 | Darzins et al. |
| 2011/0177540 A1 | 7/2011 | Squirrell et al. |
| 2011/0201024 A1 | 8/2011 | Wood et al. |
| 2011/0207195 A1 | 8/2011 | Darzins et al. |
| 2011/0283373 A1 | 11/2011 | Binkowski et al. |
| 2012/0058505 A1 | 3/2012 | Helms et al. |
| 2012/0064554 A1 | 3/2012 | Kirkland et al. |
| 2012/0107849 A1 | 5/2012 | Klaubert et al. |
| 2012/0117667 A1 | 5/2012 | Klaubert et al. |
| 2012/0174242 A1 | 7/2012 | Binkowski et al. |
| 2013/0130289 A1 | 5/2013 | Benink et al. |
| 2014/0093894 A1 | 4/2014 | Benink et al. |
| 2014/0380514 A1 | 12/2014 | Cali et al. |
| 2015/0064731 A1 | 3/2015 | Klaubert et al. |
| 2015/0212078 A1 | 7/2015 | Zhou et al. |
| 2015/0307916 A1 | 10/2015 | Zhou et al. |

FOREIGN PATENT DOCUMENTS

| | | |
|---|---|---|
| CN | 102459579 | 5/2012 |
| EA | 2366778 A1 | 9/2011 |
| EP | 134108 | 3/1985 |
| EP | 0751996 | 1/2003 |
| EP | 1281762 A2 | 2/2003 |
| EP | 1131441 B1 | 11/2005 |
| EP | 1630231 A2 | 3/2006 |
| EP | 1588143 A4 | 2/2007 |
| EP | 1894933 A2 | 3/2008 |
| EP | 689587 B1 | 4/2008 |
| EP | 1935980 A1 | 6/2008 |
| EP | 1935986 | 6/2008 |
| EP | 1451155 B1 | 7/2008 |
| EP | 1978091 A1 | 10/2008 |
| EP | 1978092 A1 | 10/2008 |
| EP | 1124944 | 12/2008 |
| EP | 1479763 | 12/2008 |
| EP | 2071023 A2 | 6/2009 |
| EP | 2071023 A8 | 6/2010 |
| EP | 1297337 | 1/2011 |
| EP | 2272972 | 1/2011 |
| EP | 2277872 | 1/2011 |
| EP | 2284271 A2 | 2/2011 |
| EP | 2298902 A1 | 3/2011 |
| EP | 2308978 A1 | 4/2011 |
| EP | 2325328 A1 | 5/2011 |
| EP | 2325329 A1 | 5/2011 |
| EP | 1546162 B1 | 6/2011 |
| EP | 2327768 A2 | 6/2011 |
| EP | 2341134 A2 | 7/2011 |
| EP | 2366777 A1 | 9/2011 |
| EP | 2366779 A1 | 9/2011 |
| EP | 2366780 A1 | 9/2011 |
| EP | 2368976 A1 | 9/2011 |
| EP | 2368977 A1 | 9/2011 |
| EP | 2369006 A1 | 9/2011 |
| EP | 2374875 A2 | 10/2011 |
| EP | 2395078 A2 | 12/2011 |
| EP | 2395358 A2 | 12/2011 |
| EP | 2272973 | 1/2012 |
| EP | 2281046 B1 | 1/2012 |
| JP | 08-059686 | 3/1996 |
| JP | H08-294397 | 11/1996 |
| WO | WO 1995/18853 | 7/1995 |
| WO | WO 1995/025798 | 9/1995 |
| WO | WO 1996/007100 | 3/1996 |
| WO | WO 1996/022376 | 7/1996 |

(56) References Cited

FOREIGN PATENT DOCUMENTS

| WO | WO 1998/046739 | 10/1998 |
|---|---|---|
| WO | WO 1999/014336 | 3/1999 |
| WO | WO 2001/020002 | 3/2001 |
| WO | WO 2001/031028 | 5/2001 |
| WO | WO 2001/96862 | 12/2001 |
| WO | WO 2003/040100 | 5/2003 |
| WO | WO 2003/066611 | 8/2003 |
| WO | WO 2004/027378 | 4/2004 |
| WO | WO 2004/059294 | 7/2004 |
| WO | WO 2004/072232 | 8/2004 |
| WO | WO 2004/072299 | 8/2004 |
| WO | 2005/003369 | 1/2005 |
| WO | WO 2005/038029 | 4/2005 |
| WO | WO 2005/073722 | 8/2005 |
| WO | WO 2006/034061 | 3/2006 |
| WO | WO 2006/093529 | 9/2006 |
| WO | WO 2006/130551 | 12/2006 |
| WO | WO 2007/120522 | 10/2007 |
| WO | WO 2008/054821 | 5/2008 |
| WO | WO 2008/086035 | 7/2008 |
| WO | WO 2008/118445 A1 | 10/2008 |
| WO | WO 2008/118445 A9 | 12/2008 |
| WO | WO 2009/061413 | 5/2009 |
| WO | WO 2009/142735 | 11/2009 |
| WO | WO 2010/011607 | 1/2010 |
| WO | WO 2010/127368 | 11/2010 |
| WO | WO 2011/038219 | 3/2011 |
| WO | WO 2011/143339 | 11/2011 |
| WO | WO 2012/030960 | 3/2012 |
| WO | WO 2012/061477 | 5/2012 |
| WO | WO 2012/061529 | 5/2012 |
| WO | WO 2012/061530 | 9/2012 |
| WO | WO 2013/033515 | 3/2013 |
| WO | WO 2014/052653 | 4/2014 |

OTHER PUBLICATIONS

Arnold, K. et al., "The SWISS-MODEL workspace: a web-based environment for protein structure homology modelling," Bioinformatics (2006) 22(2):195-201.

Banaszynski et al., "Characterization of the FKBP-Rapamycin-FRB Ternary Complex" J. Am. Chem. Soc, 127(13):4715-4721(2005).

Becker, M.M. et al., "Gene cloning, overproduction and purification of a functionally active cytoplasmic fatty acid-binding protein (Sj-FABPc) from the human blood fluke Schistosoma japonicum," Gene (1994) 148:321-325.

Benezra et al., "The Protein Id: A Negative Regulator of Helix-Loop-Helix DNA Binding Proteins" Cell, 61(1):49-59(1990).

Berge et al., "Pharmaceutical Salts" J. Pharm. Sci., 66:1-19 (1977).

Burbelo et al., "Antibody-profiling technologies for studying humoral responses to infectious agents" Expert Review of Vaccines 9(6):567-578(2010).

Chenna et al., "Multiple sequence alignment with the Clustal series of programs" Nucl. Acids Res. 31(13):3497-3500 (2003).

Chothia et al., "The relation between the divergence of sequence and structure in proteins" EMBO J. 5(4):823-826 (1986).

Cowan, S.W. et al., "Crystallographic studies on a family of cellular lipophillic transport proteins," J. Mol. Biol. (1993) 230;1225-1246.

Daughiery, P.S. et al., "Quantitative analysis of the effect of the mutation frequency on the affinity maturation of single chain Fv antibodies," Proc. Natl. Acad. Sci. USA (2000) 97(5):2029-2034.

Dennell, R. et al., "Observations on the luminescence of bathypelagic crustacea decapoda of the Bermuda area," Zool. J. Linn. Soc., London (1955) XLII:393-406.

Esteves and Ehrlich 2006. "Invertebrate Intracellular Fatty Acid Binding Proteins." Comparative Biochemistry and Physiology, Part C 142: 262-274.

Fieser, L., et al., "Fieser and Fieser's Reagents for Organic Synthesis," John Wiley and Sons (1994).

Flower, D.R. et al., "A structural signature characteristic of the calycin protein superfamily," Protein Pept. Lett. (1995) 2(2):341-350.

Flower, D.R. et al., "Structure and sequence relationships in the lipocalins and related proteins," Protein Sci. (1993) 2:753-761.

Flower, D.R. et al., "The lipocalin protein family—structure and function," Biochem. J. (1996) 318:1-14.

Flower, D.R. et al., "The lipocalin protein family-structural and sequence overview," Biochimica et Biophysica Acta (2000) 1482:9-24.

Freifelder et al. "Synthesis of Primary 1,2-Diamines by Hydrogenation of alpha-Aminonitriles" Journal of the American Chemical Society, 82(3):696-698(1960).

Fujii, H. et al., "Increase in bioluminescence intensity of firefly luciferase using genetic modification," Anal. Biochem. (2007) 366:131-136.

GenBank 1VPR (2009).
GenBank 2021262A (1992).
GenBank AAA68491 (1995).
GenBank AAC36472 (1998).
GenBank AAL40676 (2005).
GenBank AAL40677 (2005).
GenBank AAV35377 (2004).
GenBank AAV35378 (2004).
GenBank AAV35379 (2004).
GenBank AAV35380 (2004).
GenBank AAV35381 (2004).

Goto, Pure and Applied Chemistry (1968), 17(3-4), pp. 421-441.

Green, T et al., "Protective Groups in Organic Synthesis" Third Edition (1999).

Gross et al., "Real-time imaging of ligand-induced IKK activation in intact cells and in living mice" Nature Methods 2(8):607-614 (2005).

Gunasekaran et al. 2004. "Sequence and Structural Analysis of Cellular Retinoic Acid-Binding Proteins Reveals a Network of Conserved Hydrophobic Interactions." Proteins 54: 179-194.

Hagedorn et al., "Darstellung von a.&ungesattigten Isonitrilen, &Keto- and &Chlor-isonitrilen. Synthese des Xanthocillin-dimethylathers" Chem. Ber., 98:193(1965).

Hawkins, et al., "Bright Light, No Lysis," Promega, 2005, pp. 10-14.

Head, J.F. et al., "The crystal structure of the photoprotein aequorin at 2.3A resolution," Nature (2000) 405:372-376.

Herring, P.J. et al., "Bioluminescence in crustacea," J. Crust. Biol. (1985) 5(4):557-573.

Herring, P.J. et al., "The spectral characteristics of luminous marine organisms," Proc. Royal Society London Series B. Biological Sciences (1983) 220(1219):183-217.

Herring, P.J., "Bioluminescence in decapod crustacea," J. Mar. Biol. Assoc. UK (1976) 156:1029-1047.

Huang, S., et al., "Synthesis of a new long-wavelength latent fluorimetric indicator for analytes determination in the DT-Diaphorase coupling dehydrogenase assay system," Bionsensors & Bioelectronics, 2008, 23(12), pp. 1793-1798.

Inoue et al. "Squid bioluminescence. II. Isolation from Watasenia scintillans and synthesis of 2-(p-hydroxybenzyl)-6-(p-hydroxyphenyl)-3,7-dihydroimidazo[1,2-a]pyrazin-3-one" Chem. Lett., 4(2):141-144 (1975).

Inoue et al. Chemical studies of myctophina fish bioluminescence, Chemistry Letters (1987), (2), 417-18.

Inoue, S. et al., "Complete structure of renilla luciferin and luciferyl sulfate," Tetra. Lett (1977) 31:2685-2688.

Inouye, S. et al., "Overexpression, purification and characterization of the catalytic component of oplophorus luciferase in the deep sea shrimp," Protein Exp. Purification (2007) 56(2):261-268.

Inouye, S. et al., "Secretional luciferase of the luminous shrimp oplophorus gracilirostris: cDNA cloning of a novel imidazopyrazinone luciferase," FEBS Letts. (2000) 481:19-25.

Inouye, S. et al., "The use of renilla luciferase, oplophorus luciferase, and apoaequorin as biolumineinscent reporter rpotein in the presence of coelenterazine analogues as substrate," Biochem. Biophys. Res. Comm. (1997) 233:349-353.

International Union of Pure and Applied Chemistry "Definitive Rules for Nomenlature of Organic Chemistry" J. Am. Chem. Soc. 1960, 82, 5545-5574.

(56) References Cited

OTHER PUBLICATIONS

Johnson, F.H. et al., "Introduction to the cypridina system," Meth. Enzym. (1978) 57:331-364.

Kabsch, W. et al., "Dictionary of protein secondary structure: pattern recognition of hydrogen-bonded and geometrical features," Biopolymers (1983) 22:2577-2637.

Kakoi et al., "A New Synthesis of Watasenia Preluciferin by Cyclization of 2-Amino-3-Benzyl-5-(p-Hydroxyphenyl)Pyrazine With p-Hydroxyphenylpyruviacc" Chem. Lett. 11(3):299-300 (1980).

Kakoi, "Synthesis of 2-Amino-3-benzyl-5-(p-hydroxyphenyl)pyrazine" Chem. Pharm. Bull., 50:301 (2002).

Karplus, K. et al., "Hidden Markov models for detecting remote protein homologies," Bioinformatics (1998) 14(10):846-856.

King, R.D. et al., "Identification and application of the concepts important for accurate and reliable protein secondary structure prediction," Protein Sci. (1996) 5:2298-2310.

Kishi et al., "The structure confirmation of the light-emitting moiety of bioluminescent jellyfish" Tetrahedron Lett. 13(27):2747(1972).

Kunkel, T.A., "Rapid and efficient site-specific mutagenesis without phenotypic selection," Proc. Natl. Acad. Sci. USA (1985) 82(2):488-492.

Kurowski, M.A. et al., "GeneSilico protein structure prediction meta-server," Nucl. Acids. Res. (2003) 31(13):3305-3307.

Langley et al., "Molecular Basis of O-Galactosidase a-Complementation PNAS (protein sequencing/protein conformation/deletion mutant)" 72:1254-1257 (1975).

Larock, R., "Comprehensive Organic Transformations, A Guide to Functional Group Preparation"s VCH Publishers (1989).

Levit et al., "Ribonuclease S-Peptide—A Model for Molecular Recognition" J. Biol. Chem. 251:1333-1339 (1976).

Loening, A.M. et al., "Consensus guided mutagenesis of renilla luciferase yeilds enhanced stability and light output," Protein Eng. Des. Sel. (2006) 19(9):391-400.

Lorenz, W.W. et al., "Isolation and expression of a cDNA encoding renilla reinformis luciferase," Proc. Natl. Acad. Sci. USA (1991) 88:4438-4442.

Marcelino et al. 2006. "Evolutionary Coupling of Structural and Functional Sequence Information in the Intracellular Lipid-Binding Protein Family." PROTEINS 63: 373-384.

McGuffin, L.J. et al., "The PSIPRED protein structure prediction server," Bioinformatics (2000) 16(4):404-405.

Mitani et al., "Enhancement effect of 2, 6-O-dimethyl-cyclodextrin on the chemiluminescent detection of -D-galactosidase using a Cypridina luceferin analog" Analytical Sciences (1995) 11(6), 1013-15.

Mitani, M. et al., "Chemiluminescent assay of beta-D-galactosidase using cypridina luciferin analogue: 3-(Beta-D-galactopyranosyloxy)-6-(4-methoxyphenyl)-2-methyl-imidazol[1,2-alpha]pyrazine," Anal. Sci. (1994) 10(50:813-814.

Moroz et al., "Real-Time Imaging of HIF-1a Stabilization and Degradation" Plos One 4(4):e5077 (2009).

Mosrin et al., "Regio- and Chemoselective Multiple Functionalization of Chloropyrazine Derivatives. Application to the Synthesis of Coelenterazine" Organic Letters, 11:3406 (2009).

Murray, E.E. et al., "Codon usage in plant genes," Nucl. Acids. Res. (1989) 17(2):477-498.

Nakamura, H. et al., "Efficient bioluminescence of bisdeoxycoelenterazine with the luciferase of a deep-sea shrimp oplophorus," Tetra. Lett. (1997) 38(36):6405-6406.

Needleman, S.B. et al., "A general method applicable to the search for similarities in the amino acid sequence of two proteins," J. Mol. Biol. (1970) 48:443-453.

Nowel, M.S. et al., "Cuticular photophores of two decapod crustaceans, oplophorus spinosus and systellaspis debilis," Biol. Bull. (1998) 195:290-307.

Oba et al. 2009. "Biosynthesis of coelenterazine in the deep-sea copepod, Metridia pacifica. Biochem." Biophys. Res. Comm. 390: 684-688.

Ogbay et al. 2004. "The NMR Structure of a Stable and Compact All β-sheet Variant of Intestinal Fatty-Acid Binding Proteins." Protein Science 13: 1227-1237.

Ohana et al., "HaloTag7: A genetically engineered tag that enhances bacterial expression of soluble proteins and improves protein purification" Protein Expression and Purification, 68:110-120 (2009).

Oxford Dictionary of Biochemistry and Molecular Biology. Diaphorase. Oxford University Press. Second Edition. 2006. The General Editors. New York, New York, p. 178.

Paguio et al., "pGL4 Vectors: A New Generation fo Luciferase Reporter Vectors" Promega Notes, 89:7-10 (2005).

Paquette, L., ed., "Encyclopedia of Reagents for Organic Synthesis," John Wiley and Sons (1995).

Paquette, Leo A.; "Principles of Modem Heterocyclic Chemistry" (W.A. Benjamin, New York, 1968), particularly Chapters 1, 3, 4, 6, 7, 9.

Parsons, M.R. et al., "Crystal structure of a quinoenzyme: copper amine oxidase of *Escherichia coli* at 2 A resolution," Structure (1995) 3:1171-1184.

Pearson, W.R. et al., "Improved tools for biological sequence comparison," Proc. Natl. Acad. Sci. USA (1988) 85:2444-2448.

Pichler, A. et al., "Imaging reversal of multidrug resistance in living mice with bioluminescence: MDR1 P-glycoprotein transports coelenterazine," Proc. Natl. Acad. Sci. USA (2004) 101(6):1702-1707.

Pollastri, G. et al., "Porter: a new, accurate server for protein secondary structure prediction," Bioinformatics (2005) 21(8):1719-1720.

Poupin, J., "Plancton marin bioluminescent," Rapport Scientifique du Leon (Sep. 1999) 1-83.

Raphael et al., "A novel method for multiple alignment of sequences with repeated and shuffled elements" Genome Res. 14(11):2336-2346 (2004).

Rea et al. 2009. "Mechanism of Ligand-Induced Folding of a Natively Unfolded Helixless Variant of Rabbit I-BABP." Biochemistry 48: 7556-7564.

Richardson and Richardson. 2002. "Natural β-sheet Proteins Use Negative Design to Avoid Edge-to-Edge Aggregation." PNAS 99(5): 2754-2479.

Schagat, T. et al., "KRX autoinduction protocol: a convenient metod for protein expression," Promega Notes (2008) 98:16-18.

Schultz, L.W. et al., "Crystal structure of a pH-regulated luciferase catalyzing the bioluminescent oxidation of an open tetrapyrrole," Proc. Natl. Acad. Sci. USA (2005) 102(5):1378-1383.

Shimomura et al. 1997. "Membrane Permeability of Coelenterazine Analogs Measured with Fish Eggs." Biochem J. 326: 297-298.

Shimomura, O. et al., "Properties and reaction mechanism of the bioluminescence system of the deep-sea shrimp oplophorus gracilorostris," Biochem. (1978) 17:994-998.

Shimomura, O. et al., "Semi-synthetic aequorin. An improved tool for the measurement of calcium concentration," Biochemical Journal, 1988, vol. 251, No. 2, pp. 405-410.

Shimomura, O. et al., "Semi-synthetic aequorins with improved sensitivity to CA2+ ions," Biochem. J. (1989) 261:913-920.

Sigrist et al., "PROSITE, a protein domain database for functional characterization and annotation" Nucleic Acids Res. 38(suppl 1):D161-D166(2010).

Silvers, W.C., et al., "Shedding light by cancer redox—human NAD(P)H: quinone oxidoreductase 1 activation of a cloaked fluorescent dye" Chemical Communications, vol. 47, 2011, 11264-11266.

Skerra, A., "Lipocalins as a scaffold," Biochem et Biophys. Acta (2000) 1482:337-350.

Skolnick, J. et al., "From genes to protein structure and function: novel applications of computational approaches in the genomic era," Trends in Biotech. (2000) 18:34-39.

Smathers and Petersen. 2011. "The Human Fatty Acid-Binding Protein Family: Evolutionary Divergences and Functions." Human Genomics 5(3): 170-191.

Smith, T.F. et al., "Identification of common molecular subsequences," J. Mol. Biol. (1981) 147:195-197.

(56) References Cited

OTHER PUBLICATIONS

Teranishi et al. 1990. "Synthesis and Chemiluminescence of Coelenterazine (Oplophorus Luciferin) Analogues." Bull. Chem. Soc. Jpn. 63: 3132-3140.
Thompson et al. 1995. "Crystal Structure of Cellular Retinoic Acid Binding Protein 1 Shows increased Access to the Binding Cavity Due to Formation of an Intermolecular β-sheet." J. Mol. Biol. 252: 433-446.
Thompson, E.M. et al., "Cloning and expression of cDNA for the luciferase from the marine ostracod Vargula hilgendorfii," Proc. Natl. Acad. Sci. USA (1989) 86:6567-6571.
Tramontano, "Comparative modelling techniques: where are we?" Genomics, 4:402-405 (2003).
Wada, K. et al., "Codon usage tabulated from the GenBank genetic sequence data," Nucl. Acids Res. (1990) 18(Supp):2367-2411.
Weissberger, A., ed., "The Chemistry of Heterocyclic Compounds, A Series of Monographs," (John Wiley & Sons, New York, 1950 to present), in particular vols. 13, 14, 16, 19, and 28.
Yamaguchi et al. 1975. "Oplophorus Oxyluciferin and a Model Luciferin Compound Biologically Active with Oplophorus Luciferase." Biochem. J. 151: 9-15.
Zhang et al., "A Universal Algorithm for Fast and Automated Charge State Deconvolution of Electrospray Mass-to-Charge Ratio Spectra" J. Am. Soc. Mass Spectrom., 9:225-233 (1998).
Zheng et al., "An efficient one-step site-directed and site-saturation mutagenesis protocol" Nucleic Acids Research, 32:e115 (2004).
Zuker et al., "Mfold web server for nucleic acid folding and hybridization prediction" Nucleic Acid Res. 31(13):3406-3415(2003).
Roubinet et al: "New insights into the water-solubilization of thiol-sensitive fluorogenic probes based on long-wavelength 7-hydroxycoumarin scaffolds", Dyes and Pigments, vol. 110, Feb. 12, 2014, pp. 270-284.
International Search Report and Written Opinion for Application No. PCT/US2010/033449 dated Aug. 18, 2010 (12 pages).
International Search Report and Written Opinion for Application No. PCT/US2011/058924 dated Jan. 18, 2012 (8 pages).
International Search Report and Written Opinion for Application No. PCT/US2011/059017 dated Jan. 18, 2012 (8 pages).
International Search Report and Written Opinion for Application No. PCT/US2011/059018 dated Jul. 12, 2012 (15 pages).
International Search Report and Written Opinion for Application No. PCT/US2015/013504 dated Mar. 24, 2015 (12 pages).
PCT/US2012/053310 International Search Report and Written Opinion dated Dec. 18, 2012 (13 pages).
United States Patent Office Action for U.S. Appl. No. 12/773,002 dated Dec. 29, 2011 (11 pages).
United States Patent Office Action for U.S. Appl. No. 13/287,519 dated Feb. 27, 2015 (8 pages).
United States Patent Office Action for U.S. Appl. No. 13/287,519 dated Jul. 2, 2014 (10 pages).
United States Patent Office Action for U.S. Appl. No. 13/287,519 dated Nov. 7, 2014 (7 pages).
United States Patent Office Action for U.S. Appl. No. 13/287,992 dated Apr. 4, 2013 (9 pages).
United States Patent Office Action for U.S. Appl. No. 13/600,579 dated Apr. 28, 2014 (19 pages).
United States Patent Office Action for U.S. Appl. No. 13/600,579 dated Jun. 6, 2014 (21 pages).
United States Patent Office Action for U.S. Appl. No. 13/600,579 dated Mar. 12, 2015 (12 pages).
United States Patent Office Action for U.S. Appl. No. 13/600,579 dated Oct. 24, 2013 (15 pages).
United States Patent Office Action for U.S. Appl. No. 14/032,420 dated Mar. 25, 2015 (19 pages).
United States Patent Office Action for U.S. Appl. No. 14/461,610 dated Feb. 3, 2015 (15 pages).
United States Patent Office Notice of Allowance for U.S. Appl. No. 14/461,610 dated May 15, 2015 (9 pages).
United States Patent Office Final Rejection for U.S. Appl. No. 12/773,002 dated Jun. 1, 2012 (17 pages).
United States Patent Office Final Rejection for U.S. Appl. No. 13/287,519 dated Apr. 24, 2013 (10 pages).
United States Patent Office Final Rejection for U.S. Appl. No. 13/287,519 dated Sep. 6, 2013 (8 pages).
United States Patent Office Final Rejection for U.S. Appl. No. 13/287,992 dated Jul. 11, 2013 (7 pages).
United States Patent Office Final Rejection for U.S. Appl. No. 13/600,579 dated Nov. 14, 2014 (14 pages).
United States Patent Office Notice of Allowance for U.S. Appl. No. 13/287,992 dated Apr. 1, 2014 (11 pages).
United States Patent Office Notice of Allowance for U.S. Appl. No. 13/287,992 dated Nov. 18, 2013 (12 pages).
United States Patent Office Notice of Allowance for U.S. Appl. No. 13/287,519 dated Jun. 5, 2015 (5 pages).
United States Patent Office Final Rejection for U.S. Appl. No. 13/600,579 dated Jun. 26, 2015 (14 pages).
United States Patent Office Action for U.S. Appl. No. 14/032,420 dated Aug. 12, 2015 (19 pages).
International Search Report and Written Opinion for Application No. PCT/US2015/013617 dated Mar. 24, 2015 (11 pages).
United States Patent Office Notice of Allowance for U.S. Appl. No. 13/600,579 dated Oct. 21, 2015 (12 pages).
United States Patent Office Final Action for U.S. Appl. No. 14/609,372 dated Feb. 2, 2017 (7 pages).
United States Patent Office Action for U.S. Appl. No. 14/609,372 dated Sep. 29, 2016 (15 pages).
Hart, et al. "Renilla reniformis Bioluminescence: Luciferase-Catalyzed Production of Nonradiating Excited States from Luciferin Analogues and Elucidation of the Excited State Species Involved in Energy Transfer to Renilla Green Fluorescent Protein," Biochemistry, 18(11 ), 1979, 2204-2210.
Hall, et al. "Engineered Luciferase Reporter from a Deep Sea Shrimp Utilizing a Novel Imidazopyrazinone Substrate," ACS Chemical Biology, 7(11), 2012, 1848-1857.
United States Patent Office Action for U.S. Appl. No. 14/859,715 dated Feb. 14, 2017 (19 pages).
United States Patent Office Action for U.S. Appl. No. 14/032,420 dated Feb. 27, 2017 (24 pages).
United States Patent Office Notice of Allowance for U.S. Appl. No. 14/609,372 dated May 16, 2017 (7 pages).

10% FBS 0.5% FBS

Cell viability at 2 hrs

10% FBS 0.5% FBS

Cell viability at 2 hrs

10% FBS

10% FBS 0.5% FBS 0.5% FBS

Cell viability at 16.5 hrs

PRO-SUBSTRATES FOR LIVE CELL APPLICATIONS

CROSS-REFERENCE TO RELATED APPLICATIONS

This application claims priority to U.S. Provisional Application 61/933,210, filed Jan. 29, 2014, and is herein incorporated by reference in its entirety.

TECHNICAL FIELD

The present disclosure relates generally to compounds, compositions, and methods for assaying the presence and/or activity of enzymes.

BACKGROUND

Reporter molecules are routinely used to monitor molecular events in the fields of biology, biochemistry, immunology, cell biology and molecular biology. For example, reporter molecules are employed in assays where the levels of the reporter molecule are due to transcription from a specific promoter linked to the reporter molecule. Reporter molecule assays can be used to study biological processes including gene expression, receptor activity, transcription factors, intracellular signaling, mRNA processing, and protein folding. Analysis of reporter molecules that are typically used in such assays includes detection of radioactive isotopes, enzyme activity, fluorescence, or luminescence.

Luminescence in biological assays typically involves the activity of a luminogenic protein. Luminogenic proteins that are useful in assay systems include, but are not limited to, *Renilla* luciferase, *Oplophorus* luciferase, *Vargula* (*Cypridina*) luciferase, *Gaussia* luciferase, and aequorin. In a luminescent reaction, the interaction of a luminogenic protein with an appropriate molecule, referred to as a luminophore, produces light as one of the reaction products. The quantity of light produced in the reaction can be measured. This measurement may be used qualitatively to determine if a certain substance or target of interest is or is not present in a sample. This measurement also may be used quantitatively to calculate the concentration of luminogenic protein, luminophore, and/or substance or target of interest in the reaction.

Luminescent reactions can be used to detect very small quantities of a particular analyte, the substance being identified and measured in an assay. For example, luminescent reactions can be used to detect and quantify proteases, lipases, phosphatases, peroxidases, glycosidases, various metabolites such as ATP or NADH, and reporter molecules. Luminescent reactions can also be used to detect and quantify analytes through binding interactions, such as those mediated by antibodies and nucleotide probes. Another application of luminescent reactions is bioluminescence resonance energy transfer (BRET), which can determine if two molecules are capable of binding to each other or are co-localized in a cell. Typically, luminescent reactions can be used to detect an analyte present in a sample at less than about $1 \times 10^{-16}$ moles, often less than $1 \times 10^{-19}$ moles.

Coelenterazines are reporter molecules known to luminesce when acted on by a wide variety of bioluminescent proteins such as marine luciferases. Examples of such marine luciferases include *Renilla* luciferase, *Aequorin*, *Gaussia* luciferase, and *Oplophorus* luciferase.

SUMMARY

In one aspect, disclosed is a compound of formula (I), or a salt thereof,

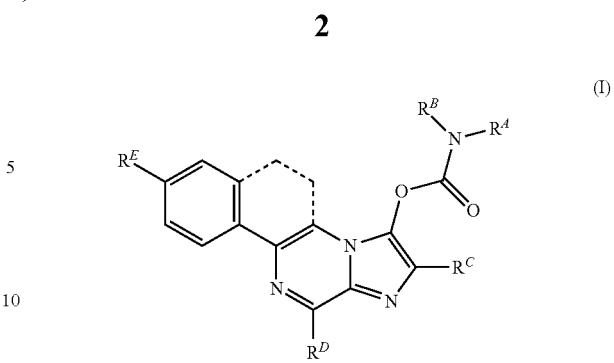

wherein, $R^A$ is a cell impermeable moiety;

$R^B$ is a moiety comprising a functional group configured to react with the carbonyl group of $-OC(O)NR^AR^B$ (e.g., the functional group may catalyze nucleophilic addition to the carbonyl group of $-OC(O)NR^AR^B$ and/or the functional group may undergo a nucleophilic addition reaction with the carbonyl group of $-OC(O)NR^AR^B$);

$R^C$ is alkyl, aryl, heteroaryl, heterocyclyl, cycloalkyl, arylalkyl, heteroarylalkyl, heterocyclylalkyl, or cycloalkylalkyl, wherein said aryl, heteroaryl, heterocyclyl, cycloalkyl, arylalkyl, heteroarylalkyl, heterocyclylalkyl, and cycloalkylalkyl are each independently unsubstituted or substituted with one or more suitable substituents;

$R^D$ is hydrogen, alkyl, arylalkyl, cycloalkyl, or cycloalkylalkyl;

$R^E$ is hydrogen, hydroxy, alkoxy, amino, alkylamino, di(alkyl)amino, $-OC(O)$alkyl, or $-OCH_2OC(O)$alkyl;

wherein the dash bonds together indicate the presence of an optional 6-membered ring in the compound of formula (I), wherein the optional ring is saturated or unsaturated.

In certain embodiments, $R^A$ is selected from the group consisting of alkyl, alkoxy, alkenyl, alkynyl, aryl, heteroaryl, heterocyclyl, and cycloalkyl, wherein said alkyl, alkoxy, alkenyl, alkynyl, aryl, heteroaryl, heterocyclyl, and cycloalkyl are each independently unsubstituted or substituted with one or more suitable substituents;

$R^B$ is aminoalkyl or thioalkyl, wherein said alkyl is unsubstituted or substituted with one or more suitable substituents, and wherein said amino of the aminoalkyl is unsubstituted or substituted with one or more suitable substituents, or wherein the nitrogen atom of the aminoalkyl forms part of a heterocyclic group, wherein said heterocyclic group is unsubstituted or substituted with one or more suitable substituents;

$R^C$ is alkyl, aryl, heteroaryl, heterocyclyl, cycloalkyl, arylalkyl, heteroarylalkyl, heterocyclylalkyl, or cycloalkylalkyl, wherein said aryl, heteroaryl, heterocyclyl, cycloalkyl, arylalkyl, heteroarylalkyl, heterocyclylalkyl, and cycloalkylalkyl are each independently unsubstituted or substituted with one or more suitable substituents;

$R^D$ is hydrogen, alkyl, arylalkyl, cycloalkyl, or cycloalkylalkyl; and $R^E$ is hydrogen, hydroxy, alkoxy, amino, alkylamino, di(alkyl)amino, $-OC(O)$alkyl, or $-OCH_2OC(O)$alkyl;

wherein the dash bonds together indicate the presence of an optional 6-membered ring in the compound of formula (I), wherein the optional ring is saturated or unsaturated.

In certain embodiments, $R^A$ is selected from the group consisting of alkyl, alkoxyalkyl, haloalkyl, haloalkoxyalkyl, hydroxyalkyl, aminoalkyl, alkylaminoalkyl, di(alkyl)aminoalkkyl, tetraalkylammoniumalkyl, pyridiniumalkyl, azidoalkyl, cyanoalkyl, maleimidoalkyl, alkoxy, haloalkoxy, alkoxyalkoxy, alkenyl, alkynyl, $-(CR^1R^2)_m-N(R^3)C(O)R^4$, $-(CR^5R^6)_m-SO_3R^7$, $-(CR^5R^6)_m-OPO_2R^7$, $-(CR^5R^6)_m-SO_2N(R^8)(R^9)$, $-(CR^{10}R^{11})_m-CO_2R^{12}$, $-(CR^{13}R^{14})_m-CON(R^{15})(R^{16})$, $-(CR^{17}R^{18})_m-ON(R^{19})(R^{20})$, $-(CR^{21}R^{22})_m$-heterocyclyl-$(CR^{23}R^{24})_n-R^{25}$, $-(CR^{26}R^{27})_m$-heteroaryl-$(CR^{28}R^{29})_n-R^{30}$, $-(CR^{31}R^{32})_m$-aryl-$(CR^{33}R^{34})_n-R^{35}$, and $-(CR^{36}R^{37})_m$-cycloalkyl-$(CR^{38}R^{39})_n-R^{40}$, $R^1$, $R^2$, $R^3$, $R^5$, $R^6$, $R^8$, $R^{10}$, $R^{11}$, $R^{13}$, $R^{14}$, $R^{15}$, $R^{17}$, $R^{18}$, $R^{19}$, $R^{21}$, $R^{22}$, $R^{23}$, $R^{24}$, $R^{26}$, $R^{27}$, $R^{28}$, $R^{29}$, $R^{31}$, $R^{32}$, $R^{33}$, $R^{34}$, $R^{36}$, $R^{37}$, $R^{38}$, and $R^{39}$ are each independently selected from the group consisting of hydrogen and alkyl;

$R^4$, $R^7$, $R^9$, $R^{12}$, $R^{16}$, $R^{20}$, $R^{25}$, $R^{30}$, $R^{35}$, and $R^{40}$ are each independently selected from the group consisting of hydrogen, alkyl, alkoxy, alkylcarbonyl, alkylcarbonylalkoxylalkyl, alkylcarbonyloxyalkyl, alkoxycarbonylalkyl, hydroxy-(mono or polyalkoxy)alkyl, carboxyalkyl, carboxyalkoxyalkyl, suflonate alkyl, tetraalkylammoniumalkyl, pyridiniumalkyl, aryl, heteroaryl, heterocyclyl, cycloalkyl, arylalkyl, heteroarylalkyl, heterocyclylalkyl, cycloalkylalkyl,

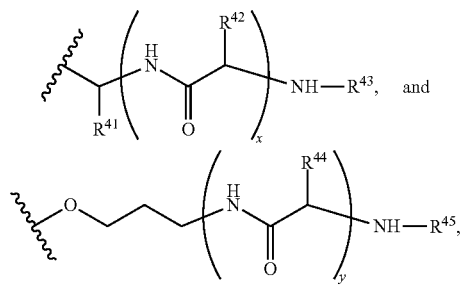

wherein said aryl, heteroaryl, heterocyclyl, cycloalkyl, arylalkyl, heteroarylalkyl, heterocyclylalkyl, and cycloalkylalkyl of $R^4$, $R^7$, $R^9$, $R^{12}$, $R^{16}$, $R^{20}$, $R^{25}$, $R^{30}$, $R^{35}$, and $R^{40}$ are each independently unsubstituted or substituted with 1, 2, 3, 4, or 5 substituents independently selected from halogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino;

$R^{41}$, $R^{42}$, and $R^{44}$, at each occurrence, are each independently selected from the group consisting of hydrogen, alkyl, carboxyalkyl, aminoalkyl, alkylaminoalkyl, di(alkyl)aminoalkyl, sulfonate alkyl, tetraalkylammoniumalkyl, pyridiniumalkyl, imidazolylalkyl, guanidinolalkyl, hydroxyalkyl, carboxamidealkyl, thioalkyl, selanylalkyl, pyrrolidinyl, methylthioalkyl, phenylalkyl, 4-hydroxyphenylalkyl, and indolylalkyl;

$R^{43}$ and $R^{45}$ are each independently selected from the group consisting of hydrogen, —C(O)alkyl, and

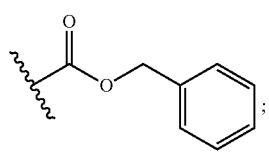

m, and n are each independently 1, 2, 3, 4, 5, or 6; x, and y are each independently an integer selected from 1 to 20;

$R^B$ is $-(CR^{46}R^{47})_t-NR^{48}R^{49}$ or $-(CR^{53}R^{54})_z-SR^{55}$;

$R^{46}$ and $R^{47}$, at each occurrence, are each independently selected from the group consisting of hydrogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, hydroxy, amino, alkylamino, and di(alkyl)amino;

$R^{48}$ and $R^{49}$ are each independently selected from hydrogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, $-(CR^{50}R^{51})_z-OC(O)R^{52}$, $-(CR^{53}R^{54})_z-SR^{55}$, $-(CR^{56}R^{57})_z-S(O)R^{58}$, $-(CR^{59}R^{60})_z-S(O)_2R^{61}$, $-(CR^{62}R^{63})_z-N(R^{64})(R^{65})$, $-(CR^{66}R^{67})_z-N(R^{68})C(O)R^{69}$, $-(CR^{70}R^{71})_z-N(R^{72})S(O)_2R^{73}$, $-(CR^{74}R^{75})_z-N(R^{76})C(O)N(R^{77})(R^{78})$, $-(CR^{79}R^{80})_z-N(R^{81})S(O)_2N(R^{82})(R^{83})$, $-(CR^{84}R^{85})_z-C(O)R^{86}$, $-(CR^{87}R^{88})_z-C(O)O(R^{89})$, $-(CR^{90}R^{91})_z-C(O)N(R^{92})(R^{93})$, and $-C(R^{94})=N-OR^{95}$;

or $R^{48}$ and $R^{49}$ together with the nitrogen atom to which they are attached form a heterocyclyl, wherein said heterocyclyl is unsubstituted or substituted with 1, 2, 3, 4, 5 or 6 substituents independently selected from the group consisting of alkyl, alkenyl, alkynyl, $-NO_2$, $-CN$, halogen, oxo, $-OR^{96}$, $-OC(O)R^{97}$, $-SR^{98}$, $-S(O)R^{99}$, $-S(O)_2R^{100}$, $-S(O)_2N(R^{101})(R^{102})$, $-N(R^{103})(R^{104})$, $-N(R^{105})C(O)R^{106}$, $-N(R^{107})S(O)_2R^{108}$, $-N(R^{109})C(O)N(R^{110})(R^{112})$, $-N(R^{113})S(O)_2N(R^{114})(R^{115})$, $-C(O)R^{116}$, $-C(O)O(R^{117})$, $-C(O)N(R^{118})(R^{119})$, haloalkyl, $-(CR^{120}R^{121})_z-CN$, $-(CR^{122}R^{123})_z-OR^{124}$, $-(CR^{125}R^{126})_z-OC(O)R^{127}$, $-(CR^{128}R^{129})_z-SR^{130}$, $-(CR^{131}R^{132})_z-S(O)R^{133}$, $-(CR^{134}R^{135})_z-S(O)_2R^{136}$, $-(CR^{137}R^{138})_z-N(R^{139})(R^{140})$, $-(CR^{141}R^{142})_z-N(R^{143})C(O)R^{144}$, $-(CR^{145}R^{146})_z-N(R^{147})S(O)_2R^{148}$, $-(CR^{149}R^{150})_z-N(R^{151})C(O)N(R^{152})(R^{153})$, $-(CR^{154}R^{155})_z-N(R^{156})S(O)_2N(R^{157})(R^{158})$, $-(CR^{159}R^{160})_z-C(O)R^{161}$, $-(CR^{162}R^{163})_z-C(O)O(R^{164})$ and $-(CR^{165}R^{166})_z-C(O)N(R^{167})(R^{168})$;

$R^{52}$, $R^{55}$, $R^{64}$, $R^{65}$, $R^{68}$, $R^{72}$, $R^{69}$, $R^{76}$, $R^{77}$, $R^{81}$, $R^{82}$, $R^{86}$, $R^{89}$, $R^{92}$, $R^{93}$, $R^{96}$, $R^{97}$, $R^{98}$, $R^{101}$, $R^{102}$, $R^{103}$, $R^{104}$, $R^{105}$, $R^{106}$, $R^{107}$, $R^{109}$, $R^{110}$, $R^{112}$, $R^{113}$, $R^{114}$, $R^{115}$, $R^{116}$, $R^{117}$, $R^{118}$, $R^{119}$, $R^{124}$, $R^{127}$, $R^{130}$, $R^{139}$, $R^{140}$, $R^{143}$, $R^{144}$, $R^{147}$, $R^{151}$$R^{152}$, $R^{153}$ $R^{156}$, $R^{157}$, $R^{158}$, $R^{161}$, $R^{164}$, $R^{167}$, and $R^{168}$, at each occurrence, are each independently selected from the group consisting of hydrogen, alkyl, alkoxyalkyl, aryl, arylalkyl, heteroaryl, heteroarylalkyl, cycloalkyl, cycloalkylalkyl, heterocyclyl, heterocyclylalkyl, haloalkoxyalkyl, and haloalkyl;

$R^{58}$, $R^{61}$, $R^{73}$, $R^{99}$, $R^{100}$, $R^{108}$, $R^{133}$, $R^{136}$, and $R^{148}$, at each occurrence, are each independently selected from alkyl and haloalkyl;

$R^{50}$, $R^{51}$, $R^{53}$, $R^{54}$, $R^{56}$, $R^{57}$, $R^{59}$, $R^{60}$, $R^{62}$, $R^{63}$, $R^{66}$, $R^{67}$, $R^{70}$, $R^{71}$, $R^{74}$, $R^{75}$, $R^{79}$, $R^{80}$, $R^{84}$, $R^{85}$, $R^{87}$, $R^{88}$, $R^{90}$, $R^{91}$, $R^{120}$, $R^{121}$, $R^{122}$, $R^{123}$, $R^{125}$, $R^{126}$, $R^{128}$, $R^{129}$, $R^{131}$, $R^{132}$, $R^{134}$, $R^{135}$, $R^{137}$, $R^{138}$, $R^{141}$, $R^{142}$, $R^{145}$, $R^{146}$, $R^{149}$, $R^{150}$, $R^{154}$, $R^{155}$, $R^{159}$, $R^{160}$, $R^{162}$, $R^{163}$, $R^{165}$, and $R^{166}$, at each occurrence, are each independently selected from hydrogen, halogen, alkyl, and haloalkyl;

$R^{94}$, and $R^{95}$, at each occurrence, are each independently selected from hydrogen and alkyl;

t is 1, 2, 3, 4, 5, 6, 7, or 8;

z, at each occurrence, is independently 1, 2, 3, or 4;

$R^C$ is $-(CH_2)_{0-3}-T$ or $C_{1-5}$ alkyl; wherein T is aryl, heteroaryl, or cycloalkyl, wherein said aryl, heteroaryl, and cycloalkyl are each independently unsubstituted or substituted with 1, 2, or 3 substituents independently selected from the group consisting of halogen, alkyl, haloalkyl, hydroxyalkyl, alkoxyalkyl, haloalkoxyalkyl, aminoalkyl, alkylaminoalkyl, di(alkylaminoalkyl), cyanoalkyl, alkoxy, haloalkoxy, cyano, hydroxy, amino, alkylamino, and di(alkyl)amino;

$R^D$ is selected from the group consisting of hydrogen, lower cycloalkyl, benzyl, and $C_1$-$C_4$-alkyl; and $R^E$ is selected from the group consisting of —H, —OH, —NH$_2$, —OC(O)—$C_1$-$C_7$-alkyl or —OCH$_2$OC(O)—$C_1$-$C_7$-alkyl;

wherein the dashed bonds of formula (I) indicate the presence of an optional ring, which may be saturated or unsaturated.

In certain embodiments, $R^A$ is —(CR$^1$R$^2$)$_m$—N(R$^3$)C(O)R$^4$, wherein m is 2, 3, or 4; $R^1$ and $R^2$ are hydrogen at each occurrence; $R^3$ is hydrogen or methyl; and $R^4$ is as defined above.

In certain embodiments, $R^4$ is tert-butoxy, phenyl, methyl, 4-trifluoromethylphenyl, isopropyl, 4-methoxyphenyl, or 4-fluorophenyl.

In certain embodiments, $R^A$ is selected from the group consisting of:

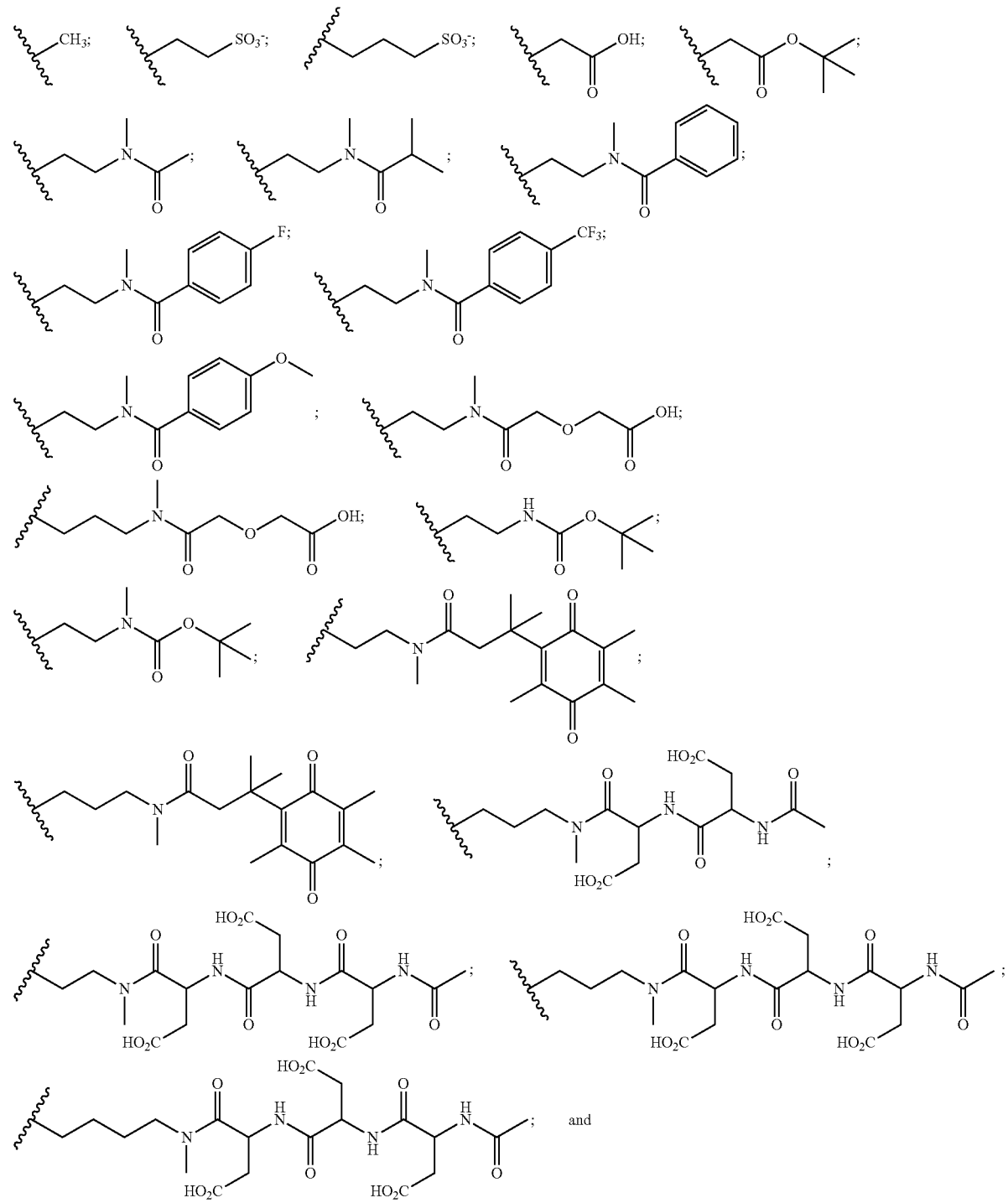

-continued

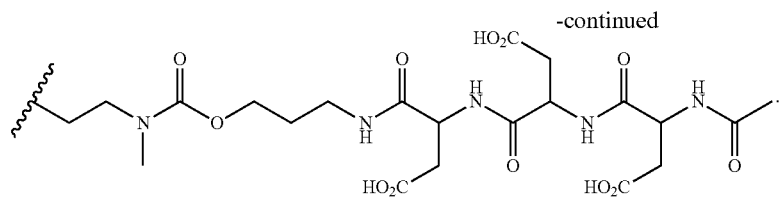

In certain embodiments, $R^B$ is morpholinylalkyl.

In certain embodiments, $R^B$ is selected from the group consisting of:

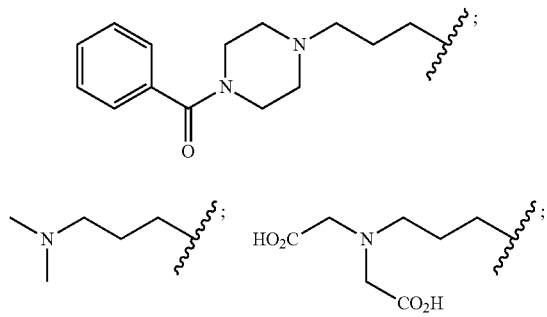

and

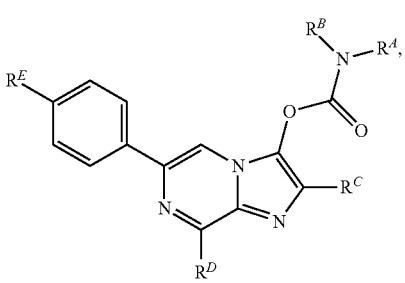

In certain embodiments, $R^C$ is furylmethyl.
In certain embodiments, $R^C$ is benzyl.
In certain embodiments, $R^D$ is benzyl.
In certain embodiments, $R^E$ is hydrogen.
In certain embodiments, the compound of formula (I) has formula (I-i), or a salt thereof,

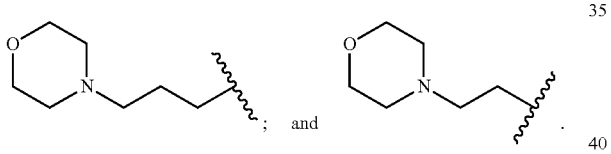

wherein $R^A$, $R^B$, $R^C$, $R^D$, and $R^E$ are as defined above.

In certain embodiments, the compound of formula (I) has formula (I-iv), or a salt thereof,

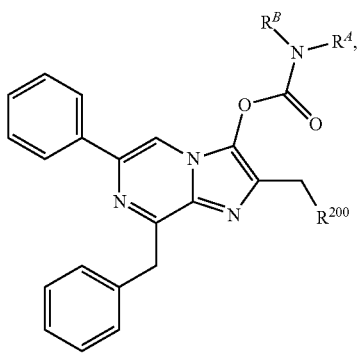

wherein $R^{200}$ is aryl or heteroaryl, each optionally substituted with 1, 2, or 3 substituents independently selected from the group consisting of halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino; and $R^A$, and $R^B$ are as defined above.

In certain embodiments, the compound of formula (I) has formula (I-x), or a salt thereof,

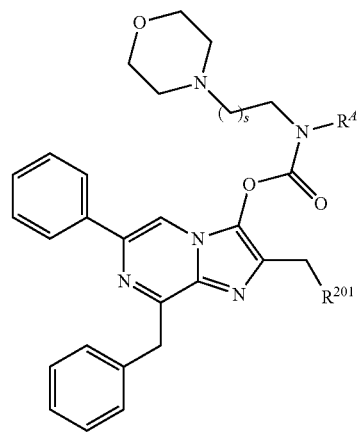

wherein s is 1 or 2;

$R^{201}$ is aryl or heteroaryl, each optionally substituted with 1, 2, or 3 substituents independently selected from the group consisting of halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino; and $R^A$ is as defined above.

In certain embodiments, the compound of formula (I) has formula (I-xvii), or a salt thereof, (I-xvii)

wherein q is 1 or 2; s is 1 or 2; and R⁴ is as defined above.

In certain embodiments, a compound of the invention is selected from the group consisting of:

PBI-5295

PBI-5296

PBI-5393

PBI-5394

PBI-5396

PBI-5442
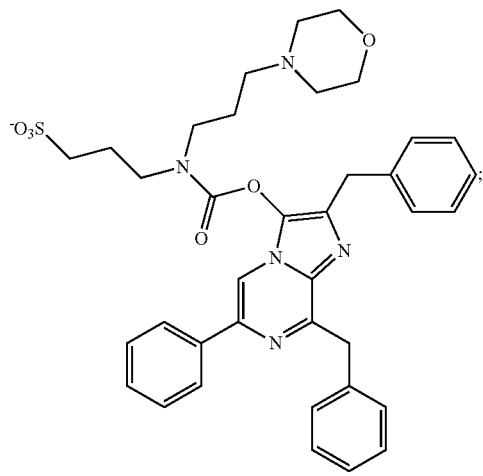
PBI-5457
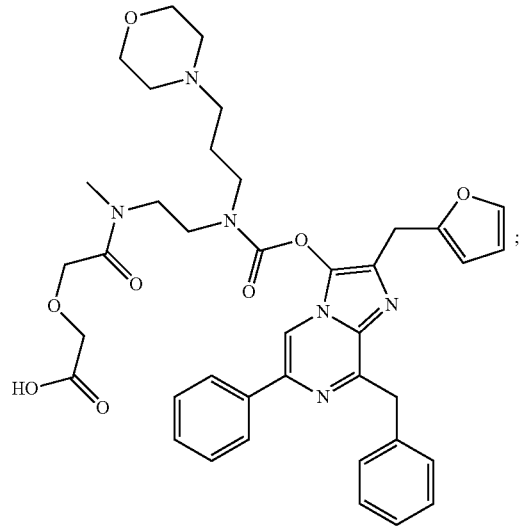
PBI-5455
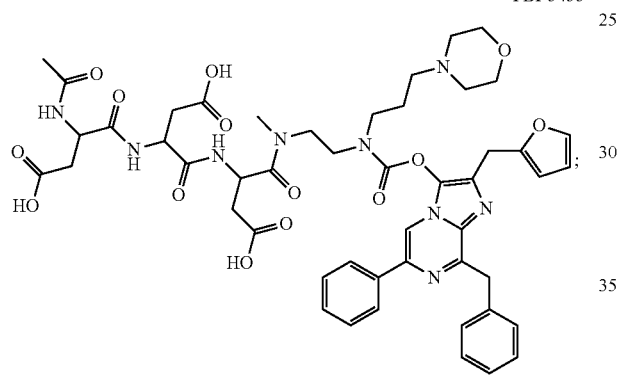
PBI-5456
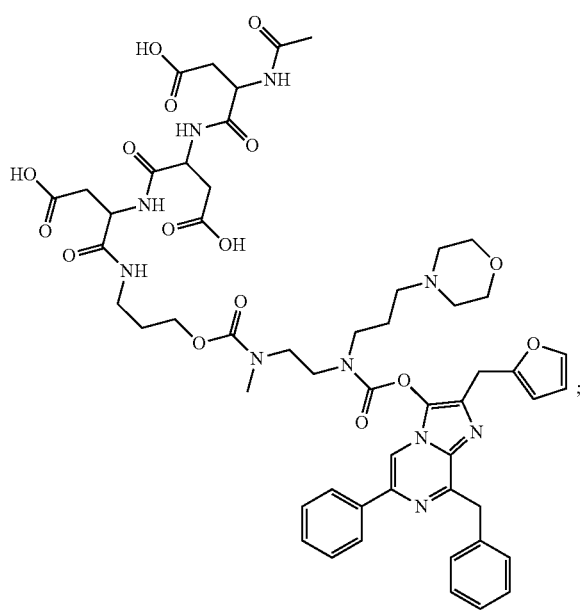
PBI-5488
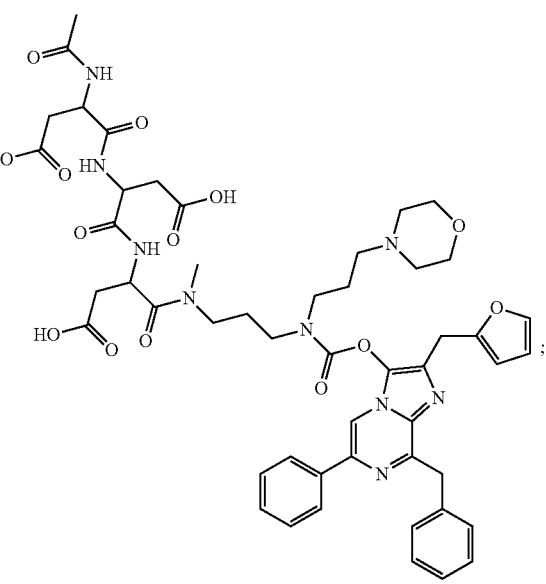

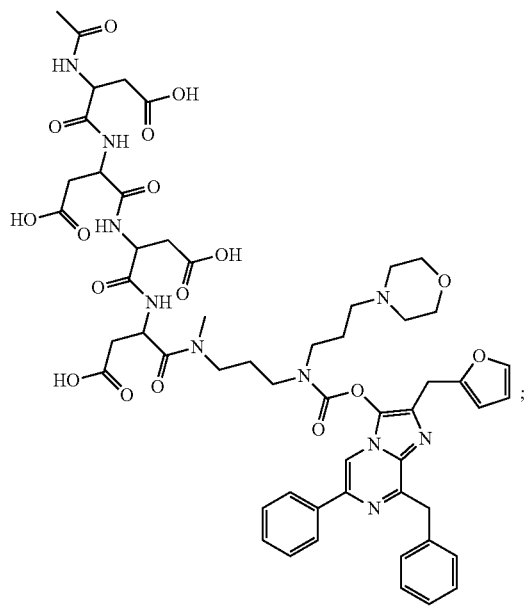
PBI-5489
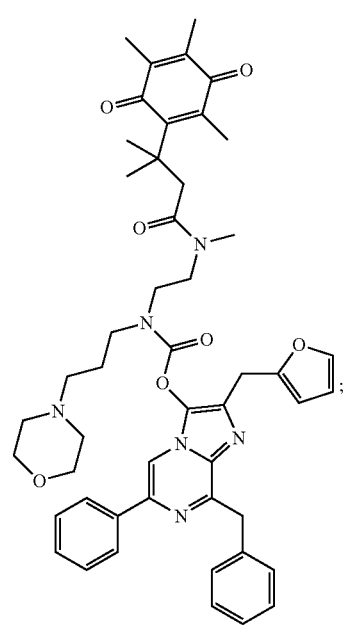
PBI-5370
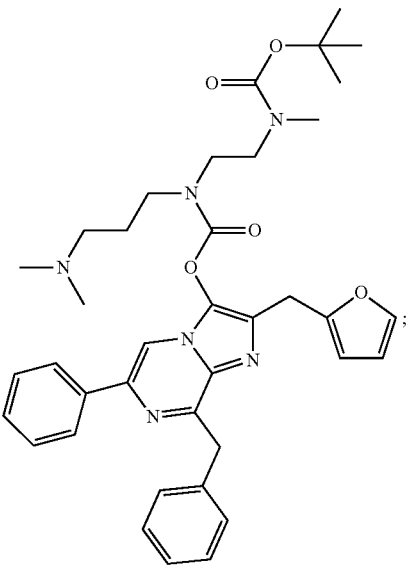
PBI-5545
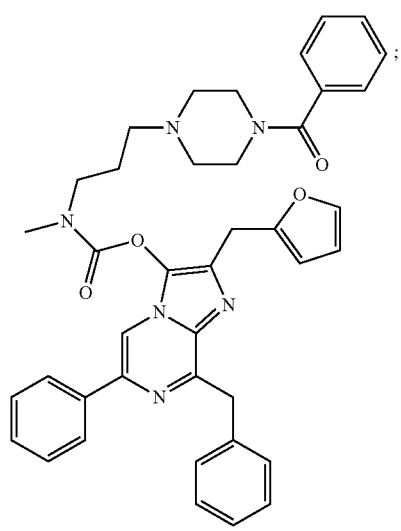
PBI-5422
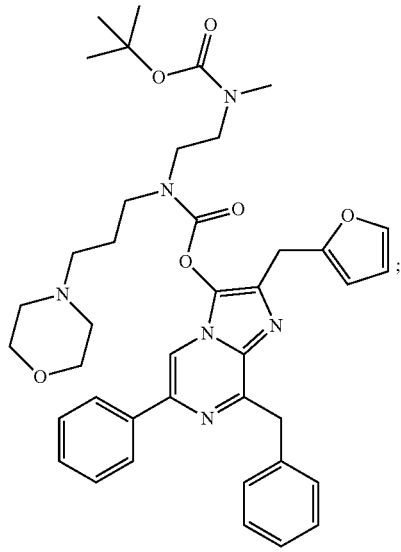
PBI-5416

PBI-5417
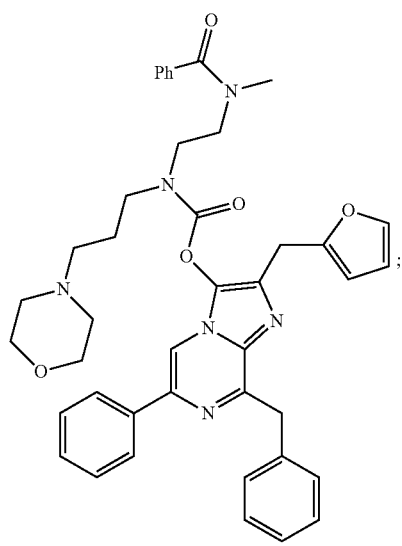
PBI-5453
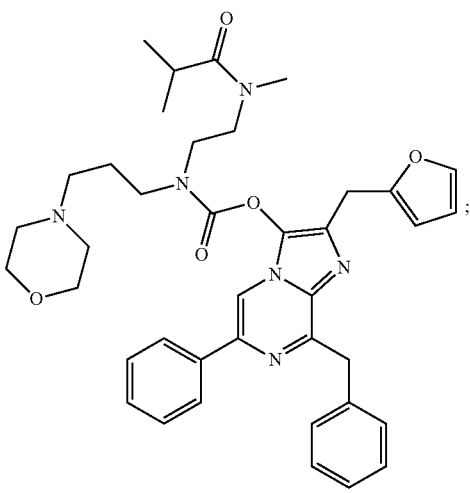
PBI-5418
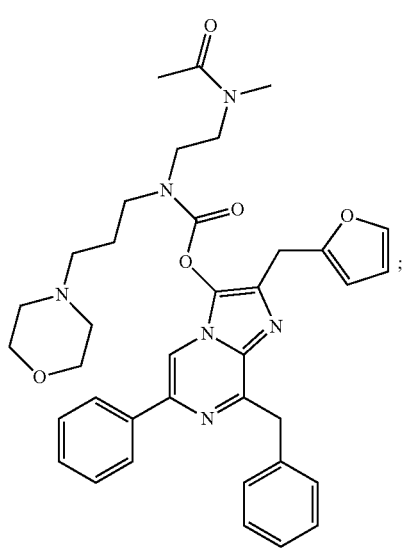
PBI-5450
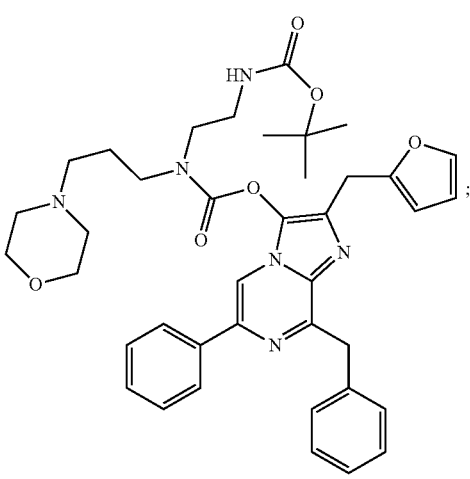
PBI-5452
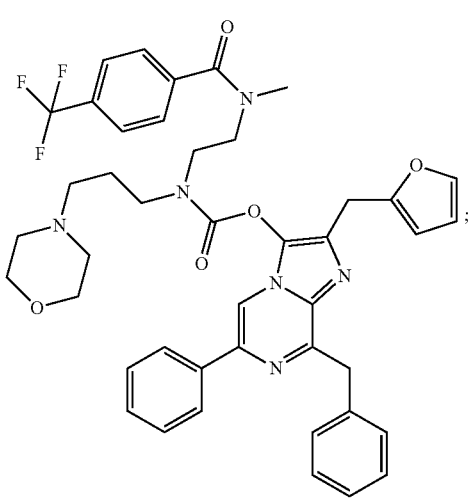
PBI-5451
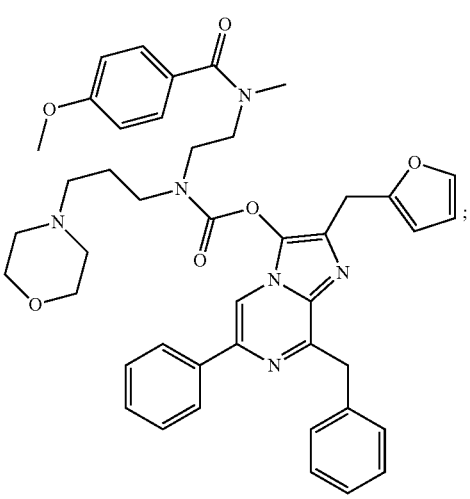

PBI-5454
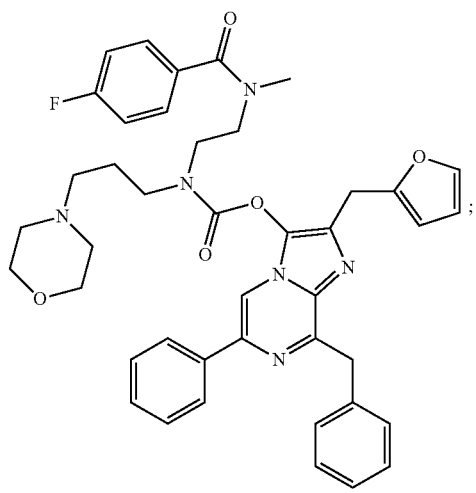
PBI-5546
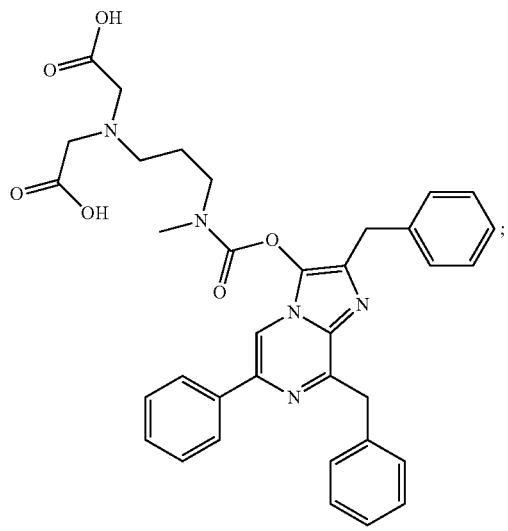
PBI-5512
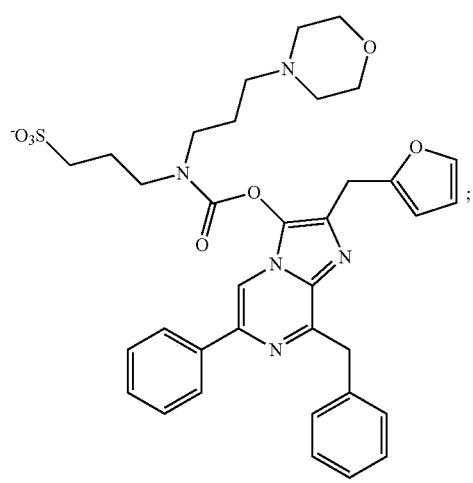
PBI-5486
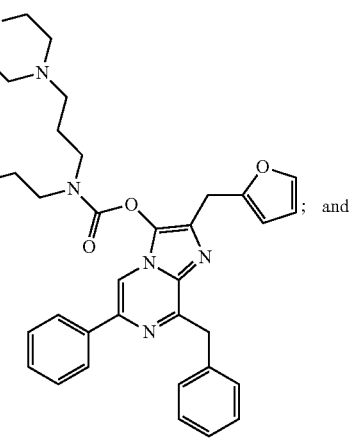
;  and
PBI-5547
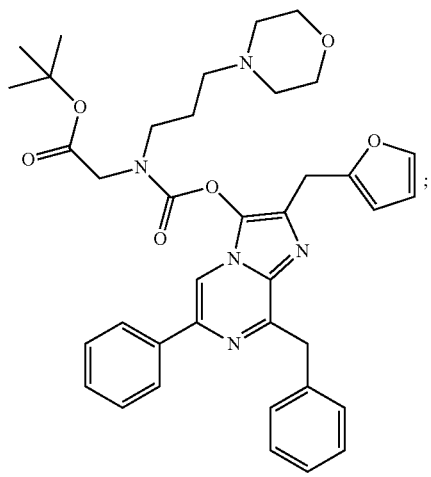
PBI-5487
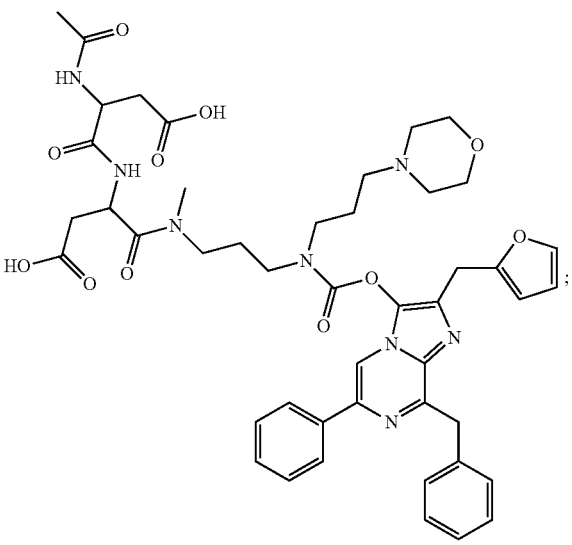
or a salt thereof.
In another aspect, disclosed are compositions comprising a pro-substrate compound of the invention and a corresponding cell permeable substrate. Such a mixture can provide higher light intensity at earlier time points before there is significant accumulation of free substrate from the carbamate protected precursor. In certain embodiments, disclosed are compositions comprising a mixture of a compound of the invention and at least one compound of formula (II),

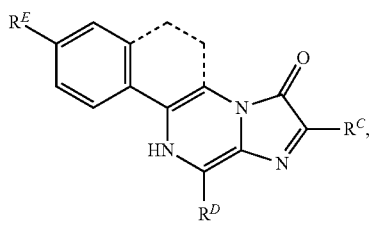
(II)

wherein $R^C$, $R^D$, and $R^E$ are as defined above.

In certain embodiments, the compound of formula (II) is selected from the group consisting of (II-i), (II-ii), (II-iii), (II-iv), and (II-v), or a combination thereof,

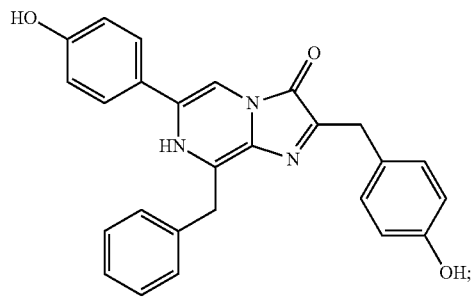
Coelenterazine
(II-i)

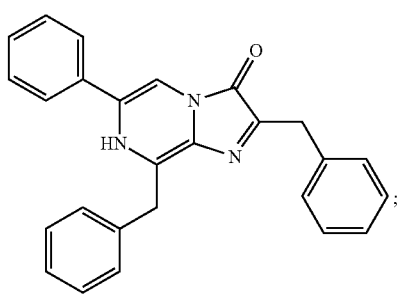
Coelenterazine-hh
(II-ii)

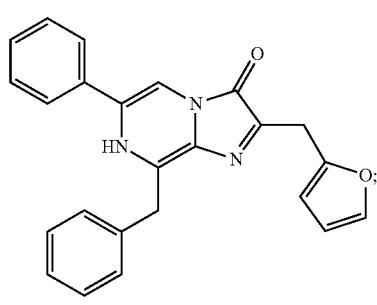
Furimazine
(II-iii)

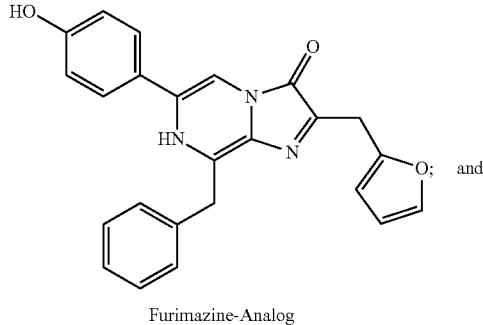
Furimazine-Analog
(II-iv)

and

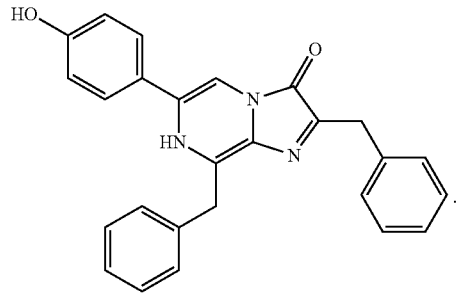
Coelenterazine-h
(II-v)

In some aspects, disclosed are methods for detecting the presence of a luciferase in a sample, the methods comprising: a) contacting the sample with a compound of the invention; and b) detecting luminescence in the sample, whereby the detection of luminescence indicates the presence of a luciferase. In certain embodiments, the sample comprises cells. In some embodiments, the sample comprises live cells. In certain embodiments, the cells comprise luciferase. In some embodiments, the cells comprise an *Ophlophorus* luciferase. In some embodiments, the luciferase is a variant of an *Ophlophorus* luciferase. In certain embodiments, step a) further comprises contacting the sample with a nucleophile configured to react with a compound of formula (I) to provide a cell permeable substrate. The cell permeable substrate may be a compound of formula (II), as defined above. The cell permeable substrate may be a compound of formula (II-i), (II-ii), (II-iii), (II-iv), or (II-v), or a combination thereof, as defined above.

In some aspects, disclosed are methods for measuring the activity of a promoter operably linked to a gene encoding a luciferase, the methods comprising a) obtaining a sample comprising the promoter operably linked to the gene encoding a luciferase; b) contacting the sample with a compound of the invention; and c) determining the activity of the promoter by measuring luminescence of the reaction mixture. In certain embodiments, the sample comprises cells. In some embodiments, the sample comprises live cells. In certain embodiments, the cells comprise luciferase. In some embodiments, the luciferase is an *Opholphorus* luciferase. In some embodiments, the luciferase is a variant of an *Ophlophorus* luciferase. In certain embodiments, step a) further comprises contacting the sample with a nucleophile configured to react with a compound of formula (I) to provide a cell permeable substrate. The cell permeable substrate may be a compound of formula (II), as defined above. The cell permeable substrate may be a compound of formula (II-i), (II-ii), (II-iii), (II-iv), or (II-v), or a combination thereof, as defined above.

In the disclosed methods, the compound of the invention used in the methods may be in a buffered solution. The compound may be at least partially hydrolyzed to release a cell permeable substrate prior to contact with a sample. The buffered solution may have a pH (e.g., 6-10) that tunes or facilitates self-based catalysis of the compound to release the cell permeable substrate. The buffered solution may include a nucleophilic compound or solution, wherein the nucleophile (e.g., a thiol, an amine, or an alkylamine) may be configured to react with the compound of the invention to release a cell permeable substrate. The nucleophile or nucleophilic solution may tune or facilitate self-based catalysis of the compound of the invention. The buffered solution may include a non-luminescent enzyme (e.g., a phosphatase, a protease, an esterase, or a sulfatase) that cleaves the cell impermeable moiety of the compound of the invention.

In some aspects, disclosed are methods to detect an interaction between a first protein and a second protein in a sample, the methods comprising: (a) contacting a sample with a compound of the invention; and (b) detecting luminescence in the sample, wherein the detection of luminescence indicates an interaction between the first protein and the second protein. The sample may include (i) a first polynucleotide encoding a first fusion protein, wherein the first fusion protein comprises a first fragment of a luminescent enzyme and a first protein; and (ii) a second polynucleotide encoding a second fusion protein, wherein the second fusion protein comprises a second fragment of the luminescent enzyme and a second protein. The compound of the invention may be at least partially hydrolyzed to release a cell permeable substrate. When the first protein and second protein interact, the first fragment of the luminescent enzyme and the second fragment of the luminescent enzyme may reconstitute a full-length enzyme capable of stably binding the cell-permeable substrate. In certain embodiments, the sample comprises cells. In some embodiments, the sample comprises live cells. In certain embodiments, the cells comprise a luminescent enzyme, such as a coelenterazine-utilizing luciferase enzyme. The coelenterazine-utilizing enzyme may be an *Oplophorus* luciferase enzyme or a variant or mutant thereof.

In some aspects, disclosed are methods to detect an interaction between a first protein and a second protein in a sample, the methods comprising: (a) contacting a sample with the compound a compound of the invention; and (b) detecting bioluminescence resonance energy transfer (BRET) in the sample, indicating an interaction or close proximity of the bioluminescent donor and the fluorescence acceptor. The sample may include (i) a first polynucleotide encoding a first fusion protein, wherein the first fusion protein comprises a luminescent enzyme and a first protein; and (ii) a second polynucleotide encoding a second fusion protein, wherein the second fusion protein comprises a fluorescent acceptor molecule and a second protein. In certain embodiments, the sample comprises cells. In some embodiments, the sample comprises live cells. In certain embodiments, the cells comprise a luminescent enzyme, such as a coelenterazine-utilizing luciferase enzyme. The coelenterazine-utilizing enzyme may be an *Oplophorus* luciferase enzyme or a variant or mutant thereof.

In some aspects, disclosed are bioluminescence resonance energy transfer (BRET) systems including: a first fusion protein including a first target protein and a bioluminescence donor molecule, wherein the bioluminescence donor molecule is a luminescent enzyme; a second fusion protein including a second target protein and a fluorescent acceptor molecule; and a compound of the invention.

In some aspects, disclosed are methods of detecting an enzyme in a sample, the methods comprising, (a) contacting the sample with a compound selected from the group consisting of a compound of formula (I), a compound of formula (a), a compound of formula (b), a compound of formula (c), a compound of formula (d), and any combination thereof,

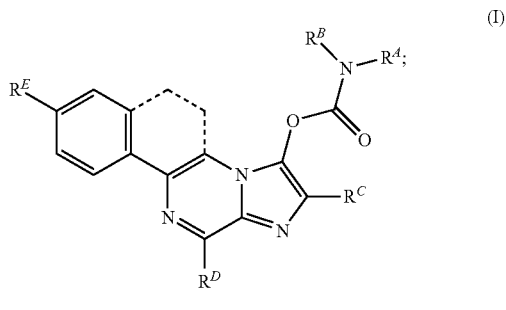

(I)

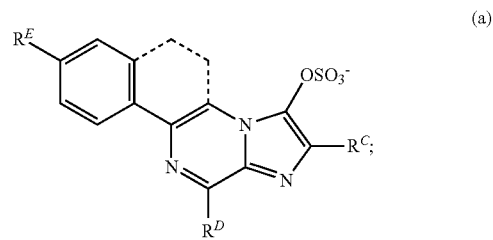

(a)

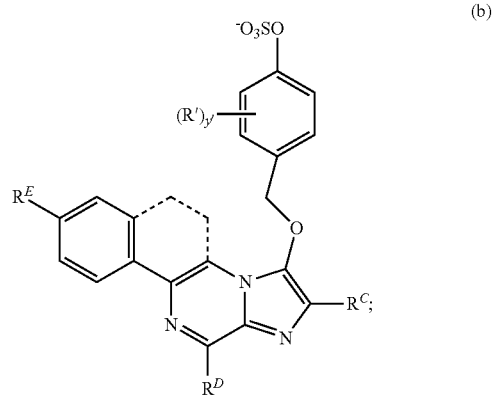

(b)

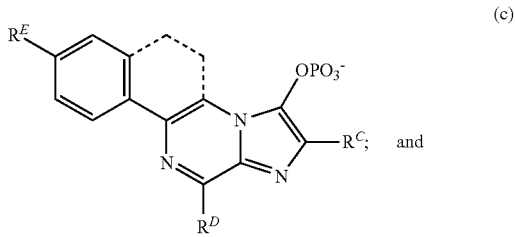

(c) and

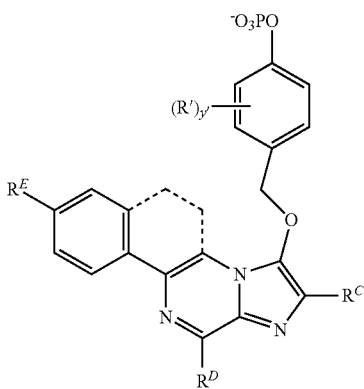

(d)

wherein R' is, at each occurrence, independently selected from the group consisting of halogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino; y' is 0, 1, 2, 3, or 4; and $R^A$, $R^B$, $R^C$, $R^D$, and $R^E$ are as defined above; and (b) detecting luminescence in the sample, wherein the compound of formula (I), the compound of formula (a), the compound of formula (b), the compound of formula (c), the compound of formula (d), or the combination thereof is converted to one or more cell permeable substrates through reaction with a non-luminescent enzyme. The non-luminescent enzyme may be a phosphatase, a protease, an esterase, or a sulfatase.

In some aspects, disclosed are kits including a compound of the invention.

The compounds, compositions, methods, and processes are further described herein.

DETAILED DESCRIPTION

Figure 1:
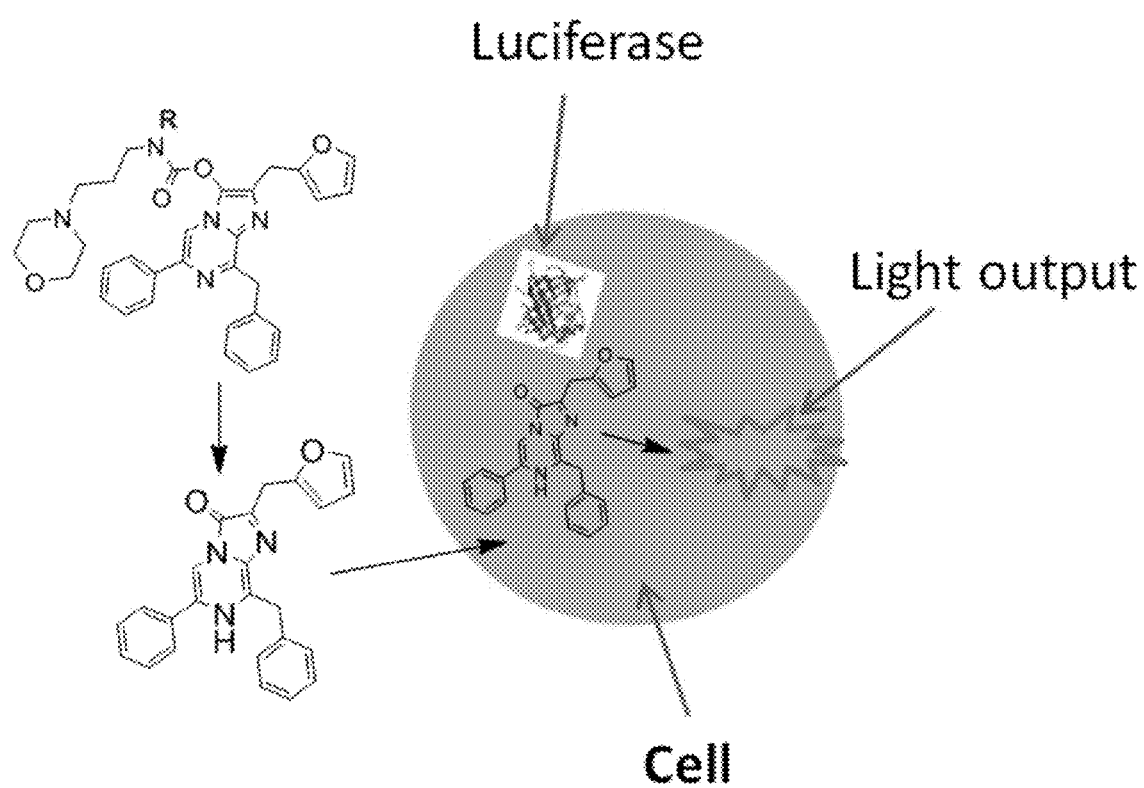
FIG. 1 depicts a schematic of a pro-substrate as disclosed herein being converted to a cell permeable substrate exogenous to a cellular membrane, the cell permeable substrate permeating the cell membrane, and the cell permeable substrate being acting on by a luciferase.

Disclosed herein are cell-impermeable pro-substrates. The pro-substrates can be used to measure luminescent enzymes in living cells. Traditional methods for providing substrates to intracellular enzymes have relied on cell permeable pro-substrates that are converted to substrates through the activity of endogenous esterases, reductases or proteases. The approach described here may utilize cell impermeable pro-substrates that provide a sustained release of cell permeable substrate (e.g., coelenterazine, or derivative or analogue thereof, such as furimazine) upon hydrolysis. The cell impermeable substrates may be masked by highly functionalized carbamates that contain an amine base (or nucleophile) and, optionally, one or more charged functional groups. Hydrolysis of the carbamate may be tuned by choice of the appropriate internal base. The internal base and the optional introduced negative charge(s) may maximize substrate solubility and minimize cell permeability. When the protected cell impermeable pro-substrate is added to the cells, it may be deprotected (become cell permeable) by a reaction in the extracellular medium ("self-based catalyzed"), and the substrate (deprotected) may freely diffuse into the cell where it may be utilized by a luminescent enzyme.

The advantages of the disclosed compounds, compositions, and methods include: increased signal stability versus use of unprotected coelenterazine, or derivative or analogue thereof, for kinetic experiments; significant increases in signal intensity versus use of coelenterazine, or derivative or analogue thereof, protected using more traditional approaches; increased solubility versus unprotected coelenterazine, or derivative or analogue thereof, or coelenterazine, or derivative or analogue thereof, protected using more traditional approaches; and decreased cytotoxicity versus unprotected coelenterazine, or derivative or analogue thereof, or coelenterazine, or derivative or analogue thereof, protected using more traditional approaches. As a result of these properties, the disclosed compounds can be used in applications that include reporter gene assays, BRET and protein complementation.

1. DEFINITION OF TERMS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

As used herein, the term "suitable substituent" is intended to mean a chemically acceptable functional group e.g., a moiety that does not negate the activity of the inventive compounds. Illustrative examples of suitable substituents include, but are not limited to halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents.

As used herein, the term "alkenyl" refers a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyl groups of the present invention may be unsubstituted or substituted by one or more suitable substituents, preferably 1 to 3 suitable substituents, as defined above.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkoxyalkoxy" refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

As used herein, the term "alkoxyalkyl" refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

As used herein, the term "alkoxycarbonyl" refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

As used herein, the term "alkyl" refers to a linear or branched hydrocarbon radical, preferably having 1 to 30 carbon atoms, 1 to 10 carbon atoms, 1 to 6 carbon atoms or 1 to 4 carbon atoms. The term "$C_1$-$C_6$-alkyl" is defined to include alkyl groups having 1, 2, 3, 4, 5 or 6 carbons in a linear or branched arrangement. For example, "$C_1$-$C_6$-alkyl" specifically includes methyl, ethyl, n-propyl, i-propyl, n-butyl, t-butyl, i-butyl, pentyl and hexyl. Alkyl groups of the present invention may be unsubstituted or substituted by one or more suitable substituents, preferably 1 to 3 suitable substituents, as defined above.

As used herein, the term "alkylamino" refers to an alkyl group, as defined herein, appended to the parent molecular moiety through an amino group, as defined herein. Representative examples of alkylamino include, but are not limited to, methylamino, ethylamino, and sec-butylamino As used herein, the term "alkylaminoalkyl" refers to an alkyl group, as defined herein, appended to the parent molecular moiety through an aminoalkyl group, as defined herein. Representative examples of alkylaminoalkyl groups include, but are not limited to, methylaminoethyl and methylamino-2-propyl.

As used herein, the term "alkylcarbonyl" refers to an alkyl group appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

As used herein, the term "alkylcarbonylalkoxy" refers to an alkylcarbonyl group, as defined herein, appended to the parent molecular moiety through an alkoxy group, as defined herein. Representative examples of alkylcarbonylalkoxy include, but are not limited to, 3-oxopentyloxy, 3-oxobutoxy and 2-oxopropoxy.

As used herein, the term "alkylcarbonylalkoxyalkyl" refers to an alkylcarbonylalkoxy group, as defined herein, appended to the parent molecular moiety through an alkyl group.

As used herein, the term "alkylcarbonyloxy" refers to an alkylcarbonyl group, as defined herein, appended to the parent molecular moiety through an oxygen atom. Representative examples of alkylcarbonyloxy include, but are not limited to, acetyloxy, ethylcarbonyloxy and tert-butylcarbonyloxy.

As used herein, the term "alkynyl" refers to a straight or branched hydrocarbon radical having 2, 3, 4, 5, 6, 7, 8, 9 or 10 carbons and having one or more carbon-carbon triple bonds. Alkynyl groups of the present invention include, but are not limited to, ethynyl, propynyl and butynyl. Alkynyl groups of the present invention may be unsubstituted or substituted by one or more suitable substituents, preferably 1 to 3 suitable substituents, as defined above.

As used herein, the term "amino" refers to an —NH$_2$ group.

As used herein, the term "amino acid" refers to both natural and unnatural amino acids. It also includes protected natural and unnatural amino acids.

As used herein, the term "aminoalkyl" refers to at least one amino group, as defined herein, appended to the parent molecular moiety through an alkyl group, as defined herein. Representative examples of aminoalkyl include, but are not limited to, aminomethyl, 2-aminoethyl and 2-aminopropyl.

As used herein, the term "aryl" means monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups of the present invention may be optionally substituted by one or more suitable substituents, preferably 1 to 5 suitable substituents, as defined above.

As used herein, the term "arylalkyl" refers to an aryl group, as defined herein, appended to the parent molecular moiety through an alkyl group, as defined herein. Representative examples of arylalkyl include, but are not limited to, phenylmethyl and phenylethyl.

As used herein, the term "arylcarbonyl" refers to an aryl group, as defined herein, appended to the parent molecular moiety through a carbonyl group, as defined herein.

As use herein, the term "azide" refers to an —N=N$^+$=N$^-$(—N$_3$) group.

As used herein, the term "azidealkyl" refers to an azide group, as defined herein, appended to the parent molecular moiety through an alkyl group, as defined herein. Representative examples of azidealkyl include, but are not limited to, azidemethyl and azideethyl.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxyl (C=O)—NH—) refers to an alkyl carbamate group. The carbonyl group is also equivalently defined herein as (C=O). Alkylcarbonylamino refers to groups such as acetamide.

As used herein, the term "carboxy" refers to a —C(O)—OH group.

As used herein, the term "carboxyalkoxyalkyl" refers to -alkyl-O-alkyl-CO$_2$H.

As used herein, the term "carboxyalkyl" refers to a carboxy group as defined herein, appended to the parent molecular moiety through an alkyl group as defined herein.

As used herein, the term "cell impermeable" refers to a compound or moiety that is not cell membrane permeable to the extent that an effective amount of the compound is intracellularly delivered.

As used herein, the term "cell permeable" refers to a compound or moiety that is cell membrane permeable to the extent that an effective amount of the compound is intracellularly delivered.

As used herein, the term "cycloalkyl" refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups of the present invention may be unsubstituted or substituted by one or more suitable substituents, preferably 1 to 5 suitable substituents, as defined above.

As used herein, the term "di(alkyl)amino" refers to two independently selected alkyl groups, as defined herein, appended to the parent molecular moiety through an amino group, as defined herein. Representative examples of di(alkyl)amino include, but are not limited to, N,N-dimethylamino, N-ethyl-N-methylamino, and N-isopropyl-N-methylamino As used herein, the term "di(alkyl)aminoalkyl" refers to a di(alkyl)amino group, as defined herein, appended to the parent molecular moiety through an alkyl group, as defined herein. Representative examples of di(alkyl)aminoalkyl include, but are not limited to, N,N-dimethylaminoethyl and N,N-methyl(2-propyl)aminoethyl.

As used herein, the term "halogen" or "halo" refers to a fluoro, chloro, bromo or iodo radical.

As used herein, the term "haloalkoxy" refers to an alkoxy group, as defined herein, substituted by one, two, three, or four halogen atoms. Representative examples of haloalkoxy include, but are not limited to, chloromethoxy, 2-fluoroethoxy, trifluoromethoxy, and pentafluoroethoxy.

As used herein, the term "haloalkyl" refers to an alkyl group, as defined herein, substituted by one, two, three, or four halogen atoms. Representative examples of haloalkyl include, but are not limited to, chloromethyl, 2-fluoroethyl, trifluoromethyl, pentafluoroethyl, 2-chloro-3-fluoropentyl, and 4,4,4,-trifluorobutyl.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. Heteroaryl groups of the present invention may be unsubstituted or substituted by one or more suitable substituents, preferably 1 to 5 suitable substituents, as defined above.

As used herein, the term "heterocycle" or "heterocyclyl" refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur.

The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.13,7]decane. Heterocyclic groups of the present invention may be unsubstituted or substituted by one or more suitable substituents, preferably 1 to 3 suitable substituents, as defined above.

As used herein, the term "hydroxy" refers to an —OH group.

As used herein, the term "hydroxyalkoxy" refers to an alkoxy group, as defined herein, substituted by at least one hydroxy group. Representative examples of hydroxyalkoxy include, but are not limited to, hydroxyethoxy, and 2-hydroxypropoxy.

As used herein, the term "hydroxyalkyl" refers to an alkyl group, as defined herein, substituted by at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

As used herein, the term "hydroxycarbonyl" refers to a hydroxy group, as defined herein, appended to the parent molecular moiety through a carbonyl group, as defined herein.

The term "linker" may refer to a chain of 2 to 50 atoms that link a substrate moiety to the parent molecular moiety. Linkers may include one or more heteroatoms. Linkers may also be substituted by oxo groups, amino groups, alkyl groups, halogens and nitro groups. Linkers may also contain aryl groups. The linkers may be "traceless" or "self-immolative" linkers. The term "traceless linker" or "self-immolative linker" refers to a linker wherein cleavage of the substrate moiety from the linker results in spontaneous cleavage of the linker from the parent molecular moiety.

The term "lower cycloalkyl" refers to a monovalent moiety obtained by removing a hydrogen atom from a hydrocarbon compound having from 3 to 6 carbon atoms. Examples of saturated lower cycloalkyl groups include, but are not limited to, groups such as cyclopropyl, cyclobutyl, cyclopentyl and cyclohexyl. Examples of unsaturated lower cylcoalkyl groups which have one or more carbon-carbon double bonds include, but are not limited to, groups such as cyclopropenyl, cyclobutenyl, cyclopentenyl and cyclohexenyl.

The term "luminescent enzyme" unless specified otherwise, refers to a naturally occurring, recombinant or mutant luminescent enzyme that uses a coelenterazine and/or a coelenterzaine derivative or analogue thereof, as a substrate. The luminescent enzyme, if naturally occurring, may be obtained easily by the skilled person from an organism. If the luminescent enzyme is one that occurs naturally or is a recombinant or mutant luminescent enzyme, i.e. one which retains activity in a luciferase-coelenterazine reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods, such as from the Oplophoroidea, e.g. *Oplophorus*-derived luciferases, marine organisms such as cnidarians (e.g., *Renilla* luciferase), Aristeidae, Solenoceridae, Luciferidae, Sergestidae, Pasipheidae and Thalassocarididae decapoda families, and photoproteins, such as *Aequorin*, and variants and mutants of said luciferases.

A "luminescent reaction mixture" contains materials that will allow the luminescent enzyme to generate a light signal, i.e., luminescence. The mixture may also contain the enzyme. The materials needed, and the particular concentrations and/or amounts, of the materials needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

As used herein, the term "methylenedioxy" refers to a —OCH$_2$O— group wherein the oxygen atoms of the methylenedioxy are attached to the parent molecular moiety through two adjacent carbon atoms.

As used herein, the term "nitrogen protecting group" refers to groups intended to protect an amino group against undesirable reactions during synthetic procedures. Representative nitrogen protecting groups include acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

As used herein, the term "oxo" refers to a double bonded oxygen (=O) radical wherein the bond partner is a carbon atom. Such a radical can also be thought as a carbonyl group.

The term "peptide" or "polypeptide" refers to a sequence of at least two amino acids. In some embodiments, a peptide may contain no more than 80 amino acids, or no more than 35 amino acids, or no more than 10 amino acids.

The term "saccharide" refers to a sugar or other carbohydrate, especially a simple sugar. It includes both the alpha- and the beta-anomers. The saccharide can be a $C_6$-polyhydroxy compound, typically a $C_6$-pentahydroxy, and often a cyclic glycal. It includes the known simple sugars and their derivatives, as well as polysaccharides with two or more monosaccharide residues. The saccharide can include protecting groups on the hydroxyl groups. The hydroxyl groups of the saccharide can be replaced with one or more acetamido, halo or amino groups. Additionally, one or more of the carbon atoms can be oxidized, for example to keto or carbonyl groups. Suitable saccharides include galactose, glucose, glucoronic acid and neurominic acid.

As used herein, the term "sulfonyl" refers to an $>S(O)_2$ group.

A prefix attached to a multi-component substituent only applies to the first component it precedes. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If the halogen substitution may only occur on the alkyl component, the substituent would instead be described as "alkoxyhaloalkyl."

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

When a substituent is referred to as "unsubstituted" or not referred to as "substituted" or "optionally substituted", it means that the substituent does not have any substituents. If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

If substituents are described as being "independently selected" from a group, each substituent is selected independent of the other. Each substituent, therefore, may be identical to or different from the other substituent(s).

2. CELL IMPERMEABLE PRO-SUBSTRATES

Compounds of the invention include cell impermeable pro-substrates. The pro-substrates can be used in methods of detecting the presence/absence and/or activity of enzymes in living cells. The cell impermeable pro-substrates may provide a sustained release of cell permeable substrate. The cell impermeable pro-substrates may be converted to a cell permeable substrate by an intramolecular reaction and/or by an intermolecular reaction. The cell impermeable pro-substrates may be in a buffered solution. The cell impermeable pro-substrates may comprise a functional group (e.g., a basic functional group) configured to cleave the cell impermeable moiety of the pro-substrate (e.g., via nucleophilic addition reaction and/or via catalysis of a nucleophilic addition reaction, such as a hydrolysis reaction). The functional group may cleave a cell impermeable moiety via an intramolecular reaction within the same molecule and/or by intermolecular reaction acting on a different pro-substrate molecule. Upon entering the cell, the cell permeable substrate may be acted on by an enzyme such as luciferase. The disclosed pro-substrates may consequently be useful in methods of detecting enzymes.

a. Compounds

In certain embodiments, compounds of the invention have formula (I), or a salt thereof,

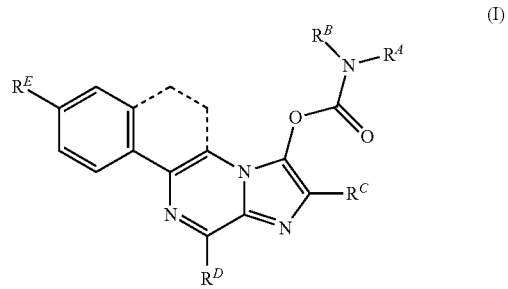

wherein, $R^A$ is a cell impermeable moiety;

$R^B$ is a moiety comprising a functional group configured to react with the carbonyl group of —OC(O)NR$^A$R$^B$ (e.g., the functional group may catalyze nucleophilic addition to the carbonyl group of —OC(O)NR$^A$R$^B$ and/or the functional group may undergo a nucleophilic addition reaction with the carbonyl group of —OC(O)NR$^A$R$^B$);

R$^C$ is alkyl, aryl, heteroaryl, heterocyclyl, cycloalkyl, arylalkyl, heteroarylalkyl, heterocyclylalkyl, or cycloalkylalkyl, wherein said aryl, heteroaryl, heterocyclyl, cycloalkyl, arylalkyl, heteroarylalkyl, heterocyclylalkyl, and cycloalkylalkyl are each independently unsubstituted or substituted with one or more suitable substituents;

R$^D$ is hydrogen, alkyl, arylalkyl, cycloalkyl, or cycloalkylalkyl;

R$^E$ is hydrogen, hydroxy, alkoxy, amino, alkylamino, di(alkyl)amino, —OC(O)alkyl, or —OCH$_2$OC(O)alkyl;

wherein the dash bonds together indicate the presence of an optional 6-membered ring in the compound of formula (I), wherein the optional ring is saturated or unsaturated.

In certain embodiments, R$^A$ is a cell impermeable moiety comprising an amino acid, a peptide, or a saccharide. In certain embodiments, R$^A$ is a cell impermeable moiety comprising a polypeptide or a polysaccharide. In certain embodiments, R$^B$ is a moiety comprising a morpholinyl group. In certain embodiments, R$^B$ is a morpholinylalkyl.

In certain embodiments, compounds of the invention have formula (I), or a salt thereof,

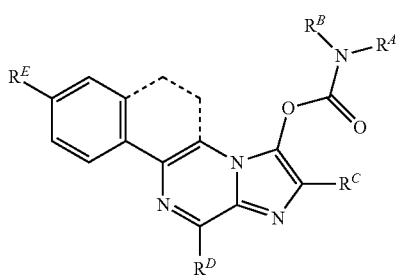

wherein,

R$^A$ is selected from the group consisting of alkyl, alkoxy, alkenyl, alkynyl, aryl, heteroaryl, heterocyclyl, and cycloalkyl, wherein said alkyl, alkoxy, alkenyl, alkynyl, aryl, heteroaryl, heterocyclyl, and cycloalkyl are each independently unsubstituted or substituted with one or more suitable substituents;

R$^B$ is aminoalkyl or thioalkyl, wherein said alkyl is unsubstituted or substituted with one or more suitable substituents, and wherein said amino of the aminoalkyl is unsubstituted or substituted with one or more suitable substituents, or wherein the nitrogen atom of the aminoalkyl forms part of a heterocyclic group, wherein said heterocyclic group is unsubstituted or substituted with one or more suitable substituents;

R$^C$ is alkyl, aryl, heteroaryl, heterocyclyl, cycloalkyl, arylalkyl, heteroarylalkyl, heterocyclylalkyl, or cycloalkylalkyl, wherein said aryl, heteroaryl, heterocyclyl, cycloalkyl, arylalkyl, heteroarylalkyl, heterocyclylalkyl, and cycloalkylalkyl are each independently unsubstituted or substituted with one or more suitable substituents;

R$^D$ is hydrogen, alkyl, arylalkyl, cycloalkyl, cycloalkylalkyl; and

R$^E$ is hydrogen, hydroxy, alkoxy, amino, alkylamino, di(alkyl)amino, —OC(O)alkyl, or —OCH$_2$OC(O)alkyl;

wherein the dash bonds together indicate the presence of an optional 6-membered ring in the compound of formula (I), wherein the optional ring is saturated or unsaturated.

In certain embodiments, compounds of the invention have formula (I), or a salt thereof,

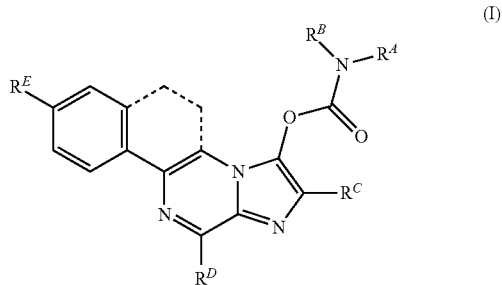

wherein,

R$^A$ is selected from the group consisting of alkyl, alkoxyalkyl, haloalkyl, haloalkoxyalkyl, hydroxyalkyl, aminoalkyl, alkylaminoalkyl, di(alkyl)aminoalkkyl, tetraalkylammoniumalkyl, pyridiniumalkyl, azidoalkyl, cyanoalkyl, maleimidoalkyl, alkoxy, haloalkoxy, alkoxyalkoxy, alkenyl, alkynyl, —(CR$^1$R$^2$)$_m$—N(R$^3$)C(O)R$^4$, —(CR$^5$R$^6$)$_m$—SO$_3$R$^7$, —(CR$^5$R$^6$)$_m$—OPO$_2$R$^7$, —(CR$^5$R$^6$)$_m$—SO$_2$N(R$^8$)(R$^9$), —(CR$^{10}$R$^{11}$)$_m$—CO$_2$R$^{12}$, —(CR$^{13}$R$^{14}$)$_m$—CON(R$^{15}$)(R$^{16}$), —(CR$^{17}$R$^{18}$)$_m$—ON(R$^{19}$)(R$^{20}$), —(CR$^{21}$R$^{22}$)$_m$-heterocyclyl-(CR$^{23}$R$^{24}$)$_n$—R$^{25}$, —(CR$^{26}$R$^{27}$)$_m$-heteroaryl-(CR$^{28}$R$^{29}$)$_n$—R$^{30}$, —(CR$^{31}$R$^{32}$)$_m$-aryl-(CR$^{33}$R$^{34}$)$_n$—R$^{35}$, and —(CR$^{36}$R$^{37}$)$_m$-cycloalkyl-(CR$^{38}$R$^{39}$)$_n$—R$^{40}$;

R$^1$, R$^2$, R$^3$, R$^5$, R$^6$, R$^8$, R$^{10}$, R$^{11}$, R$^{13}$, R$^{14}$, R$^{15}$, R$^{17}$, R$^{18}$, R$^{19}$, R$^{21}$, R$^{22}$, R$^{23}$, R$^{24}$, R$^{26}$, R$^{27}$, R$^{28}$, R$^{29}$, R$^{31}$, R$^{32}$, R$^{33}$, R$^{34}$, R$^{36}$, R$^{37}$, R$^{38}$, and R$^{39}$ are each independently selected from the group consisting of hydrogen and alkyl;

R$^4$, R$^7$, R$^9$, R$^{12}$, R$^{16}$, R$^{20}$, R$^{25}$, R$^{30}$, R$^{35}$, and R$^{40}$ are each independently selected from the group consisting of hydrogen, alkyl, alkoxy, alkylcarbonyl, alkylcarbonylalkoxylalkyl, alkylcarbonyloxyalkyl, alkoxycarbonylalkyl, hydroxy(mono or polyalkoxy)alkyl, carboxyalkyl, carboxyalkoxyalkyl, suflonate alkyl, tetraalkylammoniumalkyl, pyridiniumalkyl, aryl, heteroaryl, heterocyclyl, cycloalkyl, arylalkyl, heteroarylalkyl, heterocyclylalkyl, cycloalkylalkyl,

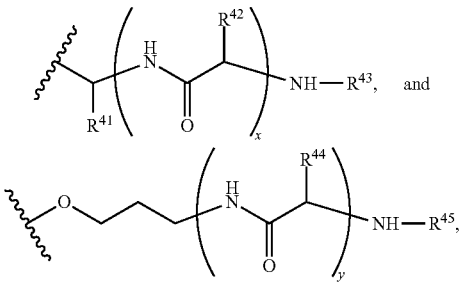

wherein said aryl, heteroaryl, heterocyclyl, cycloalkyl, arylalkyl, heteroarylalkyl, heterocyclylalkyl, and cycloalkylalkyl of R$^4$, R$^7$, R$^9$, R$^{12}$, R$^{16}$, R$^{20}$, R$^{25}$, R$^{30}$, R$^{35}$, and R$^{40}$ are each independently unsubstituted or substituted with 1, 2, 3, 4, or 5 substituents independently selected from halogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino;

$R^{41}$, $R^{42}$, and $R^{44}$, at each occurrence, are each independently selected from the group consisting of hydrogen, alkyl, carboxyalkyl, aminoalkyl, alkylaminoalkyl, di(alkyl)aminoalkyl, sulfonate alkyl, tetraalkylammoniumalkyl, pyridiniumalkyl, imidazolylalkyl, guanidinolalkyl, hydroxyalkyl, carboxamidealkyl, thioalkyl, selanylalkyl, pyrrolidinyl, methylthioalkyl, phenylalkyl, 4-hydroxyphenylalkyl, and indolylalkyl;

$R^{43}$ and $R^{45}$ are each independently selected from the group consisting of hydrogen, —C(O)alkyl, and

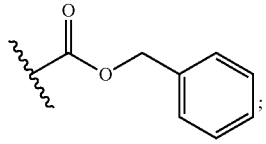

m, and n are each independently 1, 2, 3, 4, 5, or 6;

x, and y are each independently an integer selected from 1 to 20;

$R^B$ is —$(CR^{46}R^{47})_t$—$NR^{48}R^{49}$ or —$(CR^{53}R^{54})_z$—$SR^{55}$;

$R^{46}$ and $R^{47}$, at each occurrence, are each independently selected from the group consisting of hydrogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, hydroxy, amino, alkylamino, and di(alkyl)amino;

$R^{48}$ and $R^{49}$ are each independently selected from hydrogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, —$(CR^{50}R^{51})_z$—$OC(O)R^{52}$, —$(CR^{53}R^{54})_z$—$SR^{55}$, —$(CR^{56}R^{57})_z$—$S(O)R^{58}$, —$(CR^{59}R^{60})_z$—$S(O)_2R^{61}$, —$(CR^{62}R^{63})_z$—$N(R^{64})(R^{65})$, —$(CR^{66}R^{67})_z$—$N(R^{68})C(O)R^{69}$, —$(CR^{70}R^{71})_z$—$N(R^{72})S(O)_2R^{73}$, —$(CR^{74}R^{75})_z$—$N(R^{76})C(O)N(R^{77})(R^{78})$, —$(CR^{79}R^{80})_z$—$N(R^{81})S(O)_2N(R^{82})(R^{83})$, —$(CR^{84}R^{85})_z$—$C(O)R^{86}$, —$(CR^{87}R^{88})_z$—$C(O)O(R^{89})$, —$(CR^{90}R^{91})_z$—$C(O)N(R^{92})(R^{93})$, and —$C(R^{94})$=$N$—$OR^{95}$;

or $R^{48}$ and $R^{49}$ together with the nitrogen atom to which they are attached form a heterocyclyl, wherein said heterocyclyl is unsubstituted or substituted with 1, 2, 3, 4, 5 or 6 substituents independently selected from the group consisting of alkyl, alkenyl, alkynyl, —$NO_2$, —CN, halogen, oxo, —$OR^{96}$, —$OC(O)R^{97}$, —$SR^{98}$, —$S(O)R^{99}$, —$S(O)_2R^{100}$, —$S(O)_2N(R^{101})(R^{102})$, —$N(R^{103})(R^{104})$, —$N(R^{105})O(O)R^{106}$, —$N(R^{107})S(O)_2R^{108}$, —$N(R^{109})C(O)N(R^{110})(R^{112})$, —$N(R^{113})S(O)_2N(R^{114})(R^{115})$, —$C(O)R^{116}$, —$C(O)O(R^{117})$, —$C(O)N(R^{118})(R^{119})$, haloalkyl, —$(CR^{120}R^{121})_z$—CN, —$(CR^{122}R^{123})_z$—$OR^{124}$, —$(CR^{125}R^{126})_z$—$OC(O)R^{127}$, —$(CR^{128}R^{129})_z$—$SR^{130}$, —$(CR^{131}R^{132})_z$—$S(O)_R^{133}$, —$(CR^{134}R^{135})_z$—$S(O)_2R^{136}$, —$(CR^{137}R^{138})_z$—$N(R^{139})(R^{140})$, —$(CR^{141}R^{142})_z$—$N(R^{143})C(O)R^{144}$, —$(CR^{145}R^{146})_z$—$N(R^{147})S(O)_2R^{148}$, —$(CR^{149}R^{150})_z$—$N(R^{151})C(O)N(R^{152})(R^{153})$, —$(CR^{154}R^{155})_z$—$N(R^{156})S(O)_2N(R^{157})(R^{158})$, —$(CR^{159}R^{160})_z$—$C(O)R^{161}$, —$(CR^{162}R^{163})_z$—$C(O)O(R^{164})$ and —$(CR^{165}R^{166})_z$—$C(O)N(R^{167})(R^{168})$;

$R^{52}$, $R^{55}$, $R^{64}$, $R^{65}$, $R^{68}$, $R^{72}$, $R^{69}$, $R^{76}$, $R^{77}$, $R^{81}$, $R^{82}$, $R^{86}$, $R^{89}$, $R^{92}$, $R^{93}$, $R^{96}$, $R^{97}$, $R^{98}$, $R^{101}$, $R^{102}$, $R^{103}$, $R^{104}$, $R^{105}$, $R^{106}$, $R^{107}$, $R^{109}$, $R^{110}$, $R^{112}$, $R^{113}$, $R^{114}$, $R^{115}$, $R^{116}$, $R^{117}$, $R^{118}$, $R^{119}$, $R^{124}$, $R^{127}$, $R^{130}$, $R^{139}$, $R^{140}$, $R^{143}$, $R^{144}$, $R^{147}$, $R^{151}R^{152}$, $R^{153}$ $R^{156}$, $R^{157}$, $R^{158}$, $R^{161}$, $R^{164}$, $R^{167}$, and $R^{168}$, at each occurrence, are each independently selected from the group consisting of hydrogen, alkyl, alkoxyalkyl, aryl, arylalkyl, heteroaryl, heteroarylalkyl, cycloalkyl, cycloalkylalkyl, heterocyclyl, heterocyclylalkyl, haloalkoxyalkyl, and haloalkyl;

$R^{58}$, $R^{61}$, $R^{73}$, $R^{99}$, $R^{100}$, $R^{108}$, $R^{133}$, $R^{136}$, and $R^{148}$, at each occurrence, are each independently selected from alkyl and haloalkyl;

$R^{50}$, $R^{51}$, $R^{53}$, $R^{54}$, $R^{56}$, $R^{57}$, $R^{59}$, $R^{60}$, $R^{62}$, $R^{63}$, $R^{66}$, $R^{67}$, $R^{70}$, $R^{71}$, $R^{74}$, $R^{75}$, $R^{79}$, $R^{80}$, $R^{84}$, $R^{85}$, $R^{87}$, $R^{88}$, $R^{90}$, $R^{91}$, $R^{120}$, $R^{121}$, $R^{122}$, $R^{123}$, $R^{125}$, $R^{126}$, $R^{128}$, $R^{129}$, $R^{131}$, $R^{132}$, $R^{134}$, $R^{135}$, $R^{137}$, $R^{138}$, $R^{141}$, $R^{142}$, $R^{145}$, $R^{146}$, $R^{149}$, $R^{150}$, $R^{154}$, $R^{155}$, $R^{159}$, $R^{160}$, $R^{162}$, $R^{163}$, $R^{165}$, and $R^{166}$, at each occurrence, are each independently selected from hydrogen, halogen, alkyl, and haloalkyl;

$R^{94}$, and $R^{95}$, at each occurrence, are each independently selected from hydrogen and alkyl;

t is 1, 2, 3, 4, 5, 6, 7, or 8;

z, at each occurrence, is independently 1, 2, 3, or 4;

$R^C$ is —$(CH_2)_{0-3}$-T or $C_{1-5}$ alkyl; wherein T is aryl, heteroaryl, or cycloalkyl, wherein said aryl, heteroaryl, and cycloalkyl are each independently unsubstituted or substituted with 1, 2, or 3 substituents independently selected from the group consisting of halogen, alkyl, haloalkyl, hydroxyalkyl, alkoxyalkyl, haloalkoxyalkyl, aminoalkyl, alkylaminoalkyl, di(alkylaminoalkyl), cyanoalkyl, alkoxy, haloalkoxy, cyano, hydroxy, amino, alkylamino, and di(alkyl)amino;

$R^D$ is selected from the group consisting of hydrogen, lower cycloalkyl, benzyl, and $C_1$-$C_4$-alkyl; and $R^E$ is selected from the group consisting of —H, —OH, —$NH_2$, —OC(O)—$C_1$-$C_7$-alkyl or —$OCH_2OC(O)$—$C_1$-$C_7$-alkyl;

wherein the dashed bonds of formula (I) indicate the presence of an optional ring, which may be saturated or unsaturated.

In certain embodiments, $R^A$ is alkyl. In certain embodiments, $R^A$ is $C_1$-$C_{10}$-alkyl, $C_1$-$C_6$-alkyl, or $C_1$-$C_4$-alkyl. In certain embodiments, $R^A$ is methyl, ethyl, propyl (e.g., n-propyl, isopropyl), butyl (e.g., n-butyl, isobutyl, tert-butyl, sec-butyl), pentyl (e.g., n-pentyl, isopentyl, tert-pentyl, neopentyl, sec-pentyl, 3-pentyl), hexyl, heptyl, octyl, nonyl, or decyl.

In certain embodiments, $R^A$ is —$(CR^5R^6)_m$—$SO_3R^7$. In certain embodiments, $R^A$ is —$(CR^5R^6)_m$—$SO_3R^7$, wherein $R^5$ and $R^6$ are hydrogen at each occurrence, $R^7$ is as defined above, and m is 2 or 3. In certain embodiments, $R^A$ is —$(CR^5R^6)_m$—$SO_3R^7$, wherein $R^5$ and $R^6$ are hydrogen at each occurrence, $R^7$ is hydrogen, and m is 2 or 3. In certain embodiments, $R^A$ is —$(CR^5R^6)_m$—$SO_3R^7$, wherein $R^5$ and $R^6$ are hydrogen at each occurrence, $R^7$ is hydrogen, and m is 2 or 3, wherein the compound of formula (I) is in salt form such that $R^A$ is

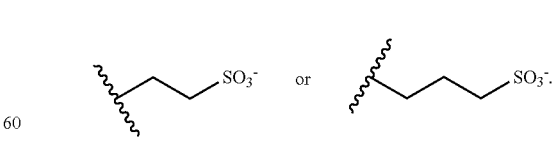

In certain embodiments, $R^A$ is —$(CR^1R^2)_m$—N($R^3$)C(O)$R^4$. In certain embodiments, $R^A$ is —$(CR^1R^2)_m$—N($R^3$)C(O)$R^4$, wherein $R^1$ and $R^2$ are hydrogen at each occurrence, $R^3$ is hydrogen or methyl, $R^4$ is as defined above, and m is 2 or 3. In certain embodiments, $R^A$ is

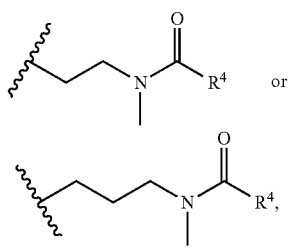

wherein $R^4$ is as defined above.

In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is alkyl, and m is 2 or 3. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is $C_1$-$C_4$-alkyl, and m is 2 or 3. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is methyl or isopropyl, and m is 2 or 3.

In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is alkoxy, and m is 2 or 3. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is $C_1$-$C_4$-alkoxy, and m is 2 or 3. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is tert-butoxy, and m is 2 or 3.

In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is aryl or heteroaryl, and m is 2 or 3, wherein said aryl and heteroaryl are each independently unsubstituted or substituted with 1, 2, 3, 4, or 5 substituents independently selected from halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is phenyl, and m is 2 or 3, wherein said phenyl is unsubstituted or substituted with 1, 2, 3, 4, or 5 substituents independently selected from halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is phenyl, and m is 2 or 3, wherein said phenyl is unsubstituted or substituted with 1 substituent selected from halogen, haloalkyl, and alkoxy. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is phenyl, and m is 2 or 3, wherein said phenyl is unsubstituted or substituted with 1 substituent selected from fluoro, trifluoromethyl, and methoxy.

In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is carboxyalkyl or carboxyalkoxyalkyl, and m is 2, 3, or 4. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is carboxymethyl ($-CH_2CO_2H$) or carboxymethoxymethyl ($-CH_2OCH_2CO_2H$), and m is 2, 3, or 4.

In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is alkylcarbonylalkoxylalkyl, and m is 2, 3, or 4. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is methylcarbonylmethoxymethyl ($-CH_2OCH_2C(O)CH_3$), and m is 2, 3, or 4.

In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is a peptide containing moiety, and m is 2, 3, or 4. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is a polypeptide containing moiety, and m is 2, 3, or 4. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is a polyaspartic acid containing moiety, and m is 2, 3, or 4. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is

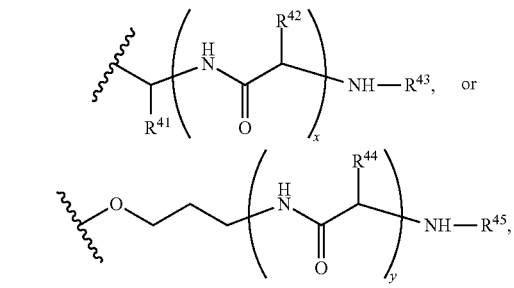

and m is 2, 3, or 4, wherein x, y, $R^{41}$, $R^{42}$, $R^{43}$, $R^{44}$, and $R^{45}$ are as defined above. In certain embodiments, $R^{41}$, $R^{42}$, and $R^{44}$ are each selected from $-CH_2CO_2H$. In certain embodiments, $R^{43}$ and $R^{45}$ are selected from acetyl ($-C(O)CH_3$). In certain embodiments, x is 1 or 2. In certain embodiments, y is 3.

In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is arylalkyl, and m is 2 or 3. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is a benzoquinonylalkyl, and m is 2 or 3. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is 2,5,6-trialkyl-1,4-benzoquinonylalkyl, and m is 2 or 3. In certain embodiments, $R^A$ is $(CR^1R^2)_m-N(R^3)C(O)R^4$, wherein $R^1$ and $R^2$ are hydrogen at each occurrence, $R^3$ is hydrogen or methyl, $R^4$ is 2,5,6-trimethyl-1,4-benzoquinonyl-$C_1$-$C_6$-alkyl, and m is 2 or 3. In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is

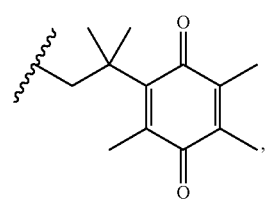 [SMILES: *CC(C)(C)C1=C(C)C(=O)C(C)=C(C)C1=O]

and m is 2 or 3.

39
In certain embodiments, $R^A$ is selected from
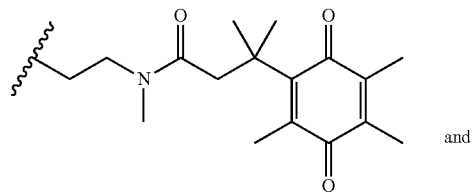
and
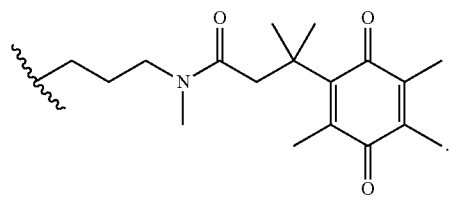
40
In certain embodiments, $R^A$ is $-(CR^1R^2)_m-N(R^3)C(O)R^4$, wherein $R^1$ and $R^2$ are hydrogen at each occurrence, $R^3$ is hydrogen or methyl, $R^4$ is arylalkyl, and m is 2 or 3
In certain embodiments, $R^A$ is selected from
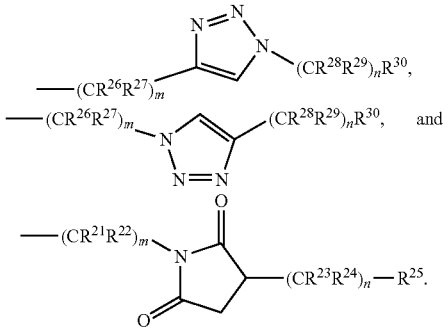
In certain embodiments, $R^A$ is selected from the group consisting of:
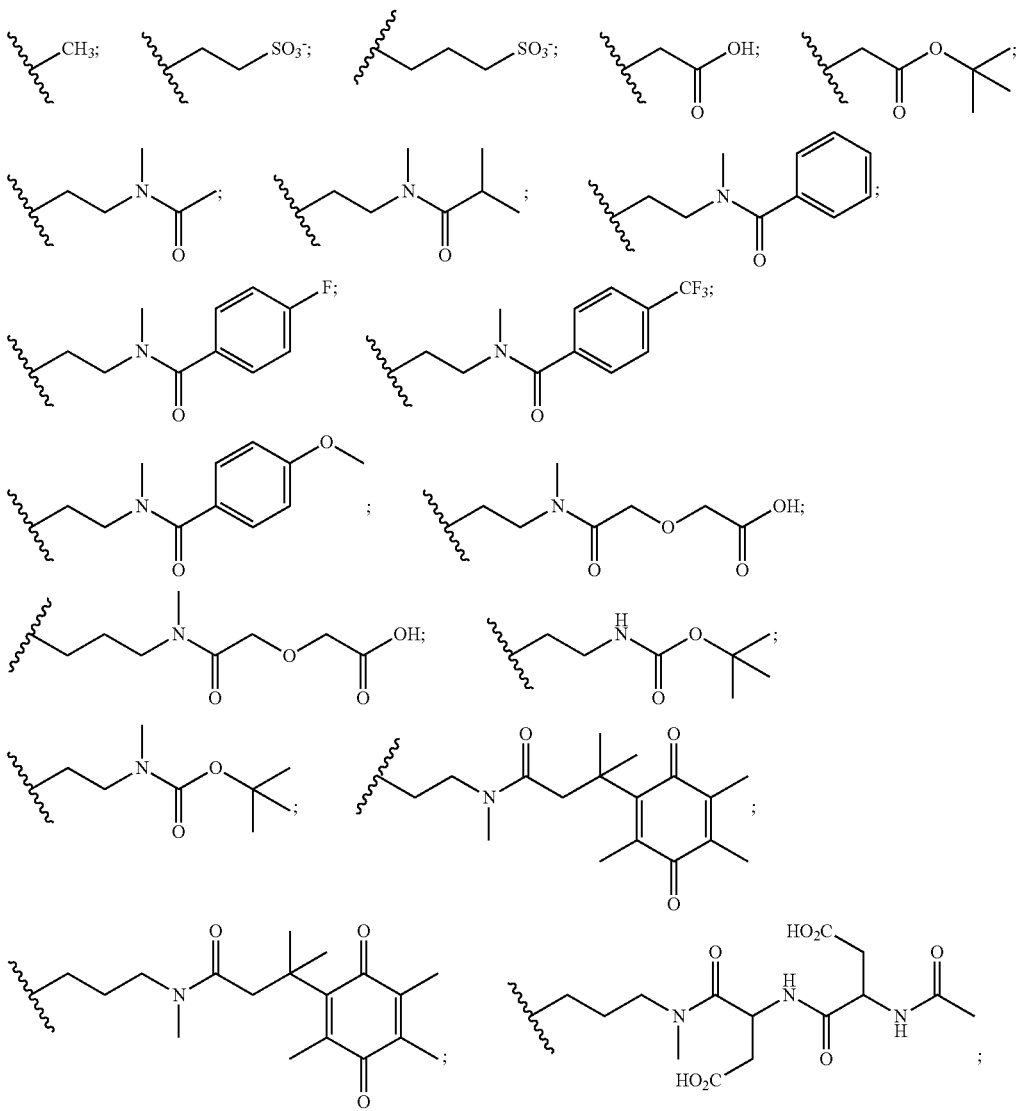

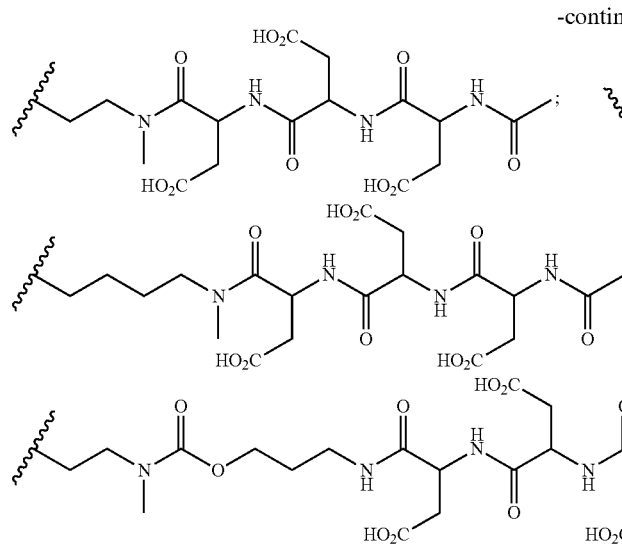
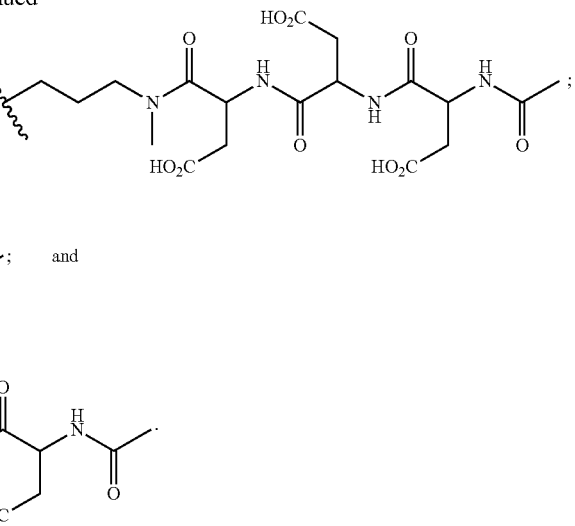

In certain embodiments, $R^B$ is a moiety comprising a functional group configured to react with the carbonyl group of —OC(O)NR$^A$R$^B$, wherein the functional group catalyzes nucleophilic addition to the carbonyl group of —OC(O)NR$^A$R$^B$.

In certain embodiments, $R^B$ is a moiety comprising a basic functional group (e.g., a moiety comprising an amino group). The basic functional group may catalyze nucleophilic addition (e.g., hydrolysis) to the carbonyl group of —OC(O)NR$^A$R$^B$, and/or the basic functional group may undergo a nucleophilic addition reaction with the carbonyl group of —OC(O)NR$^A$R$^B$.

In certain embodiments, $R^B$ is —(CR$^{46}$R$^{47}$)$_t$—NR$^{48}$R$^{49}$, wherein R$^{46}$ and R$^{47}$ are hydrogen at each occurrence. In certain embodiments, $R^B$ is —(CR$^{46}$R$^{47}$)$_t$—NR$^{48}$R$^{49}$, wherein R$^{46}$ and R$^{47}$ are hydrogen at each occurrence, and t is 2, 3, or 4. In certain embodiments, $R^B$ is —(CR$^{46}$R$^{47}$)$_t$—NR$^{48}$R$^{49}$, wherein R$^{46}$ and R$^{47}$ are hydrogen at each occurrence, t is 2, 3, or 4, and R$^{48}$ and R$^{49}$ are each alkyl. In certain embodiments, $R^B$ is —(CR$^{46}$R$^{47}$)$_t$—NR$^{48}$R$^{49}$, wherein R$^{46}$ and R$^{47}$ are hydrogen at each occurrence, t is 2, 3, or 4, and R$^{48}$ and R$^{49}$ are each —(CR$^{87}$R$^{88}$)$_z$—C(O)O(R$^{89}$), wherein R$^{87}$ and R$^{88}$ are hydrogen at each occurrence, R$^{89}$ is hydrogen or alkyl, and z is 1.

In certain embodiments, $R^B$ is —(CR$^{46}$R$^{47}$)$_t$—NR$^{48}$R$^{49}$, wherein R$^{46}$ and R$^{47}$ are hydrogen at each occurrence, t is 2, 3, or 4, and R$^{48}$ and R$^{49}$ together with the nitrogen atom to which they are attached form a heterocyclyl, wherein said heterocyclyl is unsubstituted or substituted. In certain embodiments, $R^B$ is —(CR$^{46}$R$^{47}$)$_t$—NR$^{48}$R$^{49}$, wherein R$^{46}$ and R$^{47}$ are hydrogen at each occurrence, t is 2, 3, or 4, and R$^{48}$ and R$^{49}$ together with the nitrogen atom to which they are attached form a piperazine, wherein said piperzine is unsubstituted or substituted. In certain embodiments, $R^B$ is —(CR$^{46}$R$^{47}$)$_t$—NR$^{48}$R$^{49}$, wherein R$^{46}$ and R$^{47}$ are hydrogen at each occurrence, t is 2, 3, or 4, and R$^{48}$ and R$^{49}$ together with the nitrogen atom to which they are attached form a piperazine, wherein said piperzine is substituted with —C(O)R$^{116}$, wherein R$^{116}$ is aryl. In certain embodiments, $R^B$ is —(CR$^{46}$R$^{47}$)$_t$—NR$^{48}$R$^{49}$, wherein R$^{46}$ and R$^{47}$ are hydrogen at each occurrence, t is 2, 3, or 4, and R$^{48}$ and R$^{49}$ together with the nitrogen atom to which they are attached form a morpholine, wherein said morpholine is unsubstituted or substituted. In certain embodiments, $R^B$ is —(CR$^{46}$R$^{47}$)$_t$—NR$^{48}$R$^{49}$, wherein R$^{46}$ and R$^{47}$ are hydrogen at each occurrence, t is 2, 3, or 4, and R$^{48}$ and R$^{49}$ together with the nitrogen atom to which they are attached form a morpholine, wherein said morpholine is unsubstituted.

In certain embodiments, $R^B$ is morpholinylalkyl. In certain embodiments, $R^B$ is morpholinyl-C$_1$-C$_4$-alkyl.

In certain embodiments, $R^B$ is selected from the group consisting of:

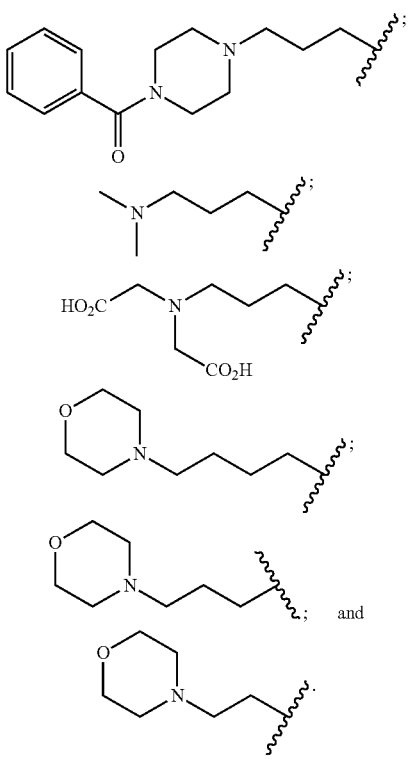

In certain embodiments, $R^B$ is —(CR$^{53}$R$^{54}$)$_z$—SR$^{55}$, wherein R$^{53}$, R$^{54}$, and R$^{55}$ are hydrogen at each occurrence.

In certain embodiments, $R^C$ is —$(CH_2)_{0-3}$-T, wherein T is aryl, or heteroaryl. In certain embodiments, $R^C$ is —$(CH_2)_{0-3}$-T, wherein T is phenyl, or 5-membered heteroaryl. In certain embodiments, $R^C$ is —$(CH_2)_{0-3}$-T, wherein T is phenyl or furyl. In certain embodiments, $R^C$ is —$(CH_2)$-T, wherein T is phenyl or furyl. In certain embodiments, $R^C$ is selected from the group consisting of:

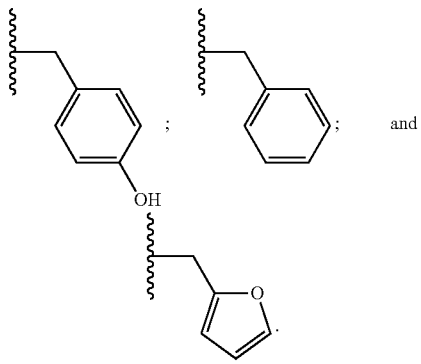

In certain embodiments, $R^D$ is benzyl.

In certain embodiments, $R^E$ is hydrogen.

In certain embodiments, compounds of the invention have formula (I-i), or a salt thereof,

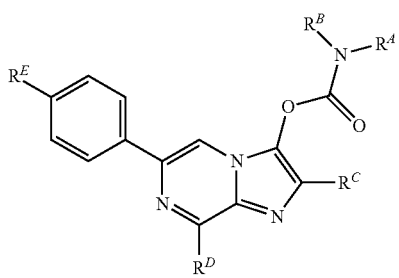

(I-i)

wherein $R^A$, $R^B$, $R^C$, $R^D$, and $R^E$ are as defined above.

In certain embodiments, compounds of the invention have formula (I-ii), or a salt thereof,

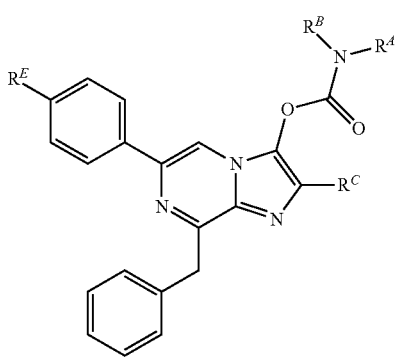

(I-ii)

wherein $R^A$, $R^B$, $R^C$, and $R^E$ are as defined above.

In certain embodiments, compounds of the invention have formula (I-iii), or a salt thereof,

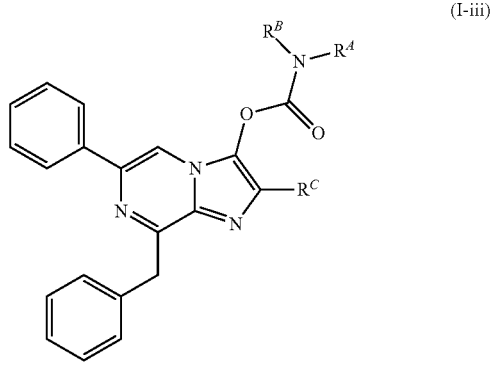

(I-iii)

wherein $R^A$, $R^B$, and $R^C$ are as defined above.

In certain embodiments, compounds of the invention have formula (I-iv), or a salt thereof,

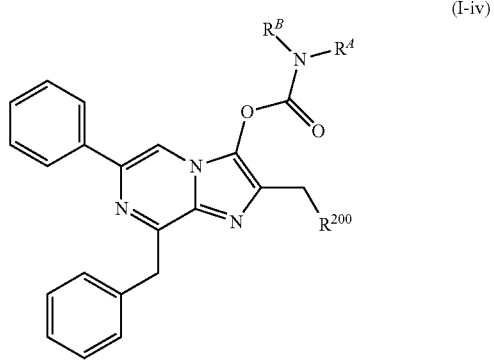

(I-iv)

wherein $R^{200}$ is aryl or heteroaryl, each optionally substituted with 1, 2, or 3 substituents independently selected from the group consisting of halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino; and $R^A$, and $R^B$ are as defined above.

In certain embodiments, compounds of the invention have formula (I-v), or a salt thereof,

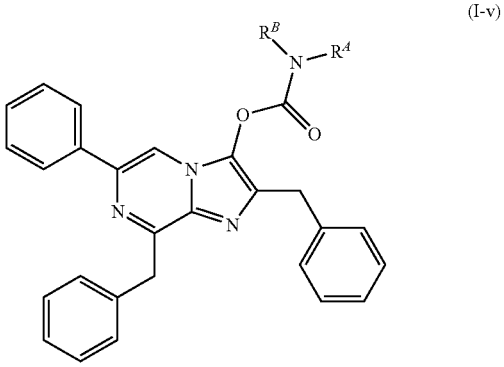

(I-v)

wherein $R^A$, and $R^B$ are as defined above.

In certain embodiments, compounds of the invention have formula (I-vi), or a salt thereof,

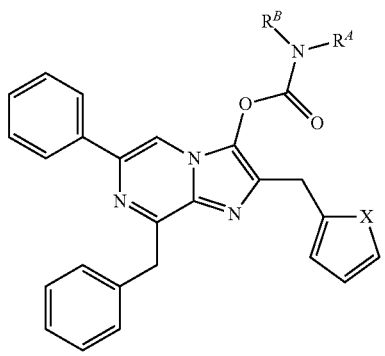

(I-vi)

wherein X is O, S, or NH; and $R^A$, and $R^B$ are as defined above.

In certain embodiments, compounds of the invention have formula (I-vii), or a salt thereof,

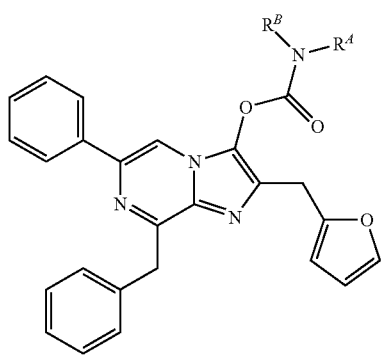

(I-vii)

wherein $R^A$, and $R^B$ are as defined above.

In certain embodiments, compounds of the invention have formula (I-viii), or a salt thereof,

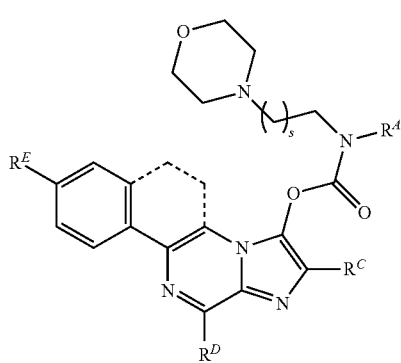

(I-viii)

wherein s is 1 or 2; and $R^A$, $R^C$, $R^D$, and $R^E$ are as defined above.

In certain embodiments, compounds of the invention have formula (I-ix), or a salt thereof,

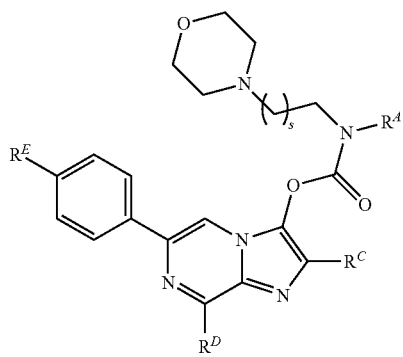

(I-ix)

wherein s is 1 or 2; and $R^A$, $R^C$, $R^D$, and $R^E$ are as defined above.

In certain embodiments, compounds of the invention have formula (I-x), or a salt thereof,

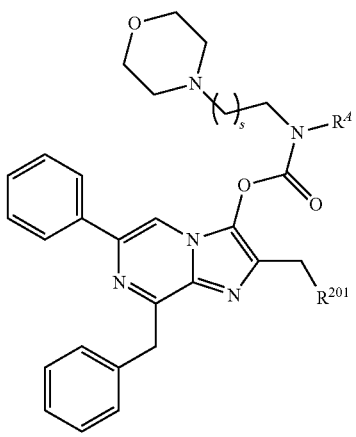

(I-x)

wherein s is 1 or 2; $R^{201}$ is aryl or heteroaryl, each optionally substituted with 1, 2, or 3 substituents independently selected from the group consisting of halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino; and $R^A$ is as defined above.

In certain embodiments, compounds of the invention have formula (I-xi), or a salt thereof,

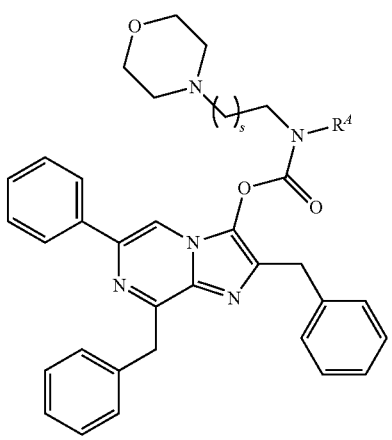

(I-xi)

wherein s is 1 or 2; and $R^A$ is as defined above.

In certain embodiments, compounds of the invention have formula (I-xii), or a salt thereof,

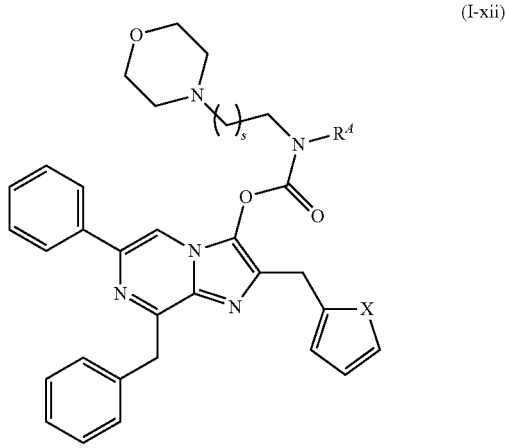

(I-xii)

wherein s is 1 or 2; X is O, S, or NH; and $R^A$ is as defined above.

In certain embodiments, compounds of the invention have formula (I-xiii), or a salt thereof,

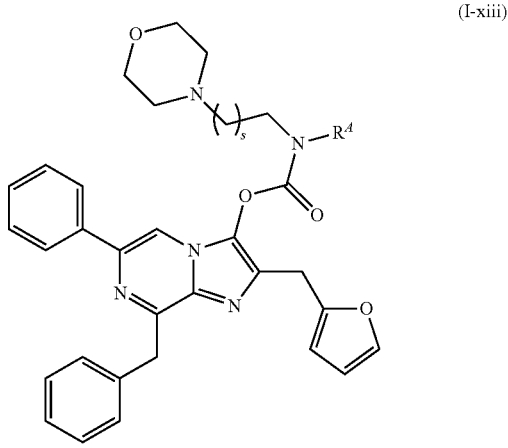

(I-xiii)

wherein s is 1 or 2; and $R^A$ is as defined above.

In certain embodiments, compounds of the invention have formula (I-xiv), or a salt thereof,

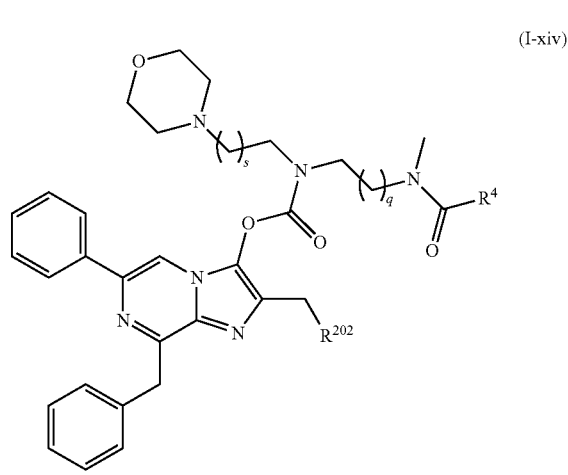

(I-xiv)

wherein q is 1 or 2; s is 1 or 2; $R^{202}$ is aryl or heteroaryl, each optionally substituted with 1, 2, or 3 substituents independently selected from the group consisting of halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino; and $R^4$ is as defined above.

In certain embodiments, compounds of the invention have formula (I-xv), or a salt thereof,

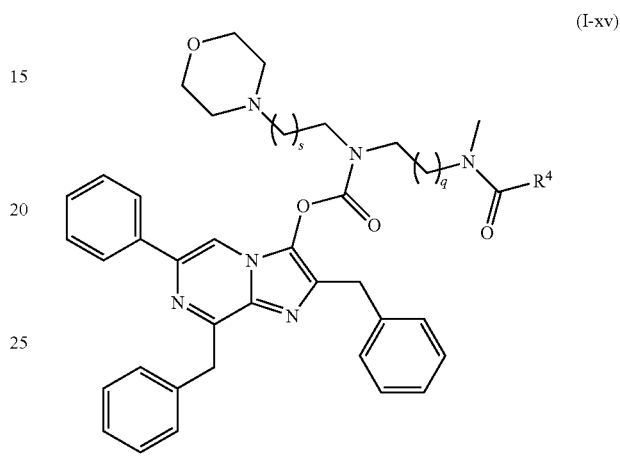

(I-xv)

wherein q is 1 or 2; s is 1 or 2; and $R^4$ is as defined above.

In certain embodiments, compounds of the invention have formula (I-xvi), or a salt thereof,

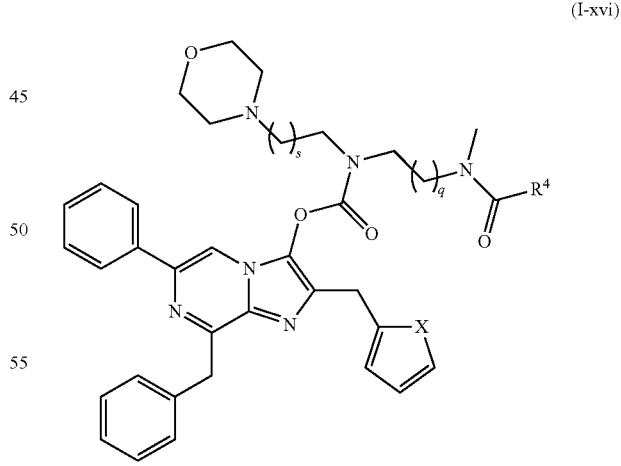

(I-xvi)

wherein q is 1 or 2; s is 1 or 2; X is O, S, or NH; and $R^4$ is as defined above.

In certain embodiments, compounds of the invention have formula (I-xvii), or a salt thereof, (I-xvii)

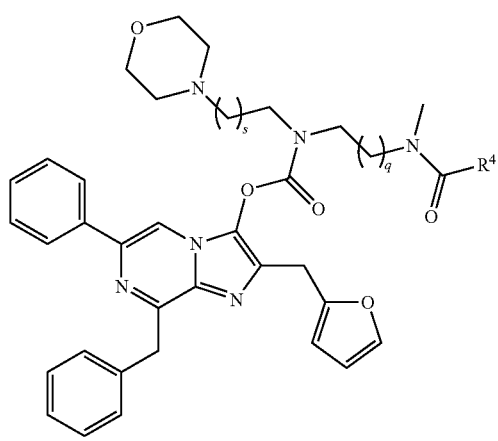

wherein q is 1 or 2; s is 1 or 2; and R⁴ is as defined above.

In certain embodiments, the compounds of the invention are selected from the group consisting of:

5296

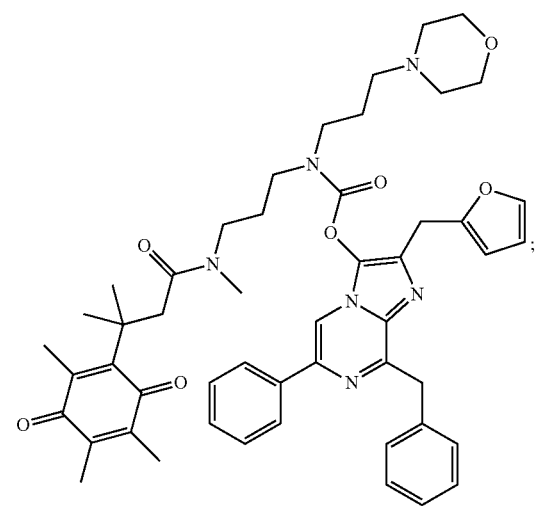

8-benzyl-2-(furan-2-ylmethyl)-6-phenylimidazo[1,2-a]pyrazin-3-yl (3-(N,3-dimethyl-3-(2,4,5-trimethyl-3,6-dioxocyclohexa-1,4-dien-1-yl)butanamido)propyl)(3-morpholinopropyl)carbamate

5295

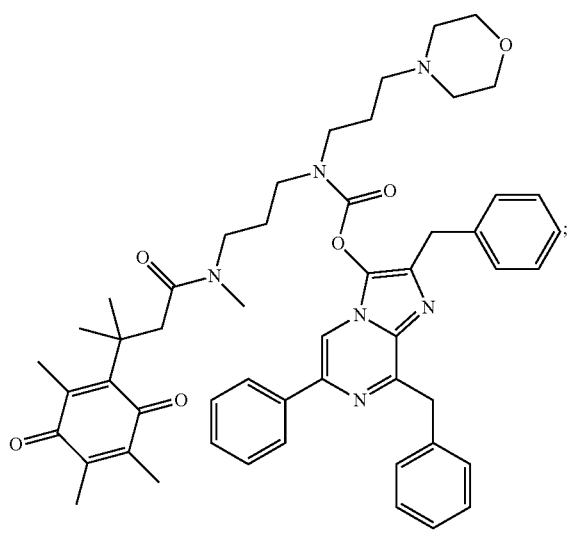

2,8-dibenzyl-6-phenylimidazo[1,2-a]pyrazin-3-yl (3-(N,3-dimethyl-3-(2,4,5-trimethyl-3,6-dioxocyclohexa-1,4-dien-1-yl)butanamido)propyl)(3-morpholinopropyl)carbamate

5393

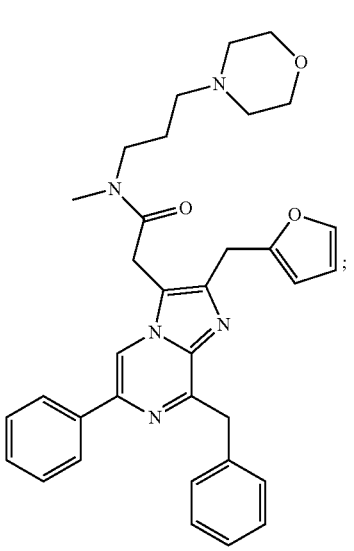

8-benzyl-2-(furan-2-ylmethyl)-6-phenylimidazo[1,2-a]pyrazin-3-yl methyl(3-morpholinopropyl)carbamate

5394

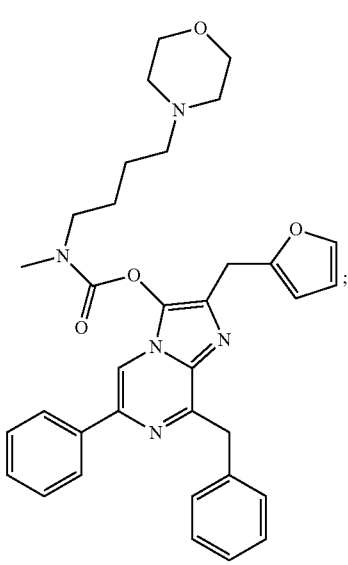

8-benzyl-2-(furan-2-ylmethyl)-6-phenylimidazo[1,2-a]pyrazin-3-yl methyl(4-morpholinobutyl)carbamate

5442

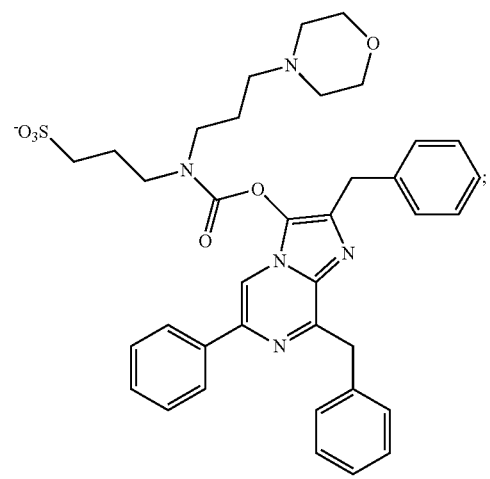

3-((((2,8-dibenzyl-6-phenylimidazo[1,2-a]pyrazin-3-yl)oxy)carbonyl)(3-morpholinopropyl)amino)propane-1-sulfonate

5455

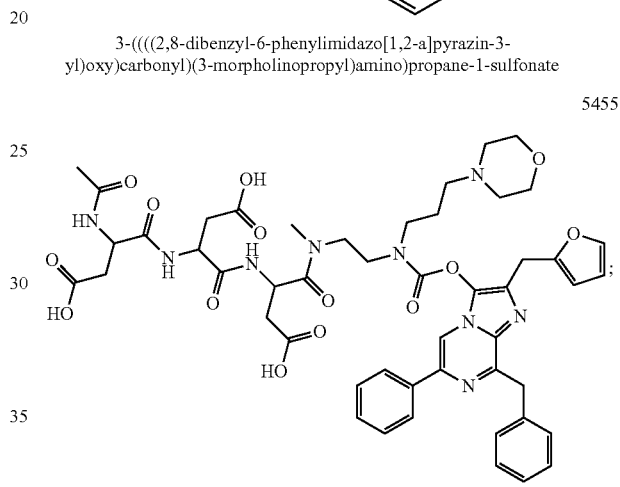

15-acetamido-4-((((8-benzyl-2-(furan-2-ylmethyl)-6-phenylimidazo[1,2-a]pyrazin-3-yl)oxy)carbonyl)-9,12-bis(carboxymehtyl)-7-methyl-1-morpholino-8,11,14-trioxo-4,7,10,13-tetraazaheptadecan-17-oic acid

5396

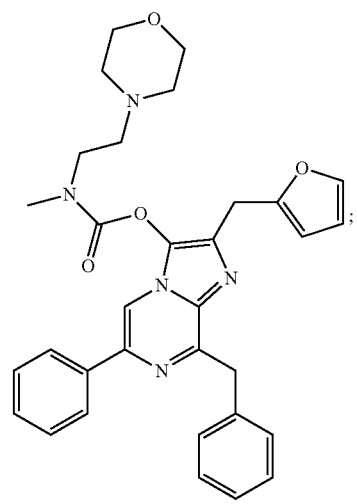

8-benzyl-2-(furan-2-ylmethyl)-6-phenylimidazo[1,2-a]pyrazin-3-yl methyl(2-morpholinoethyl)carbamate

5456

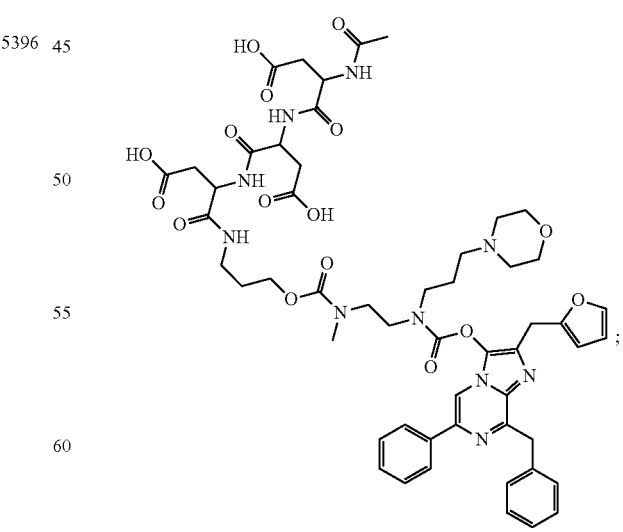

21-acetamido-4-((((8-benzyl-2-(furan-2-ylmethyl)-6-phenylimidazo[1,2-a]pyrazin-3-yl)oxy)carboxymethyl)-7-methyl-1-morpholino-8,14,17,20-tetraoxo-9-oxa-4,7,13,16,19-pentaazatricosan-23-oic acid

5457

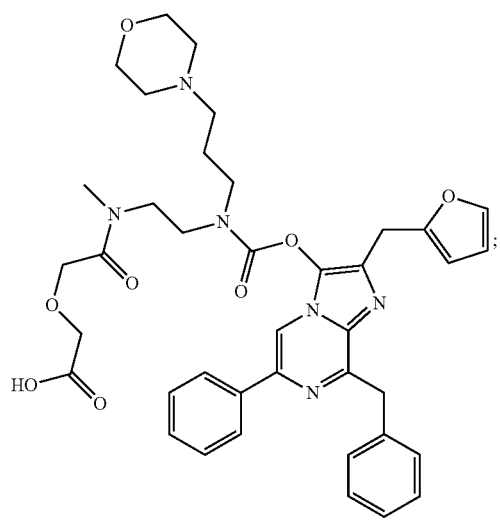

2-(2-((2-(((((8-benzyl-2-(furan-2-ylmethyl)-6-phenylimidazo[1,2-a]pyrazin-3-yl)oxy)carbonly)(3-morpholinopropyl)amino)ethyl)(methyl)amino)-2-oxoethoxy)acetic acid

5489

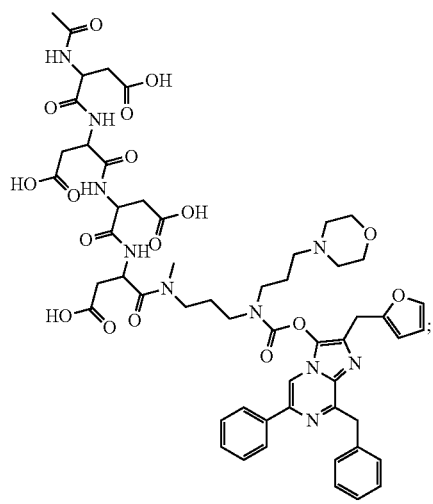

19-acetamido-4-(((8-benzyl-2-(furan-2-ylmethyl)-6-phenylimidazo[1,2-a]pyrazin-3-yl)oxy)carbonyl)-10,13,16-tris(carboxymethyl)-8-methyl-1-morpholino-9,12,15,18-tetraoxo-4,8,11,14,17-pentaazahenicosan-21-oic acid

5488

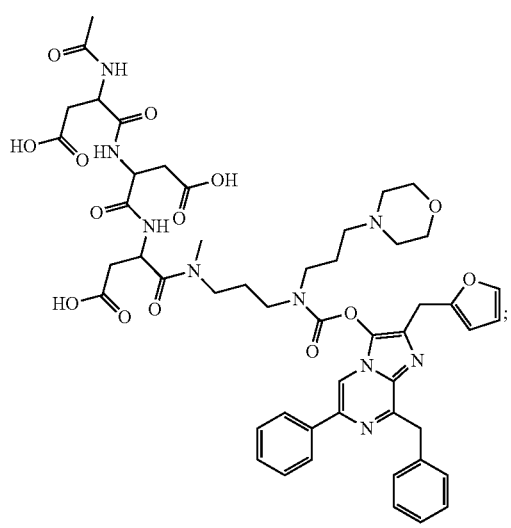

16-acetamido-4-(((8-benzyl-2-(furan-2-ylmethyl)-6-phenylimidazo[1,2-a]pyrazin-3-yl)oxy)carbonyl)-10,13-bis(carboxymethyl)-8-methyl-1-morpholino-9,12,15-trioxo-4,8,11,14-tetraazaoctadecan-18-oic acid

5370

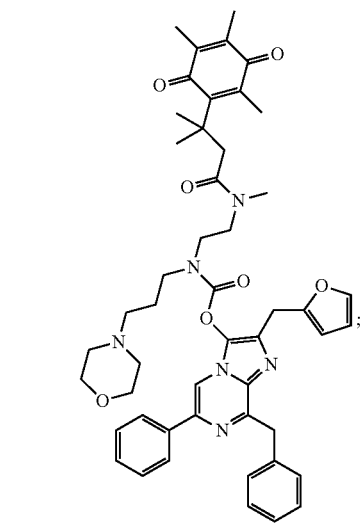

8-benzyl-2-(furan-2-ylmethyl)-6-phenylimidazo[1,2-a]pyrazin-3-yl (2-(N,3-dimethyl-3-(2,4,5-trimethyl-3,6-dioxocyclohexa-1,4-dien-1-yl)butanamido)ethyl)(3-morpholinopropyl)carbamate

55
-continued

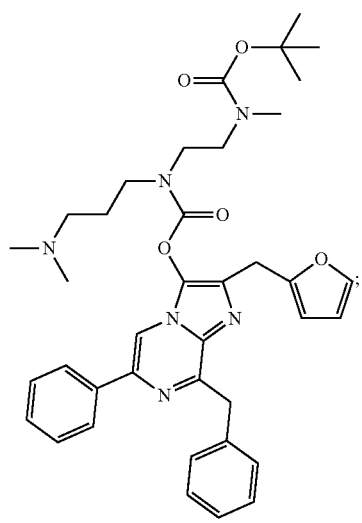

8-benzyl-2-(furan-2-ylmethyl)-6-phenylimidazo[1,2-a]pyrazin-3-yl (2-((tert-butoxycarbonyl)(methyl)amino)ethyl)(3-dimethylamino)propyl)carbamate

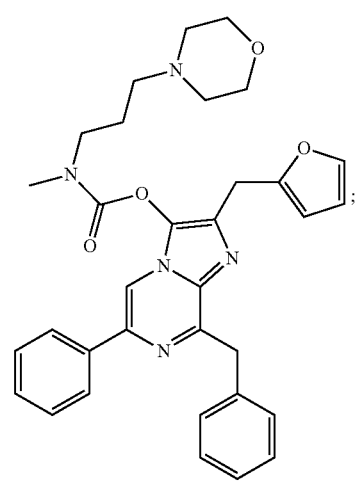

8-benzyl-2-(furan-2-ylmethyl)-6-phenylimidazo[1,2-a]pyrazin-3-yl methyl(3-morpholinopropyl)carbamate

56
-continued

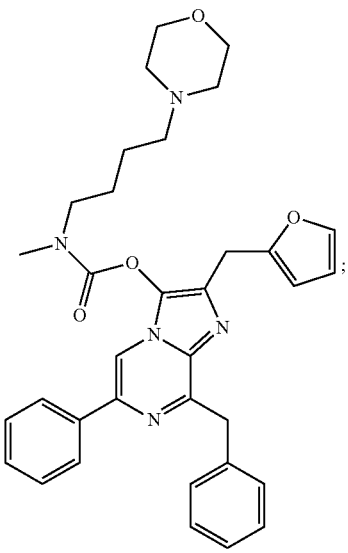

8-benzyl-2-(furan-2-ylmethyl)-6-phenylimidazo[1,2-a]pyrazin-3-yl methyl(4-morpholinobutyl)carbamate

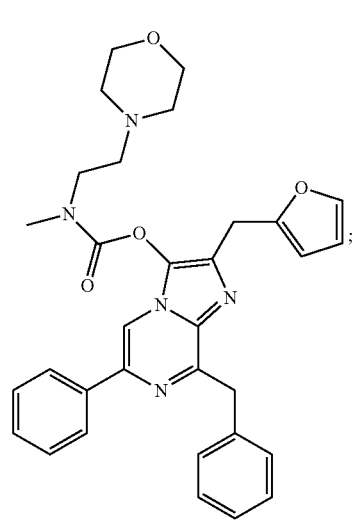

8-benzyl-2-(furan-2-ylmethyl)-6-phenylimidazo[1,2-a]pyrazin-3-yl methyl(2-morpholinoethyl)carbamate -continued

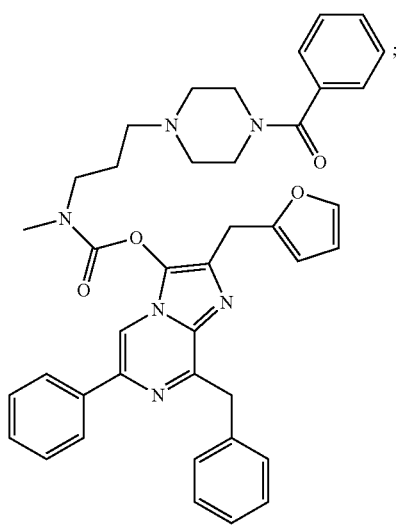

5422

8-benzyl-2-(furan-2-ylmethyl)-6-phenylimidazo[1,2-a]pyrazin-3-yl (3-(4-benzoylpiperazin-1-yl)propyl)(methyl)carbamate

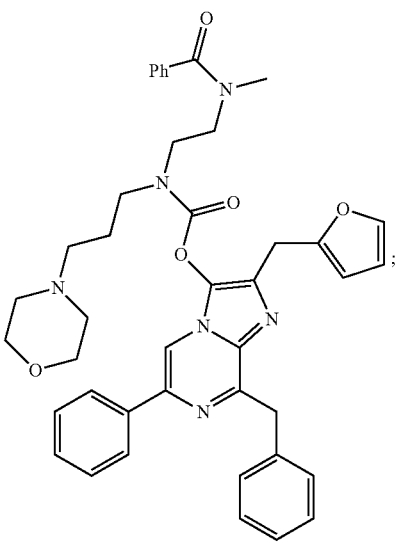

5417

8-benzyl-2-(furan-2-ylmethyl)-6-phenylimidazo[1,2-a]pyrazin-3-yl (2-(N-methylbenzamido)ethyl)(3-morpholinopropyl)carbamate

5416

8-benzyl-2-(furan-2-ylmethyl)-6-phenylimidazo[1,2-a]pyrazin-3-yl (2-((tert-butoxycarbonyl)(methyl)amino)ethyl)(3-morpholinopropyl))carbamate

5418

8-benzyl-2-(furan-2-ylmethyl)-6-phenylimidazo[1,2-a]pyrazin-3-yl (2-(N-methylacetamido)ethyl)(3-morpholinopropyl)carbamate

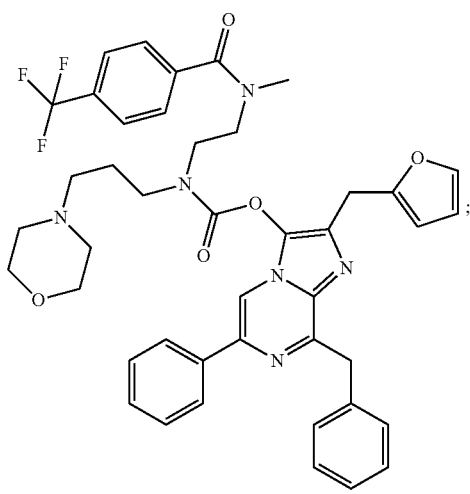

8-benzyl-2-(furan-2-ylmethyl)-6-phenylimidazo[1,2-a]pyrazin-3-yl (2-(N-methyl-4-(trifluoromethyl)benzamido)ethyl)(3-morpholinopropyl)carbamate

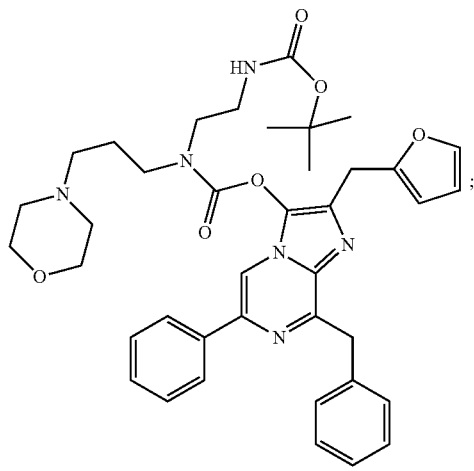

8-benzyl-2-(furan-2-ylmethyl)-6-phenylimidazo[1,2-a]pyrazin-3-yl (2-((tert-butoxycarbonyl)amino)ethyl)(3-morpholinopropyl)carbamate

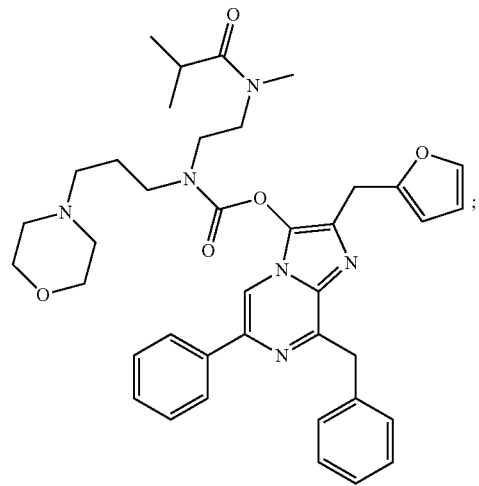

8-benzyl-2-(furan-2-ylmethyl)-6-phenylimidazo[1,2-a]pyrazin-3-yl (2-(N-methylisobutyramido)ethyl)(3-morpholinopropyl)carbamate

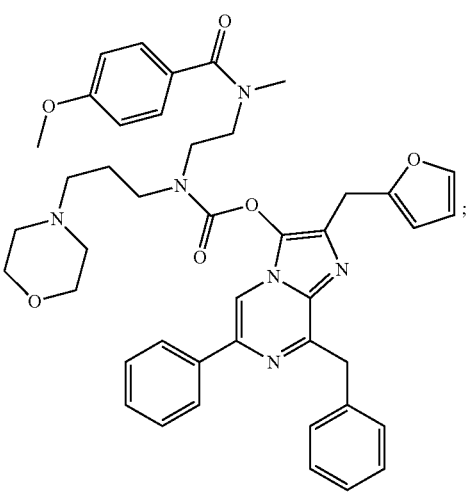

8-benzyl-2-(furan-2-ylmethyl)-6-phenylimidazo[1,2-a]pyrazin-3-yl (2-(4-methoxy-N-methylbenzamido)ethyl)(3-morpholinopropyl)carbamate

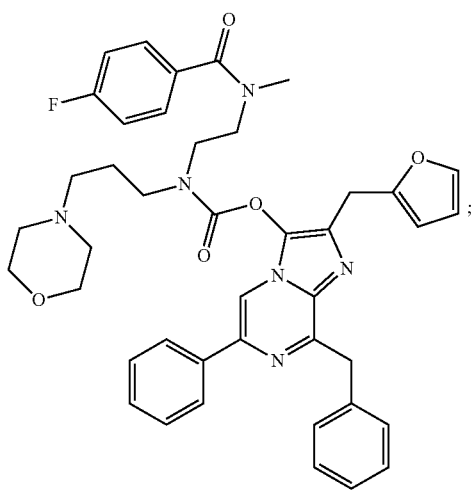

8-benzyl-2-(furan-2-ylmethyl)-6-phenylimidazo[1,2-a]pyrazin-3-yl (2-(4-fluoro-N-methylbenzamido)ethyl)(3-morpholinopropyl)carbamate

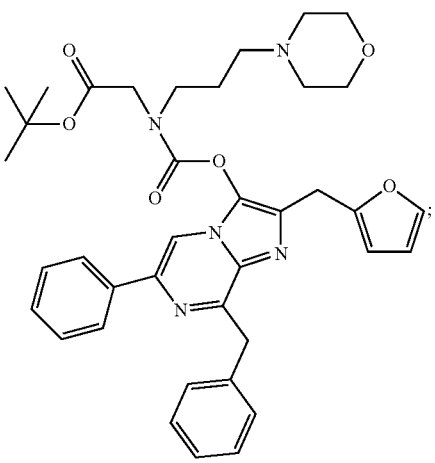

tert-butyl N-((((8-benzyl-2-(furan-2-ylmethyl)-6-phenylimidazo[1,2-a]pyrazin-3-yl)oxy)carbonyl)-N-(3-morpholinopropyl)glycinate

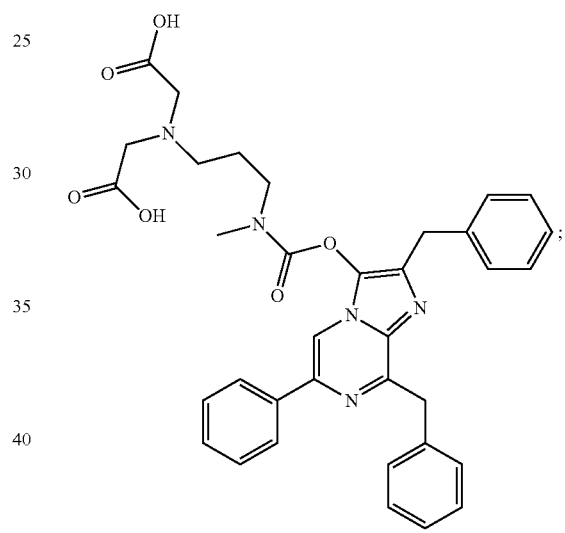

2,2'-((3-(((((2,8-dibenzyl-6-phenylimidazo[1,2-a]pyrazin-3-yl)oxy)carbonly)(methyl)amino)propyl)azanediyl)diacetic acid

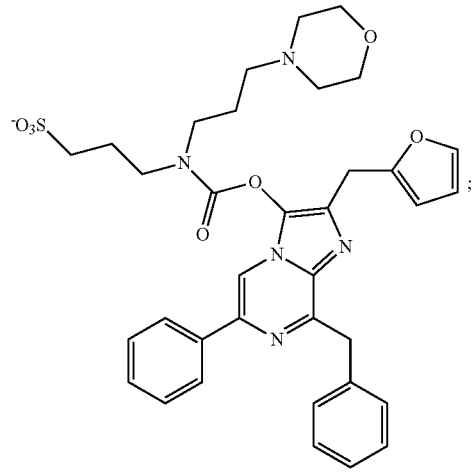

3-(((((8-benzyl-2-(furan-2-ylmethyl)-6-phenylimidazo[1,2-a]pyrazin-3-yl)oxy)carbonyl)(3-morpholinopropyl)amino)propane-1-sulfonate

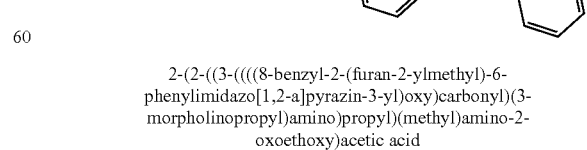

2-(2-((3-(((((8-benzyl-2-(furan-2-ylmethyl)-6-phenylimidazo[1,2-a]pyrazin-3-yl)oxy)carbonyl)(3-morpholinopropyl)amino)propyl)(methyl)amino-2-oxoethoxy)acetic acid and

5487

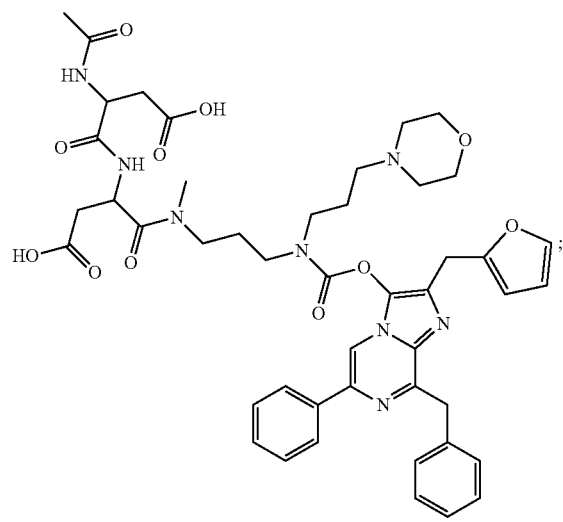

3-acetamido-4-((1-((3-((((8-benzyl-2-(furan-2-ylmethyl)-
6-phenylimidazo[1,2-a]pyrazin-3-yl)oxy)carbonyl)(3-
morpholinopropyl)amino)propyl)(methyl)amino)-3-
carboxy-1-oxopropan-2-yl)amino)-4-oxbutanoic acid or a salt thereof.

In certain embodiments, the following compounds are excluded as compounds of formula (I):

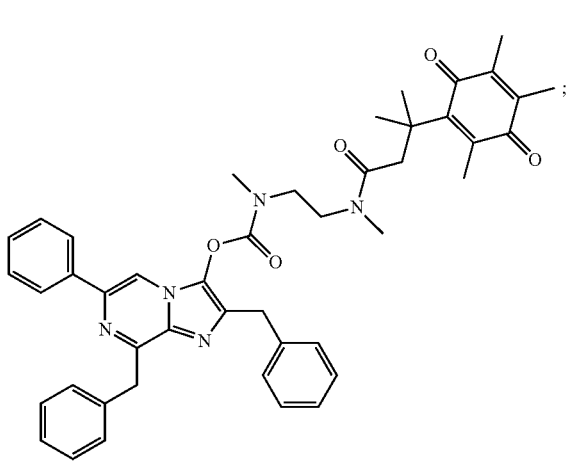

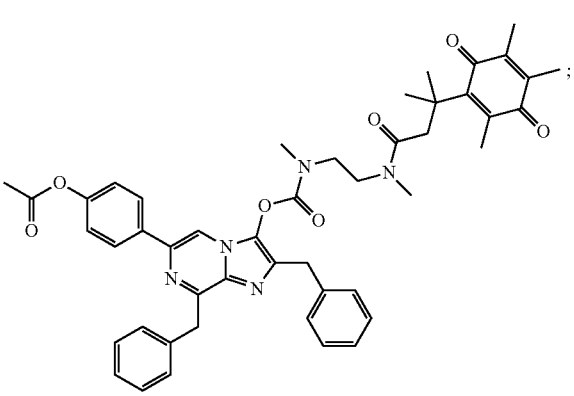

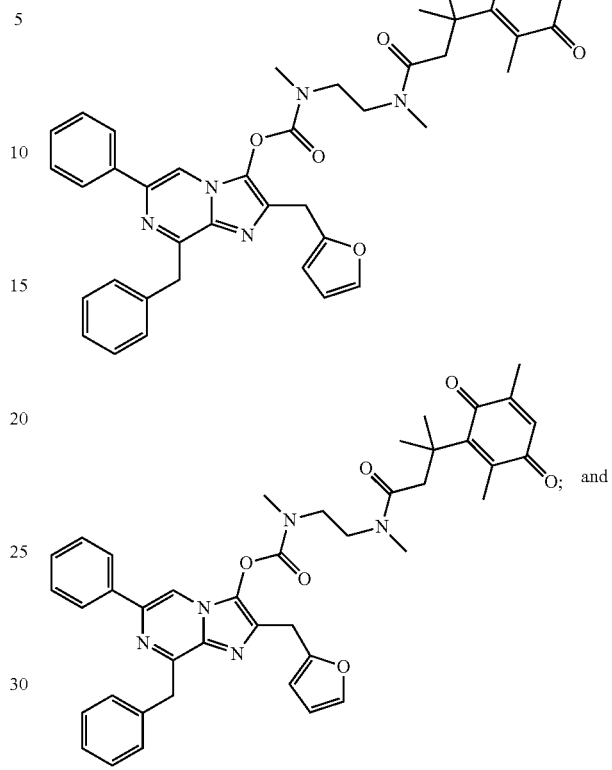

b. Intramolecular Reaction

The cell impermeable pro-substrates may be converted to a cell permeable substrate by an intramolecular reaction. The cell impermeable substrates may contain an amine base (or nucleophile) and, optionally, one or more charged functional groups. The cell impermeable pro-substrates may comprise a functional group configured to cleave the cell impermeable moiety of the pro-substrate (e.g., via catalysis of a nucleophilic addition reaction, such as a hydrolysis reaction). The functional group may cleave the cell impermeable moiety via an intramolecular reaction within the same molecule, referred to as "self-based catalysis." Cleavage of the cell impermeable moiety releases the cell permeable substrate.

The cell impermeable pro-substrate, such as the compound of formula (I), may be converted to a cell permeable substrate in the extracellular medium of a sample containing cells. Cleavage of the cell impermeable moiety of the pro-substrate may be tuned by choice of the internal base and/or pH of the medium and/or addition of nucleophiles to the medium. Suitable nucleophiles for addition to the medium include, but are not limited to, alcohols (e.g., ethanol), alkoxide anion (e.g., methoxide, ethoxide), hydrogen sulfide, thiols (e.g., methanthiol), thiolate anions, azide, and amines (e.g., methylamine). The rate of reaction of the cell impermeable pro-substrate may be controlled, for example, by adjusting the pH of the solution containing the cell impermeable pro-substrate. The cell impermeable moiety may be cleaved with a nucleophile-containing solution or a non-luminescent enzyme before or after the cell impermeable pro-substrate is in contact with a sample.

c. Non-Luminescent Enzyme Reaction

The cell impermeable pro-substrates disclosed herein, including but not limited compounds of formula (I), may be converted to a cell permeable substrate in the extracellular medium of a sample containing cells. The cell impermeable pro-substrate may be converted to a cell permeable substrate by contacting the cell impermeable pro-substrate with a non-luminescent enzyme (e.g., phosphatase, protease, esterase, or sulfatase) that cleaves the cell impermeable moiety to release the cell permeable substrate. The cell impermeable pro-substrate may be converted to a cell permeable substrate by, for example, contacting the pro-substrate with a non-luminescent enzyme before or after the cell impermeable pro-substrate is in contact with a sample. Cell impermeable pro-substrates that may be converted to cell permeable substrates through reaction with a non-luminescent enzyme include, but are not limited to, compounds of formula (I), compounds of formula (a), compounds of formula (b), compounds of formula (c), and compounds of formula (d):

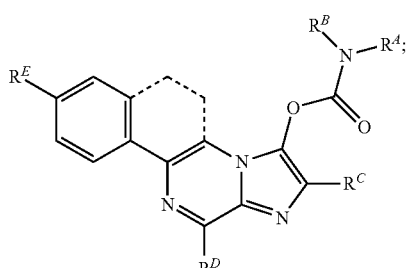
(I)

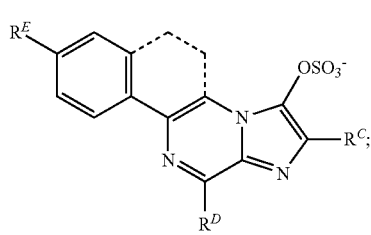
(a)

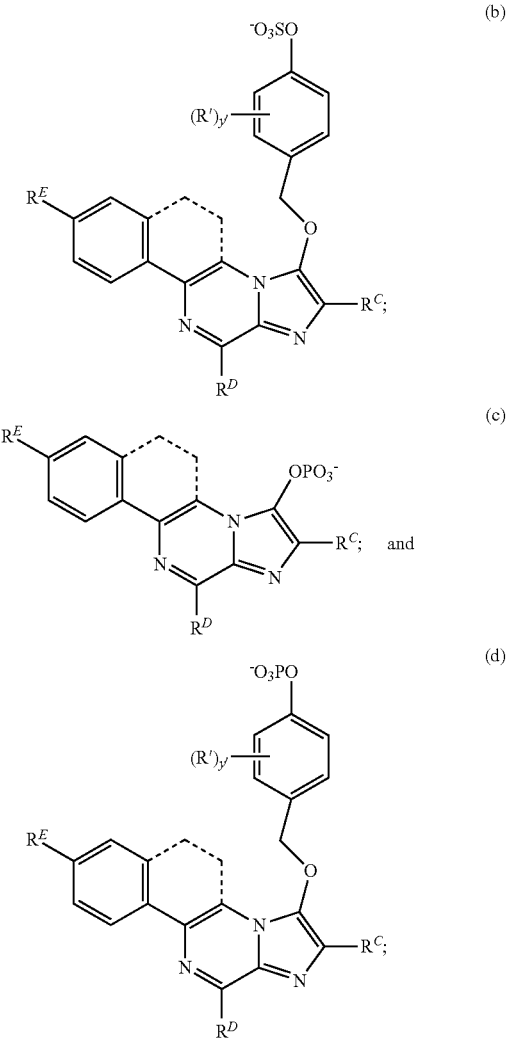

wherein R' is, at each occurrence, independently selected from the group consisting of halogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino; y' is 0, 1, 2, 3, or 4; and $R^A$, $R^B$, $R^C$, $R^D$, and $R^E$ are as defined above.

3. METHODS

The disclosed compounds may be used in assays to detect the presence or activity of enzymes. The compounds of the invention may be used in any way that luciferase substrates, e.g., coelenterazines, have been used. For example, they may be used in a bioluminogenic method which employs a coelenterazine to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The disclosed compound may be hydrolyzed to provide a cell permeable substrate that is a substrate for a luminescent enzyme, e.g., a coelenterazine-utilizing luciferase. In certain embodiments, step (a) further comprises contacting the sample with a nucleophilic compound configured to react with a compound of formula (I) to provide a cell permeable substrate. The cell permeable substrate may be a compound of formula (II), as defined above.

In some aspects, provided are methods for detecting the presence of a luminescent enzyme, e.g., a coelenterazine-utilizing luciferase. The method includes (a) contacting a sample with the disclosed compound; and (b) detecting luminescence in the sample. The detection of luminescence indicates the presence of a luminescent enzyme. The presence, amount, spectral distribution, emission kinetics, or specific activity of an enzyme may be detected or quantified. The enzyme may be detected or quantified in solution, including multiphasic solutions (e.g., emulsions or suspensions), or on solid supports (e.g., particles, capillaries, or assay vessels). In some embodiments, the luminescent enzyme may be used as an energy donor to another molecule (e.g., to a fluorophore, a chromophore, or a nanoparticle). In still other embodiments, a sample (including cells, tissues, animals, etc.) containing a luminescent enzyme and/or the disclosed compounds may be assayed using various microscopy and imaging techniques.

The disclosed compounds are also useful in in situ methods of analyzing cells. Methods of performing in situ analysis of cells using a luciferase are known in the art.

The disclosed compounds may be used to distinguish between substrates and inhibitors of an enzyme. The screening may be performed either in vitro or in vivo.

In addition, for any of the bioluminogenic assays described herein, other reagents may be added to reaction mixtures, including but not limited to those that inhibit or prevent inactivation of luciferase or otherwise extend or enhance luminescent signal.

(1) Luminescent Enzymes

In certain embodiments, a method may include contacting a compound disclosed herein to a cell expressing a luminescent enzyme. The disclosed compounds may provide a substrate, i.e., the cell-permeable substrate, for an intracellular luciferase. Suitable luminescent enzymes include luciferases that utilize coelenterasine (or a derivative or analog thereof) as a substrate (coelenterazine-utilizing luciferase), e.g., luciferases derived from bioluminescent decapods, such as from the Oplophoroidea, e.g. *Oplophorus*-derived luciferases, marine organisms such as cnidarians (e.g., *Renilla* luciferase), Aristeidae, Solenoceridae, Luciferidae, Sergestidae, Pasipheidae and Thalassocarididae decapoda families, copepod luciferases, such as *Gaussia* luciferase, such as *Gaussia princeps* luciferase, *Metridia* luciferases, such as *Metridia longa* and *Metridia pacifica* luciferases, *Vargula* luciferases, such as *Vargula hilgendorfii* luciferase, *Pleuromamma xiphias* luciferase, and variants, recombinants, and mutants thereof. The compounds may be used with photoproteins such as *Aequorin*, obelin, iPhotina, and variants, recombinants, and mutants thereof. In some embodiments, the luciferase may be an *Oplophorus* luciferase or a variant of an *Oplophorus* luciferase, such as NANOLUC®. *Oplophorus* luciferase variants are described in U.S. Pat. No. 8,557,970 and U.S. Patent Publication No. US20120117667 both of which are incorporated herein by reference in their entirety.

(2) Use with Transcriptional Reporters

The disclosed compounds may be used with genetic transcriptional reporter systems. In certain embodiments, provided is a method for measuring the activity of a promoter in a sample, wherein the promoter is operably linked to a gene encoding a luminescent enzyme. The method includes (a) contacting the sample with the disclosed compound; and (b) determining the activity of the promoter by measuring luminescence of the sample, wherein the sample comprises the promoter. The promoter may be operably linked to the gene via a translational or transcriptional fusion. A biological pathway of interest, for example, may be examined by treating a cell that comprises the promoter, which is operably linked to a gene encoding the luminescent enzyme, with an inducer agent of the pathway. This promoter activity may then be measured and monitored to study any correlation between the activity of the promoter and the pathway of interest, as well as obtain kinetic measurements relating to gene expression (e.g. inducibility, repression and activation).

In some embodiments, the luminescent enzyme, e.g., coelenterazine-utilizing luciferase, may be multiplexed with another enzyme (e.g. a luciferase) that emits light at a different wavelength, e.g., green firefly luciferase, e.g., *Photinus pyralis* (e.g., Luc2; Promega Corp) or red click beetle luciferase (CHROMA-LUC™; Promega Corp.). For example, if a luminescent enzyme of the present invention is used as a functional reporter, then the green firefly luciferase or red CHROMA-LUC™ luciferase could be used to control for non-specific effects on genetic regulation or to normalize for transfection efficiency. In some embodiments, luminescence generated from the luminescent enzyme (approximately 460 nm) and red CHROMA-LUC™ (approximately 610 nm) can be easily resolved using a luminometer with wavelength-discriminating filters, enabling the measurement of both signals from the same sample. In another example, a luminescent enzyme could be used as a transcriptional reporter and paired with a luciferase that emits light at a different wavelength contained in an assay reagent. In another example, a luminescent enzyme may be used with one or more additional luciferases, where the luminescence of each luciferase may be separately measured through the use of selective enzyme inhibitors. For example, the luminescence of a first luciferase may be measured upon addition of appropriate substrates and buffers, followed by measurement of a second luciferase upon a subsequent addition of appropriate substrates and buffers and one or more inhibitors selective for the first luciferase. In another example, the luciferase contained in an assay reagent may be used for measuring a specific aspect of cellular physiology, for example ATP to estimate cell viability, or caspase activity to estimate cellular apoptosis.

(3) Bioluminescence Resonance Energy Transfer (BRET)

The disclosed compounds may be used in any method for detecting ligand-protein and/or protein-protein interactions. The cell-permeable substrate, generated from the disclosed compounds, can be used by a luminescent enzyme. In various embodiments, the luminescent enzymes may be used to transfer energy to an energy acceptor. One such method is Bioluminescence Resonance Energy Transfer (BRET). With respect to BRET, energy transfer from a bioluminescent donor to a fluorescent acceptor results in a shift in the spectral distribution of the emission of light. This energy transfer may enable real-time monitoring of protein-protein or ligand-protein interaction in vitro or in vivo. In some embodiments, the BRET method may be the NANOLUC®-Mediated Bioluminescence Resonance Energy Transfer (NANOBRET®) Assay for ligand-protein and protein-protein interactions. NANOBRET comprises two different methods: 1) using HALOTAG® and NANOLUC® technologies, Bioluminescence Resonance Energy Transfer (BRET) to detect protein-protein and/or ligand-protein interactions may be achieved with increased signal and decreased spectral overlap; and 2) using NANOLUC fused to a protein of interest and a fluorescent tracer to detect ligand-receptor interaction in living cells.

In some embodiments, the luminescent enzymes used in BRET analysis can be used to determine if two molecules are capable of binding to each other or co-localize in a cell. For example, a luminescent enzyme can be used as a bioluminescence donor molecule which is combined with a molecule or protein of interest to create a first fusion protein. In various embodiments, the first fusion protein contains a luminescent enzyme and a protein of interest. In various embodiments, the first fusion proteins containing the luminescent enzyme can be used in BRET analysis to detect protein/protein interaction in systems including but not limited to cell lysates, intact cells, and living animals. In various embodiments, HALOTAG® can be used as a fluorescent acceptor molecule. In some embodiments, HALOTAG® can be fused to a second protein of interest or to a luminescent enzyme. For example, a luminescent enzyme can be fused to HALOTAG®, expressed in cells or animals, and labeled with a fluorescent HALOTAG® ligand such as HALOTAG® TMR ligand. The fusion can subsequently be excited to fluoresce in the presence of a cell-permeant luminescent enzyme substrate. In some embodiments, BRET may be performed using luminescent enzymes in combination with fluorescent proteins, including but not limited to Green Fluorescent Protein (GFP) or Red Fluorescent Protein (RFP) or fluorescent labels including fluorescein, rhodamine green, Oregon green, or Alexa 488, to name a few non-limiting examples.

(4) Protein Proximity Assays for Live Cells or Lytic Formats

In some embodiments, the disclosed compounds may be used with circularly permuted (CP) or straight split (SS) luminescent enzyme fusion proteins to measure protein proximity. A luminescent enzyme is permuted or split via insertion of a protease substrate amino acid sequence (e.g., TEV) to generate low bioluminescence. The inactive luminescent enzyme is tethered (e.g., via genetic fusion) to a monitor protein. A potential interacting protein is tethered (e.g., via genetic fusion) to a protease (e.g., TEV). When the two monitor proteins interact or are in sufficient proximity (e.g., via a constitutive interaction, a drug stimulus or a pathway response), the luminescent enzyme is cleaved to generate increased bioluminescence activity. The example may be applied to measurements of protein proximity in cells or in biochemical assays.

(5) Protein Complementation Assays

In some embodiments, the disclosed compounds may be used in other methods for detecting ligand-protein and protein-protein interactions or proximity, such as the protein complementation assay (PCA) or enzyme fragmentation assay. Protein complementation assays (PCA) provide a means to detect the interaction of two biomolecules, e.g., polypeptides. PCA utilizes two fragments of the same protein, e.g., enzyme, that when brought into close proximity with each other can reconstitute into a functional, active protein. In some embodiments, the NANOBIT® technology (Promega Corporation) may be used to detect molecular proximity by virtue of the reconstitution of a luminescent enzyme via the binding interaction of enzyme components or subunits. NANOBIT utilizes a non-luminescent peptide (NLPep) and non-luminescent polypeptide (NLPoly) derived from the *Oplophorus* luciferase variant, NANOLUC luciferase. The NLPep and NLPoly are fused to proteins of interest. If the proteins of interest interact, NLPep and NLPoly interact to reconstitute a full-length *Oplphorus* luciferase enzyme.

For example, a luminescent enzyme can be separated into two fragments at a site(s) tolerant to separation and each fragment of the separated luminescent enzyme can be fused to one of a pair of polypeptides of interest believed to interact, e.g., FKBP and FRB. If the two polypeptides of interest do in fact interact, the luminescent enzyme fragments, for example, then come into close proximity with each other to reconstitute the functional, active luminescent enzyme. In some embodiments, the activity of the reconstituted luminescent enzyme can then be detected and measured using the disclosed compounds and the cell-permeable substrate. In some embodiments, the split luminescent enzyme can be used in a more general complementation system similar to lac-Z (Langley et al., *PNAS* 72:1254-1257 (1975)) or ribonuclease S (Levit and Berger, *J. Biol. Chem.* 251:1333-1339 (1976)). In some embodiments, a luminescent enzyme fragment (designated "A") known to complement with another luminescent enzyme fragment ("B") can be fused to a target protein, and the resulting fusion can be monitored via luminescence in a cell or cell lysate containing fragment B. In some embodiments, the source of fragment B could be the same cell (e.g., if the gene for fragment B is integrated into the genome of the cell or is contained on another plasmid within the cell) or it could be a lysate or purified protein derived from another cell. In some embodiments, this same fusion protein (fragment A) could be captured or immobilized using a fusion between fragment B and a polypeptide such as HALOTAG® capable of attachment to a solid support. In some embodiments, luminescence can be used to demonstrate successful capture or to quantify the amount of material captured.

(6) Dimerization Assay

In some embodiments, the disclosed compounds may be used with full-length circularly permuted luminescent enzymes fused to respective binding partners, e.g., FRB and FKBP, and used in a protein complementation-type assay. The key difference between the method disclosed herein and traditional protein complementation is that there was no complementation, but rather there was dimerization of two full length enzymes, e.g., circularly permuted luminescent enzymes.

Briefly, the circularly permuted reporter proteins similarly configured for low activity are fused to both of the fusion protein partners. For example, each fusion partner may be linked to identically structured, permuted reporters. Interaction of the fusion partners brought the permuted reporters into close proximity, thereby allowing reconstitution of a hybrid reporter having higher activity.

(7) Combinations

Figure 15:
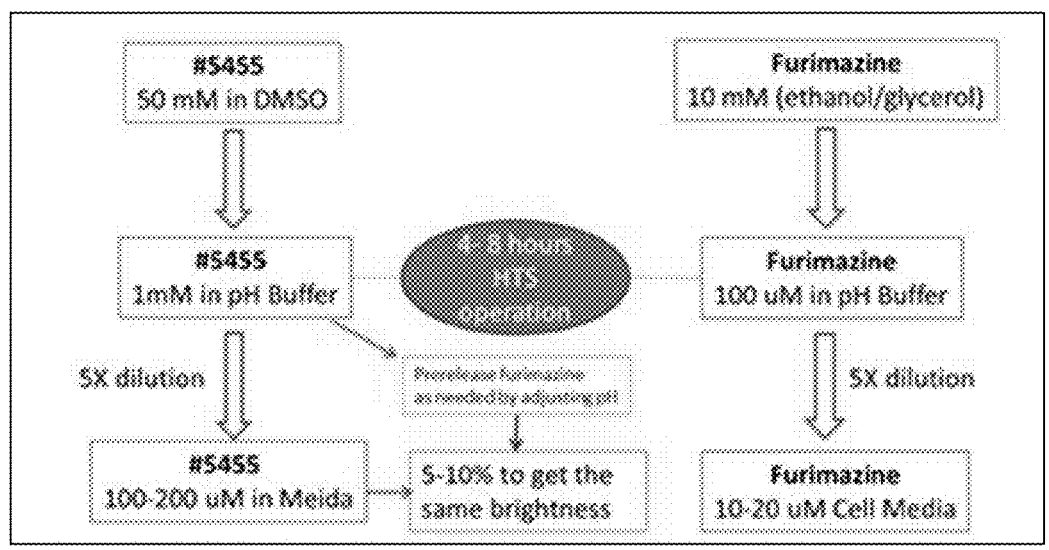
FIG. 15 depicts a schematic showing an HTS operation using PBI-5455 with furimazine.

In certain embodiments, the methods disclosed herein include contacting a sample (e.g., a cell) with a mixture of a cell impermeable pro-substrate and its corresponding cell permeable substrate (see e.g., FIG. 15). In certain embodiments, the methods disclosed herein include preincubating a disclosed cell impermeable compounds in an appropriate pH buffer condition or an appropriate nucleophile solution to release cell permeable substrate to an extent, and then contacting the sample (e.g. cells) with the above preincubated solution. In certain embodiments, the methods disclosed herein include contacting a sample with a cell impermeable substrate and a nucleophilic combined configured to react with the carbamate functionality of the cell impermeable substrate to release a cell permeable substrate (e.g., a coelenterazine). In some embodiments, the disclosed compounds and methods may be used to build up the initial brightness of a high-throughput screening operation assay format. Such methods may provide enhanced brightness at an initial sample duration time with sustained release of coelenterazines to the sample.

(8) Sample

The disclosed compounds may be used with samples containing biological components. The sample may comprise cells. The sample may comprise heterogeneous mixtures of components (including intact cells, cell extracts, cell lysates, bacteria, viruses, organelles, and mixtures thereof) or a single component or homogeneous group of components (e.g., natural or synthetic amino acid, nucleic acid or carbohydrate polymers, or lipid membrane complexes). The compounds are generally non-toxic to living cells and other biological components within the concentrations of use.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). In certain embodiments, the sample may be a cell. In some embodiments, the sample may be a live cell. The cell may be a eukaryotic cell, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cell may or may not express a luciferase. The cells may have been genetically modified via recombinant techniques.

4. KITS

Disclosed are kits for determining the presence or activity of one or more enzymes (e.g., luciferase). The kit may include one or more of the following: a compound or composition of the invention, coelenterazine-dependent luminescent enzyme(s), and reaction buffer(s). The reaction buffers may be present in individual formulations for the non-luciferase enzyme reactions and the luminescent enzyme reactions or in a single formulation for a single step assay. The kits may also contain inhibitors, activators and/or enhancers for the non-luciferase enzyme(s). The kits may also contain a positive and/or negative control for the assay.

5. EXAMPLES

The foregoing may be better understood by reference to the following examples, which are presented for purposes of illustration and are not intended to limit the scope of the invention.

Example 1

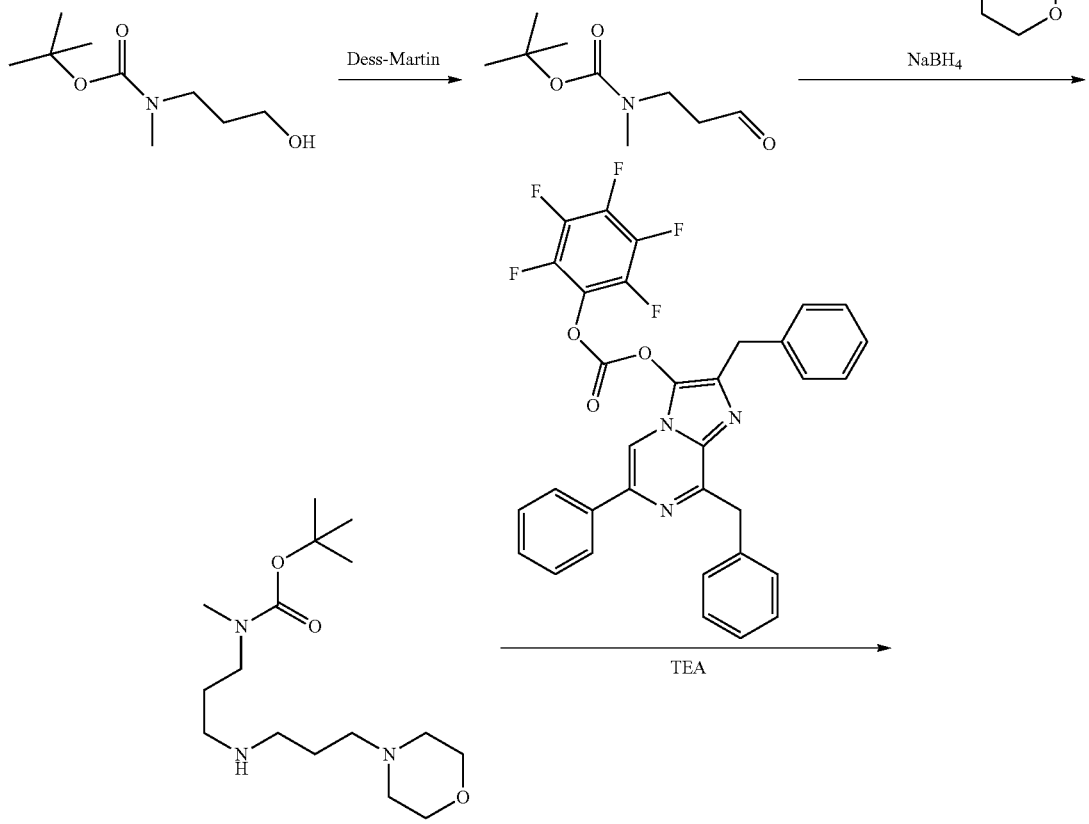

-continued
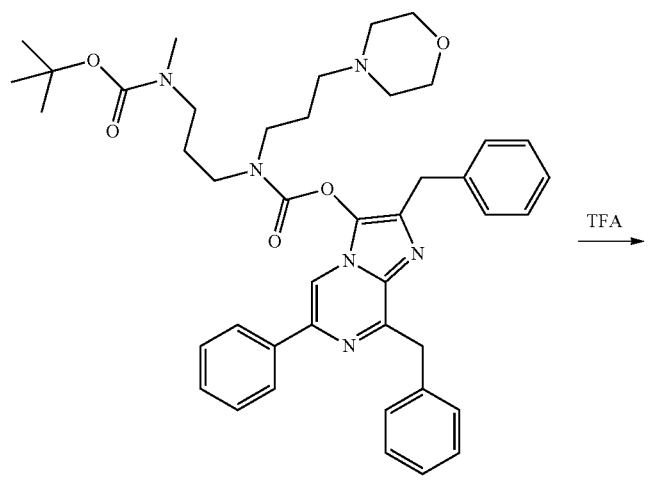
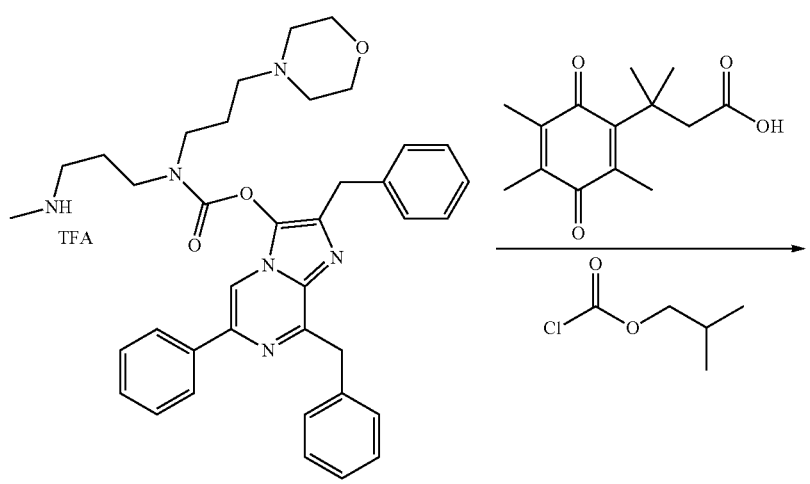
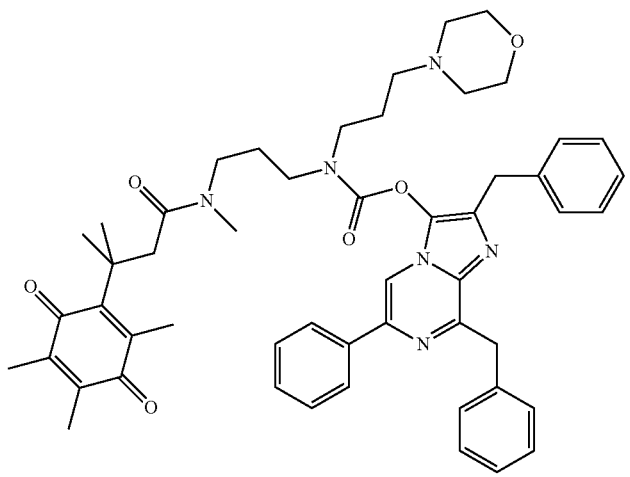
5295

Synthesis of 3-[(N-methyl-N-Boc]propanal

Des-Martin reagent (16.02 g, 37.78 mmol) was added to the solution of 3-(N-methyl-N-Boc) propanol (6.5 g, 34.35 mmol) in 120 ml of methylene chloride at 0° C., and the resultant mixture was stirred at room temperature for 4 hours. The reaction mixture was quenched with saturated sodium thiosulphate solution, and the product was extracted with methylene chloride. The organic layer was washed with saturated sodium bicarbonate solution, brine solution and water and dried over anhydrous sodium sulphate. The solvent was evaporated under reduced pressure and purified by flash column chromatography using heptane and ethyl acetate as eluent to give 4.8 g of desired product in a yield of 74.64%. $^1$H NMR (300 MHz, $CD_2Cl_2$) δ ppm: 9.80 (s, 1H, HC=O), 3.50 (t, 2H, $CH_2$), 2.83 (s, 3H, $CH_3$), 2.62 (t, 2H, $CH_2$); MS-ESI (m/e): 188.2 [M+H].

Synthesis of N'-methyl-N'-Boc-N-(3-morpholinopropyl)propane-1,3-diamine

To a solution of morpholine propylamine (0.231 g, 1.60 mmol) in 20 ml of methanol, 3-[(N-methyl)Boc]propanal (0.3 g, 1.60 mmol) was added. The mixture was stirred at room temperature for 3 hours. $NaBH_4$ (0.18 g, 4.81 mmol) was added to the mixture at 0° C., and the resultant mixture was stirred at 0° C. for 1 hour and 1 hour at room temperature. The reaction was quenched by adding 5 ml of water. After removal of solvent, 5 ml of water was added, and the mixture was extracted three times with methylene chloride. The combined organic layer was dried over $Na_2SO_4$, and the desired product was obtained after evaporating the solvent and, without further purification, the product was used directly in the next step.

Synthesis of coelenterazine HH—[N'-methyl-N'-Boc-N-(3-morpholinopropyl)propane-1,3-diamine]carbamate To the mixture of coelenterazine HH (0.1 g, 0.256 mmol) and bis(pentafluorophenyl)dicarbonate (0.112 g, 0.256 mmol) in 10 ml of dry THF, TEA (52 mg, 0.512 mmol) was added at room temperature under argon. The mixture was stirred for 2-3 minutes until the solid disappeared, and tert-butyl methyl(3-((3-morpholinopropyl)amino)propyl) carbamate (0.161 g, 0.512 mmol) was added. The resulting mixture was stirred at room temperature for 30 minutes. The compound was purified by flash column chromatography using heptane/ethyl acetate/THF as eluent to give the product in a yield of 69.3% (0.13 g, 0.177 mmol). MS-ESI (m/e): 719.5 [M+H]$^+$.

Synthesis of coelenterazine HH—[N'-methyl-N-(3-morpholinopropyl)propane-1,3-diamine]carbamate Coelenterazine HH—[N'-methyl-N'-Boc-N-(3-morpholinopropyl) propane-1,3-diamine]carbamate (0.1 g, 0.136 mmol) and triisopropylsilane (50 ul) were dissolved in 10 ml of methylene chloride and TFA (1:1 in volume), and the mixture was stirred at room temperature for 2 hours. After removal of the solvent, the residue was dried under high vacuum overnight, and the product was used directly in the next step.

Synthesis of #5295

To the solution of 3-methyl-3-(2,4,5-trimethyl-3,6-dioxo-cyclohexa-1,4-dien-1-yl)butanoic acid (102.5 mg, 0.409 mmol) and isobutyl chloroformate (55.9 mg, 0.409 mmol) in 10 ml of dry THF, N-methyl morphorline (82.8 mg) was added at 0° C. The resultant mixture was stirred for 30 minutes at 0° C., and coelenterazine HH—[N'-methyl-N-(3-morpholinopropyl)propane-1,3-diamine]carbamate in 5 ml of $CH_2Cl_2$ was added, and the resultant mixture was stirred for 1 hour. The compound was directly purified with flash silica column chromatography using heptane and ethyl acetate as eluent to give the product in a yield of 74% (0.087 g). MS-ESI (m/e): 865.5 [M+H]$^+$.

Example 2

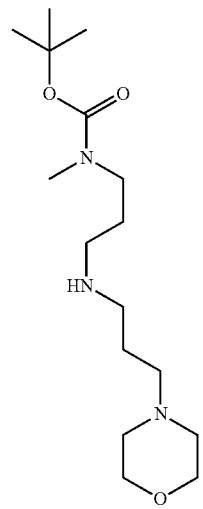 + 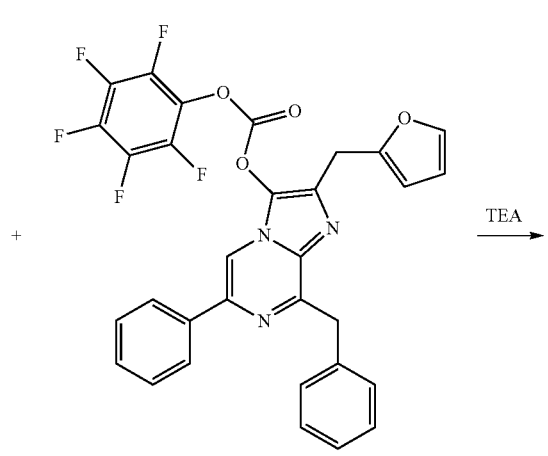

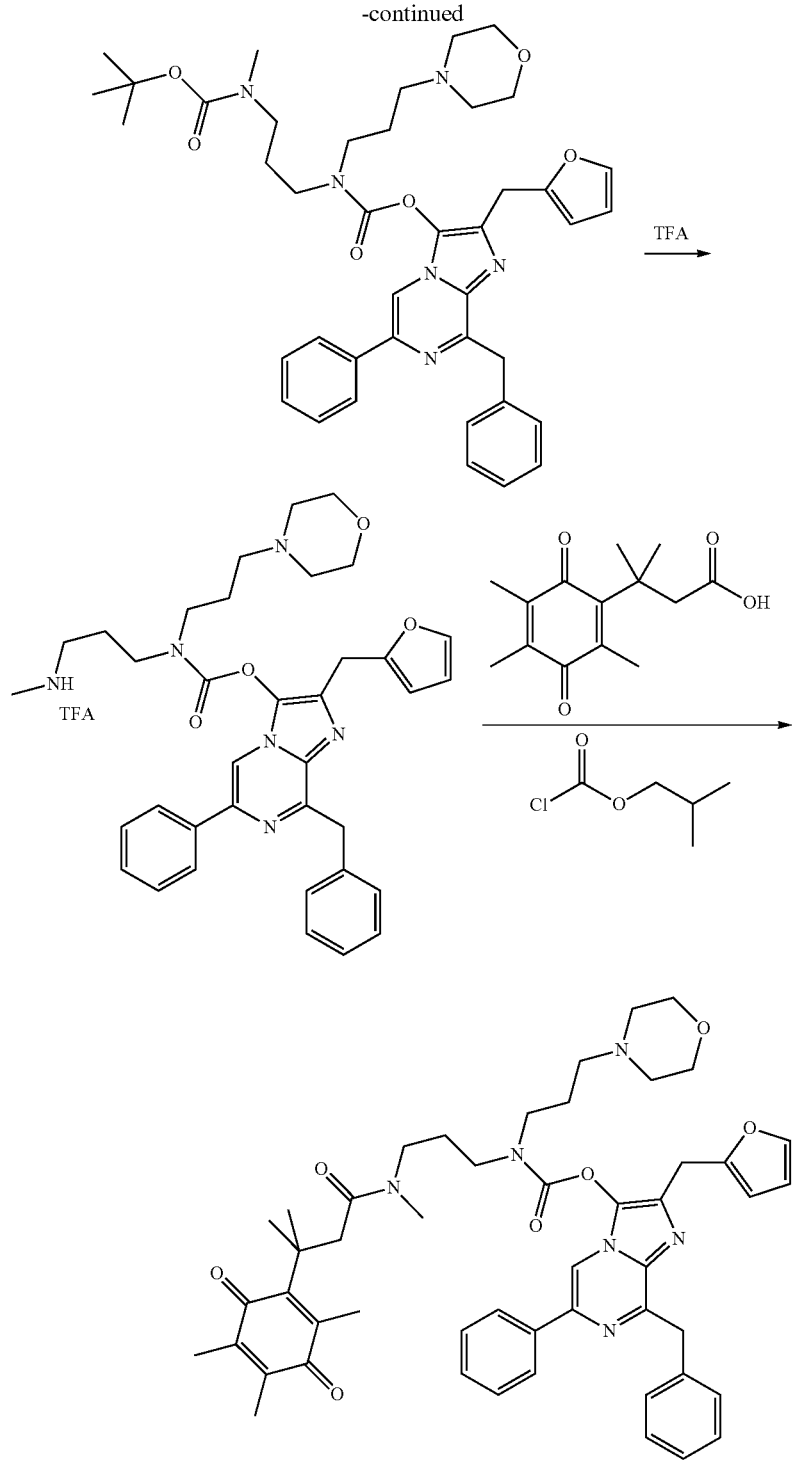

5296

Synthesis of furimazine-[N'-methyl-N'-Boc-N-(3-morpholinopropyl)propane-1,3-diamine]carbamate To the mixture of furimazine (300 mg, 0.788 mmol) and bis(pentafluorophenyl)dicarbonate (380 mg, 0.867 mmol) in 20 ml of dry THF, TEA (160 mg, 1.58 mmol) was added at room temperature under argon. The mixture was stirred for 2-3 minutes, and tert-butyl methyl(3-((3-morpholinopropyl) amino)propyl) carbamate (0.497 g, 0.512 mmol) was added. The resultant mixture was stirred at room temperature for 30 minutes. The compound was purified by flash column chromatography using heptane/ethyl acetate/THF as eluent to give the product in a yield of 72.3%. $^1$H NMR (300 MHz, $CD_2Cl_2$) δ ppm: 7.9-8.0 (m, 3H), 7.53 (d, 2H), 7.2-7.5 (m, 7H), 6.34 (m, 1H, furan), 6.13 (d, 1H, furan), 4.59 (s, 2H, $CH_2$Ph), 4.18 (s, 2H, $CH_2$Ph), 3.66 (m, 4H, $CH_2$O), 3.20-

3.56 (m, 6H), 2.84 (d, 3H, NCH$_3$), 2.3-2.5 (m, 6H), 1.79-2.0 (m, 4H, CH$_2$), 1.41 (s, 9H, CH$_3$); MS-ESI (m/e): 723.59 [M+H]$^+$.

Synthesis of #5296

5296 was prepared by employing the above method used for the synthesis of #5295. MS-ESI (m/e): 855.38 [M+H]$^+$.

Example 3

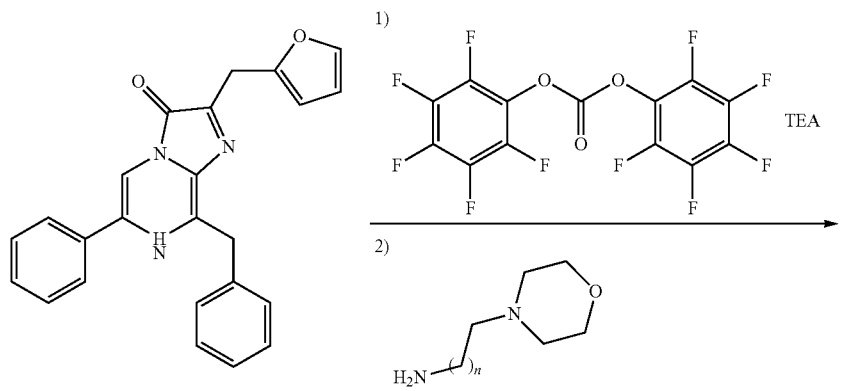
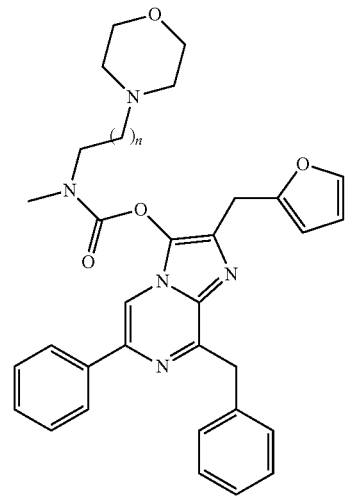

5396: n = 1;
5393: n = 2;
5394: n = 3.

Synthesis of 5393

Bis(pentafluorophenyl) carbonate (77 mg, 0.20 mmol) and triethylamine (40 mg, 0.39 mmol) were added to a solution of 8-benzyl-2-(furan-2-ylmethyl)-6-phenyl-1,7-dihydroimidazo[1,2-a]pyrazin-3(2H)-one (50 mg, 0.13 mmol) in THF consecutively under nitrogen with an ice-water bath. The mixture was stirred for 5 min, N-methyl-3-morpholin-4-ylpropan-1-amine (HCl salt, 38 mg, 0.20 mmol) was added, and the mixture was stirred for another 10 min. After TLC showed the disappearance of the starting material, the solvent was removed, and the residue was purified by flash chromatography to give the product as a yellowish solid. (42 mg, 57%). $^1$H NMR (300 MHz, CD$_2$Cl$_2$, δ): 7.86 (m, 3H), 7.17 (m, 8H), 6.87 (s, 1H), 6.23 (s, 1H), 6.02 (s, 1H), 4.48 (s, 2H), 4.08 (s, 3H), 3.60 (m, 6H), 3.35 (m, 2H), 2.41 (m, 6H), 1.74 (m, 2H). MS (ESI) m/z: 566.5.

Example 4

Synthesis of 5396

Followed the same procedure as used for 5393. $^1$HNMR (300 MHz, CD$_2$Cl$_2$, δ): 7.96 (m, 3H), 7.32 (m, 8H), 6.97 (s, 1H), 6.32 (s, 1H), 6.12 (s, 1H), 5.02 (s, 2H), 4.58 (s, 3H), 3.69 (m, 6H), 3.35 (m, 2H), 2.55 (m, 6H), 1.83 (m, 2H), 1.28 (m, 2H). MS (ESI) m/z: 580.5.

Example 5

Synthesis of 5394

Followed the same procedure as used for 5393. $^1$HNMR (300 MHz, CD$_2$Cl$_2$, δ): 7.39 (m, 11H), 6.97 (s, 1H), 6.28 (s, 1H), 6.13 (s, 1H), 5.02 (s, 2H), 4.58 (s, 3H), 3.69 (m, 6H), 3.46 (m, 2H), 2.59 (m, 2H). MS (ESI) m/z: 551.5.

Example 6

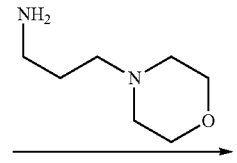
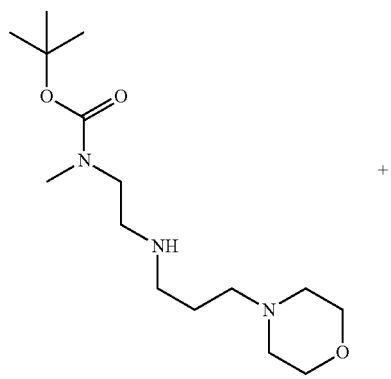

-continued

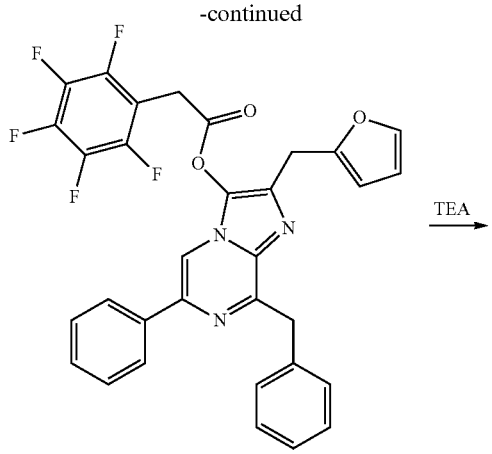

Synthesis of N'-methyl-N'-Boc-N-(3-morpholino-propyl)ethylenediamine

To a solution of morpholine propylamine (0.50 g, 3.46 mmol) in 40 ml of anhydrous methanol, 3-(N-methyl-N-Boc) acetaldehyde (0.6 g, 3.46 mmol) was added. The mixture was stirred at room temperature for 3 hours. NaBH$_4$ (0.393 g, 10.39 mmol) was added to the mixture at 0° C., and the resultant mixture was stirred at 0° C. for 1 hour and 1 hour at room temperature. The reaction was quenched by adding 5 ml of water. After removal of solvent, 10 ml of water was added to the residue. The mixture was extracted three times with methylene chloride, and the combined organic layer was dried over Na$_2$SO$_4$. The desired product was obtained after evaporating the solvent, and without further purification the product was used directly in the next step.

Synthesis of #5416

To the mixture of furimazine (250 mg, 0.657 mmol) and bis(pentafluorophenyl) dicarbonate (0.317 mg, 0.722 mmol) in 20 ml of dry THF, TEA (73 mg, 0.512 mmol) was added at room temperature under argon. The mixture was stirred for 2-3 minutes, and tert-butyl methyl(3-((3-morpholinopropyl) aminoethyl)) carbamate (0.396 g, 1.31 mmol) was added. The resultant mixture was stirred at room temperature for 30 minutes. The compound was purified by flash column chromatography using heptane/ethyl acetate/THF as eluent and gave the product in a yield of 76.4% (0.356 g). $^1$H NMR (300 MHz, CD$_2$Cl$_2$) δ ppm: 7.9-8.0 (m, 3H), 7.58 (d, 2H), 7.2-7.5 (m, 7H), 6.36 (m, 1H, furan), 6.15 (dd, 1H, furan), 4.59 (s, 2H, CH$_2$Ph), 4.20 (d, 2H, CH$_2$Ph), 3.67 (m, 4H, CH$_2$O), 3.30-3.60 (m, 6H), 2.87 (s, 3H, NCH$_3$), 2.3-2.5 (m, 6H), 1.6-2.0 (m, 2H, CH$_2$), 1.44 (s, 9H, CH$_3$); MS-ESI (m/e): 709.62 [M+H]$^+$.

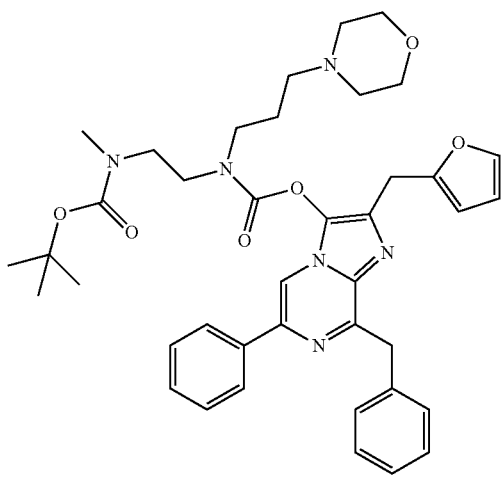

5416

Example 7

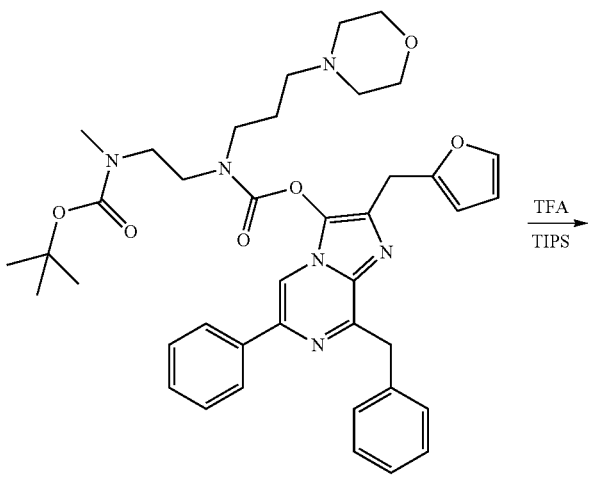

5416

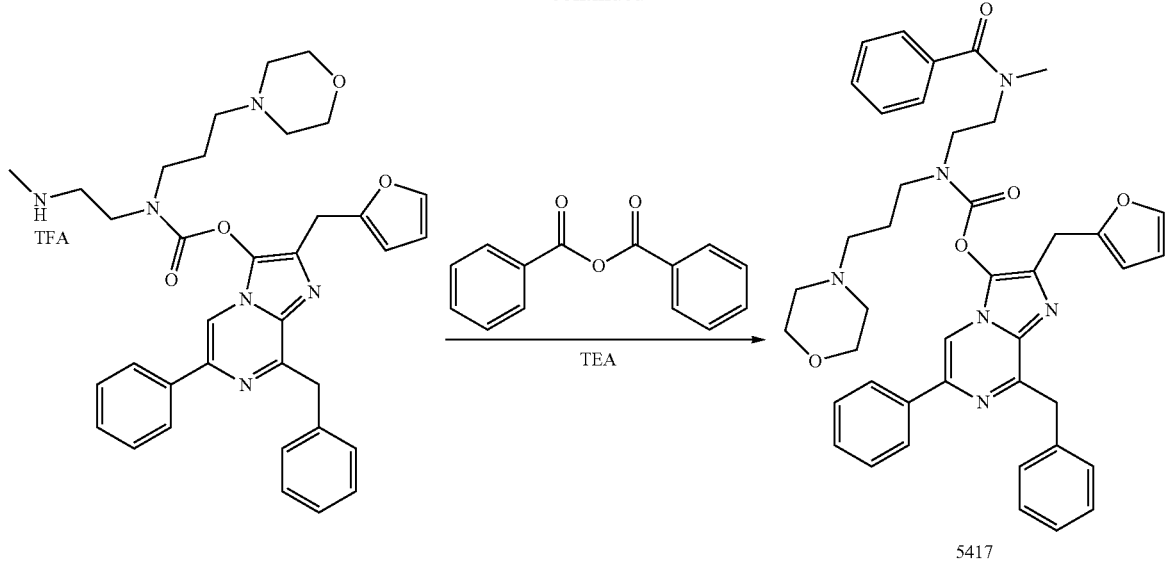

Synthesis of furimazine-[N'-methyl-N-(3-morpholinopropyl)ethylenediamine]carbamate Furimazine-[N'-methyl-N'-Boc-N-(3-morpholinopropyl) ethylenediamine]carbamate #5416 (0.350 g, 0.494 mmol) and triisopropylsilane (100 ul) were dissolved in 20 ml of methylene chloride and TFA (1:1 in volume) and the mixture was stirred at room temperature for 2 hours. After removal of the solvent, the residue was dried under high vacuum overnight, and the product was used directly in the next step.

Synthesis of #5417

To the mixture of furimazine-[N'-methyl-N-(3-morpholinopropyl)carbamate (0.0563 mmol) and benzoic anhydride (63 mg, 0.282 mmol) in 10 ml of dry THF, TEA at room temperature was added. The resultant mixture was stirred at room temperature for 1 hour. The compound was directly purified with flash silica column using heptane and ethyl acetate as eluent in a yield of 75% (30 mg). MS-ESI (m/e): 713.5 [M+H]$^+$.

Example 8

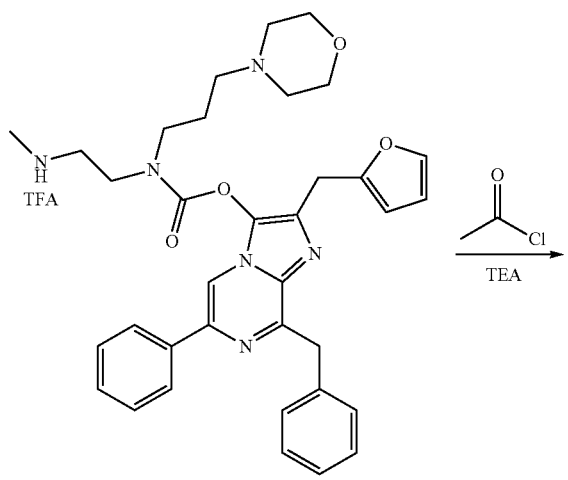

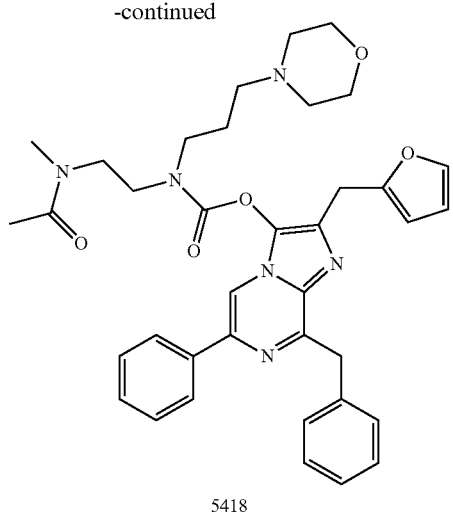

Synthesis of #5418

To the mixture of furimazine-[N'-methyl-N-(3-morpholinopropyl)ethylenediamine]carbamate (0.0563 mmol) and acetyl chloride (44 mg, 0.282 mmol) in 10 ml of dry THF, TEA at room temperature was added. The resultant mixture was stirred at room temperature for 1 hour. The compound was directly purified with flash silica column chromatography using heptane and ethyl acetate as eluent and gave a yield of 68% (25 mg). MS-ESI (m/e): 651.5 [M+H]$^+$.

Example 9

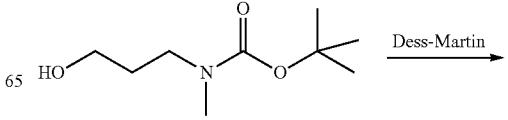

-continued

1)

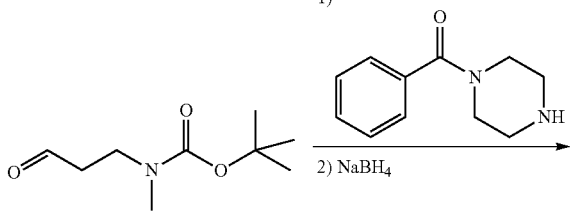

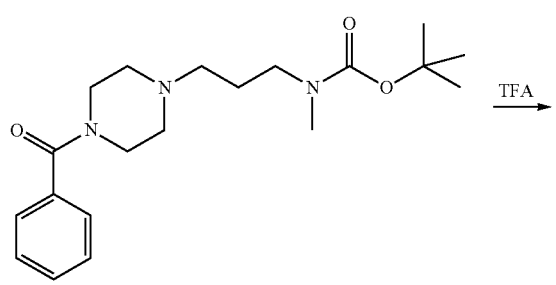

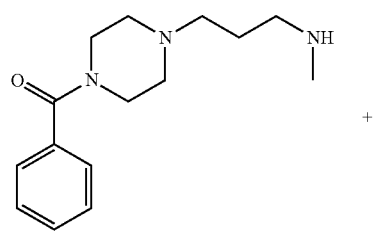

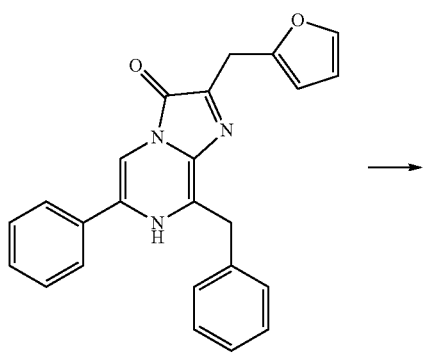

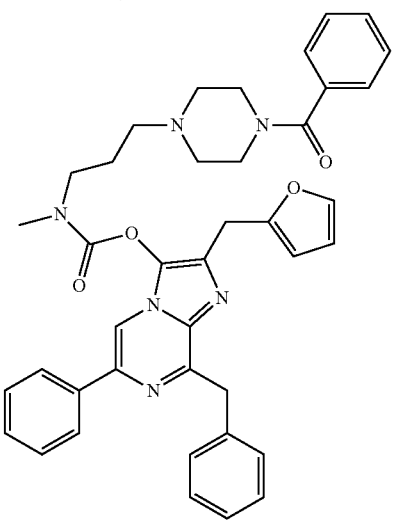 [SMILES: CN(CCCN1CCN(C(=O)c2ccccc2)CC1)C(=O)Oc1c(Cc2ccco2)nc2c(Cc3ccccc3)nc(-c3ccccc3)cn12]

Synthesis of tert-butyl methyl(3-oxopropyl)carbamate

To a solution of N-Methyl-N-boc-aminopropan-3-ol (5.55 g, 29.3 mmol) in dichloromethane (100 ml), Dess-Martin periodinane (14.93 g, 35.2 mmol) was added. The reaction mixture was stirred at room temperature for two hours. The resulting mixture was then washed with saturated sodium thiosulfate solution, saturated potassium carbonate solution and brine. The organic layers were collected and dried over sodium sulfate. The solvent was removed, and the residue was purified by flash chromatography to give the product as a clear oil (3.5 g, 64%). $^1$HNMR (300 MHz, CD$_2$Cl$_2$, δ): 9.78 (s, 1H), 3.52 (t, J=9.0 Hz, 2H), 2.84 (s, 3H), 2.65 (m, 2H), 1.44 (s, 9H).

Synthesis of tert-butyl (3-(4-benzoylpiperazin-1-yl)propyl)(methyl)carbamate

To a solution tert-butyl methyl(3-oxopropyl)carbamate (0.57 g, 3.29 mmol) in methanol (20 ml), 1-Benzoylpiperazine (0.63 g, 3.29 mmol) was added. The reaction mixture was stirred for an hour, and sodium borohydride (0.25 g, 6.58 mmol) was added. The mixture was then stirred for another 4 h and extracted with ethyl acetate/water. The organic layer was collected and dried over sodium sulfate. The solvent was evaporated, and the residue was purified by flash chromatography to give the product as a white solid (0.84 g, 70%). $^1$HNMR (300 MHz, CD$_2$Cl$_2$, δ): 7.41 (m, 5H), 3.50 (m, 4H), 3.24 (t, J=6.0 Hz, 2H), 2.83 (s, 3H), 2.36 (m, 6H), 1.69 (m, 2H), 1.43 (s, 9H).

Synthesis of (4-(3-(methylamino)propyl)piperazin-1-yl)(phenyl)methanone

Tert-Butyl (3-(4-benzoylpiperazin-1-yl)propyl)(methyl) carbamate (0.8 g, 2.2 mmol) was dissolved in dichloromethane (15 ml). Trifluoroacetic acid (5 ml) and a few drops of triisopropylsilane were added consecutively. The resulting mixture was then stirred for 1 h. Solvent was evaporated, and the residue was used in the next step without further purification.

Synthesis of 5422

Followed the same procedure as used for 5393. $^1$HNMR (300 MHz, CD$_2$Cl$_2$, δ): 7.95 (m, 2H), 7.42 (m, 12H), 6.97 (s, 5H), 5.02 (s, 3H), 4.58 (s, 2H), 3.71 (m, 6H), 3.05 (m, 2H), 1.82 (m, 4H). MS (ESI) m/z: 669.5

Example 10

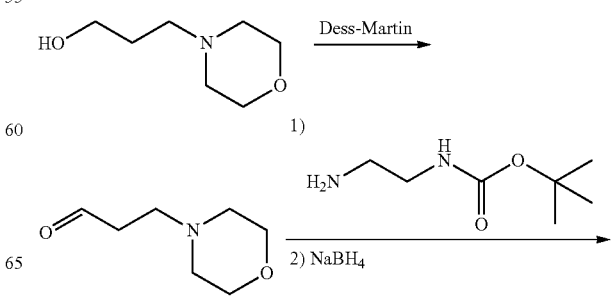

88

Example 11

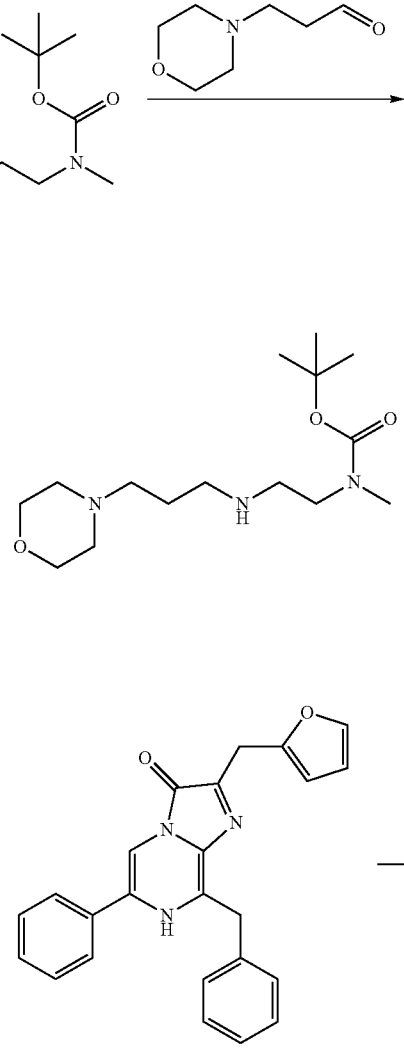

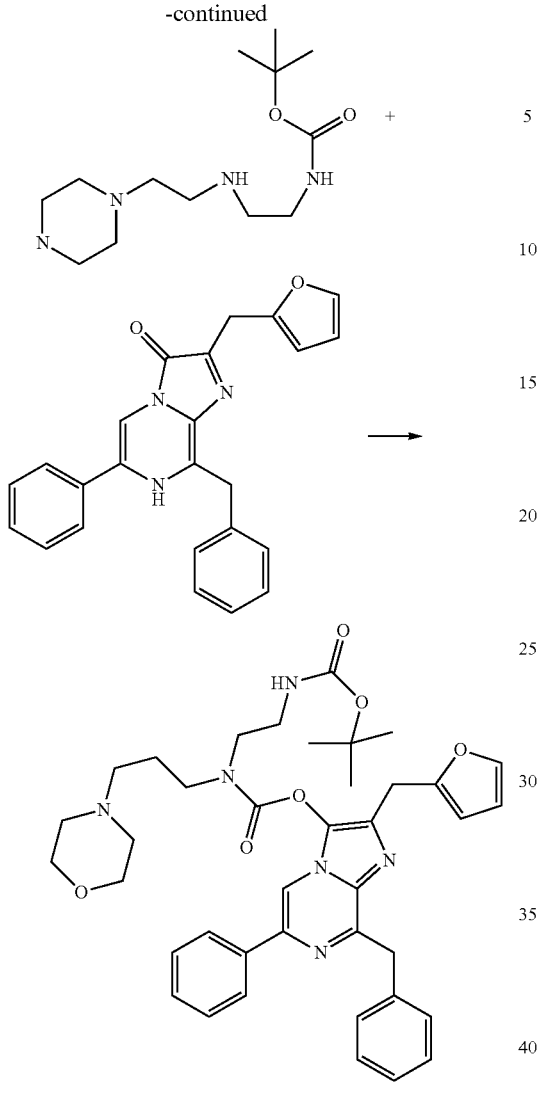

5450

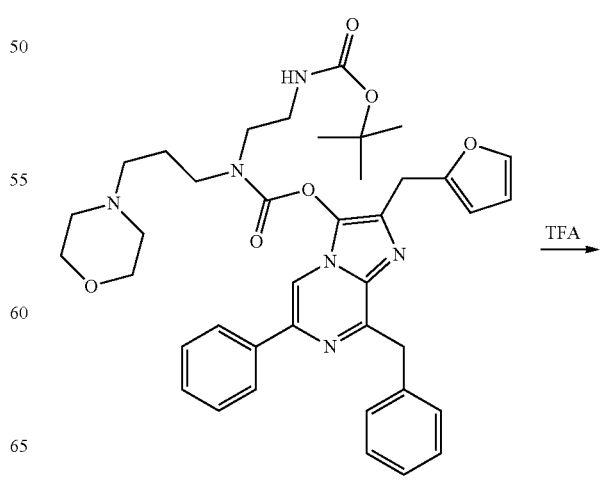

Synthesis of 3-morpholinopropanal

Followed the same procedure as used for the synthesis of 3-[(N-methyl-N-Boc]propanal ("1307-84"). Crude product was directly used in the next step.

Synthesis of tert-butyl (2-((2-morpholinoethyl)amino)ethyl)carbamate

Followed the same procedure as used for 1307-84. Crude product was directly used in the next step.

Synthesis of 5450

Followed the same procedure as used for 5393. $^1$HNMR (300 MHz, CD$_2$Cl$_2$, δ): 8.03 (m, 2H), 7.34 (m, 12H), 4.58 (s, 2H), 4.18 (s, 2H), 3.66 (m, 6H), 3.46 (m, 2H), 3.06 (m, 6H), 2.43 (m, 6H), 1.91 (m, 2H), 1.42 (s, 9H). MS (ESI) m/z: 695.5.

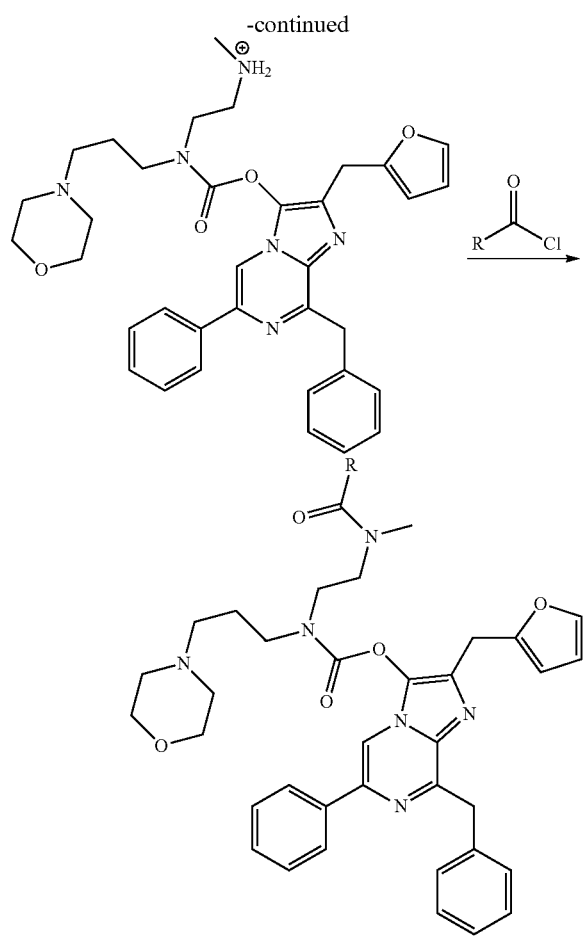

(methyl)amino)ethyl)(3-morpholinopropyl)carbamate (1328-19) (90 mg, 0.13 mmol) in dichloromethane (5 ml), trifluoroacetic acid (1 ml) and a few drops of triisopropylsilane was added. The reaction mixture was stirred for an hour. Solvent was evaporated, and the residue was dried by high vacuum. Dichloromethane (5 ml) was added to the residue followed by 4-methoxybenzoyl chloride (43.3 mg, 0.25 mmol). Triethylamine (0.18 ml, 1.27 mmol) was then added slowly, and the resulting mixture was stirred for another hour. Solvent was removed, and the residue was purified by flash chromatography to give the product as a yellowish solid (40 mg, 43%). MS (ESI) m/z: 743.5.

Synthesis of 5452

Followed the same procedure as used for 5393. $^1$HNMR (300 MHz, CD$_2$Cl$_2$, δ): 7.53 (m, 18H), 5.02 (s, 2H), 4.55 (m, 2H), 3.68 (m, 8H), 2.91 (m, 5H), 2.49 (m, 8H), 1.43 (m, 2H); FNMR (300 MHz, CD$_2$Cl$_2$, δ): −61.17 (s); MS (ESI) m/z: 781.4.

Synthesis of 5453

Followed the same procedure as used for 5393. $^1$HNMR (300 MHz, CD$_2$Cl$_2$, δ): 8.18 (m, 2H), 7.40 (m, 12H), 5.02 6.97 (m, 2H), 4.58 (s, 2H), 4.16 (m, 2H), 3.67 (m, 6H), 3.09 (m, 5H), 2.41 (m, 7H), 1.28 (m, 2H), 1.15 (m, 6H); MS (ESI) m/z: 679.5.

Synthesis of 5454

Followed the same procedure as used for 5393. $^1$HNMR (300 MHz, CD$_2$Cl$_2$, δ): 7.68 (m, 2H), 7.31 (m, 14H), 6.87 (m, 2H), 4.92 (s, 2H), 4.46 (m, 2H), 3.61 (m, 6H), 2.94 (m, 5H), 2.41 (m, 8H), 1.33 (m, 2H); MS (ESI) m/z: 731.4.

Example 12

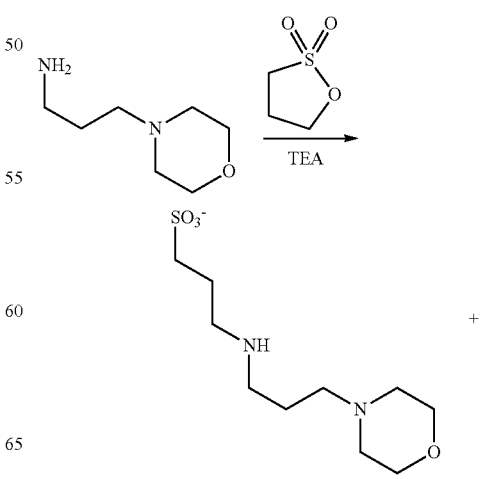

Synthesis of tert-butyl methyl(2-((3-morpholinopropyl)amino)ethyl)carbamate

Followed the same procedure as used for 1307-84. Crude product was directly used in the next step.

Synthesis of 8-benzyl-2-(furan-2-ylmethyl)-6-phenylimidazo[1,2-a]pyrazin-3-yl (2-((tert-butoxycarbonyl)(methyl)amino)ethyl)(3-morpholinopropyl)carbamate. Followed the same procedure as used for 5393. $^1$HNMR (300 MHz, CD$_2$Cl$_2$, δ): 7.95 (m, 2H), 7.28 (m, 12H), 4.48 (s, 2H), 3.62 (m, 6H), 3.36 (m, 7H), 2.79 (m, 2H), 2.47 (m, 6H), 1.91 (m, 2H), 1.42 (s, 9H). MS (ESI) m/z: 709.5.

Synthesis of 5451

To a solution of 8-benzyl-2-(furan-2-ylmethyl)-6-phenylimidazo[1,2-a]pyrazin-3-yl (2-((tert-butoxycarbonyl)

-continued

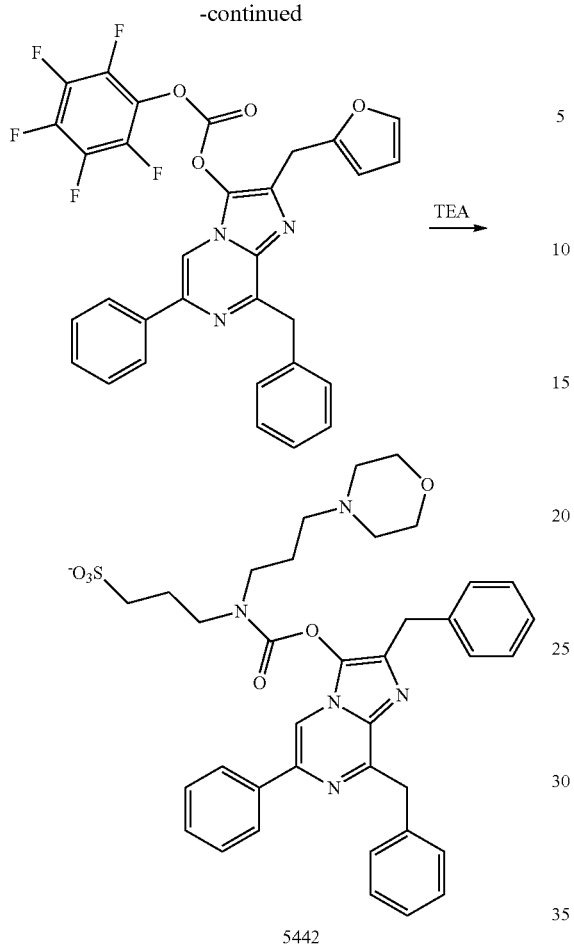

5442

Synthesis of 3-((3-morpholinopropyl)amino)propane-1-sulfonate

A mixture 3-morpholinopropan-1-amine (1.0 g, 6.93 mmol), 1,3-propane sultone (0.846 g, 6.93 mmol) and TEA (0.701 g, 6.93 mmol) in 50 ml of iosopropanol was refluxed for two days. The solvent was removed, the residue was triturated with ether, and then ether was decanted after centrifuge, repeating three times trituration with ether, centrifuge and decanting solvent. The pale white solid was collected, dried under vacuum overnight and used directly in the next step. $^1$H NMR (300 MHz, CD$_2$Cl$_2$) δ ppm: 8.52 (s, 1H), 8.17 (t, 2H), 7.1-7.6 (m, 13H), 4.44 (s, 2H, CH$_2$Ph), 4.08 (s, 2H, CH$_2$Ph), 3.3-3.8 (m, 10H), 2.91 (s, 3H, NCH$_3$), 2.1-2.5 (m, 6H), 1.6-2.0 (m, 4H, CH$_2$); MS-ESI (m/e): 684.39 [M+H]$^+$; HPLC purity: 99.3% at 254 nm.

Synthesis of #5442

To the mixture of coelenterazine HH (300 mg, 0.768 mmol) and bis(pentafluorophenyl) dicarbonate (0.437 mg, 0.998 mmol) in 10 ml of dry THF, TEA (202 mg, 2 mmol) was added at room temperature under argon, the mixture was stirred for 2-3 minutes, and then 3-((3-morpholinopropyl)amino)propane-1-sulfonate (0.611 mg, 2.30 mmol) in 15 ml of DMF was added. The resultant mixture was stirred at room temperature for 1 hour. After removal of solvent under vacuum, the compound was purified by flash column chromatography using heptane/ethyl acetate and methylene chloride/MeOH as eluents and gave a yield of 12.4% (65 mg).

Example 13

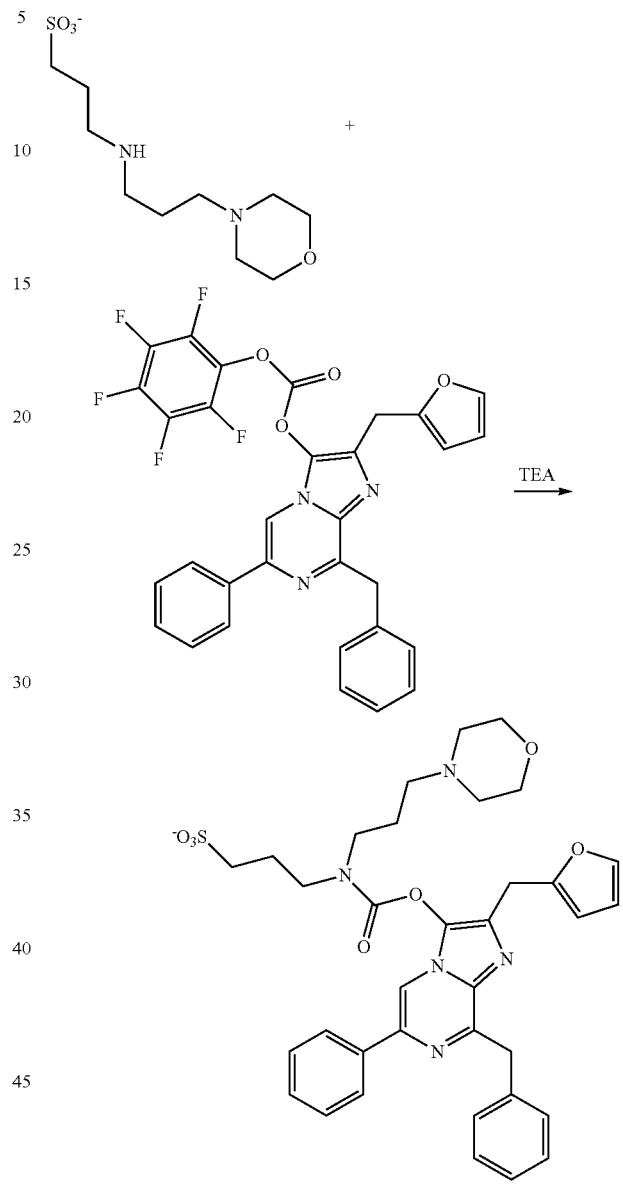

5512

Synthesis of #5512

To the mixture of coelenterazine HH (200 mg, 0.525 mmol) and bis(pentafluorophenyl) dicarbonate (0.276 mg, 0.631 mmol) in 10 ml of dry THF, TEA (0.64 mg, 0.63 mmol) was added at room temperature under argon, the mixture was stirred for 2-3 minutes, and then 3-((3-morpholinopropyl)amino)propane-1-sulfonate (0.418 g, 1.58 mmol) in 10 ml of DMF was added. The resultant mixture was stirred at room temperature for 1 hour. After removal of solvent under vacuum, the compound was purified by flash column chromatography using heptane/ethyl acetate and methylene chloride/MeOH as eluents and gave a yield of 8.5% (30 mg). 674.36 [M+H]$^+$; HPLC purity: 98.2% at 254 nm.

Example 14
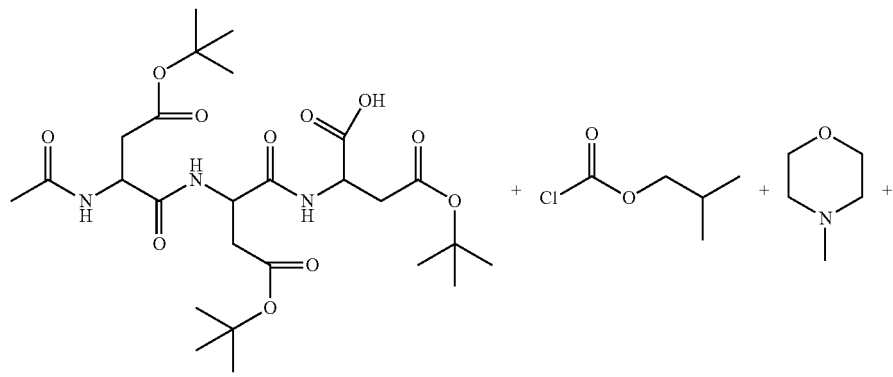
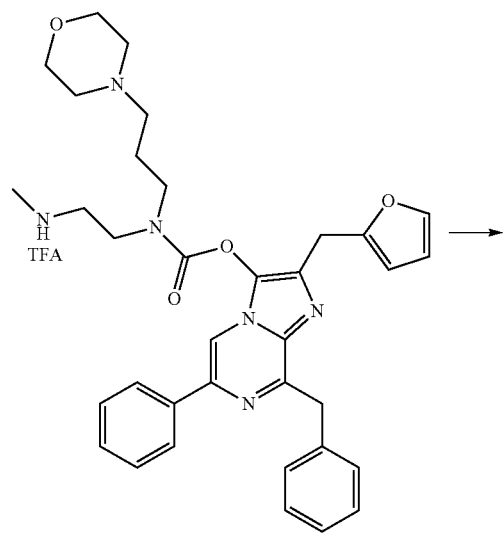
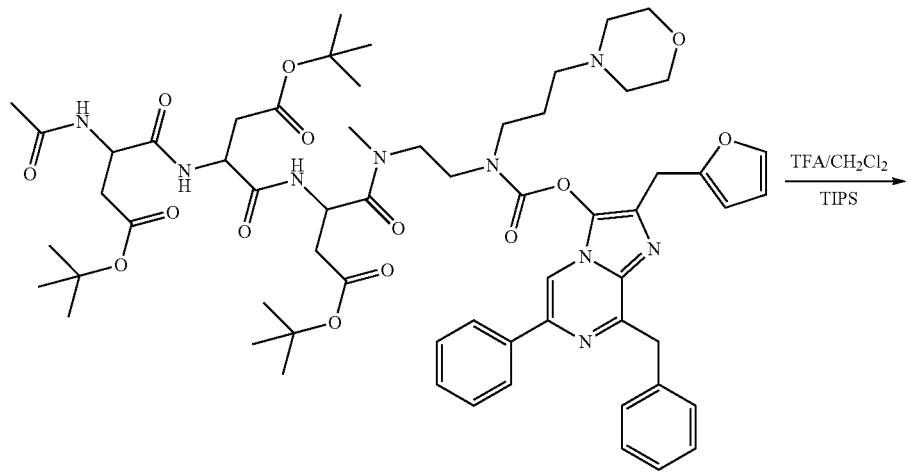

-continued

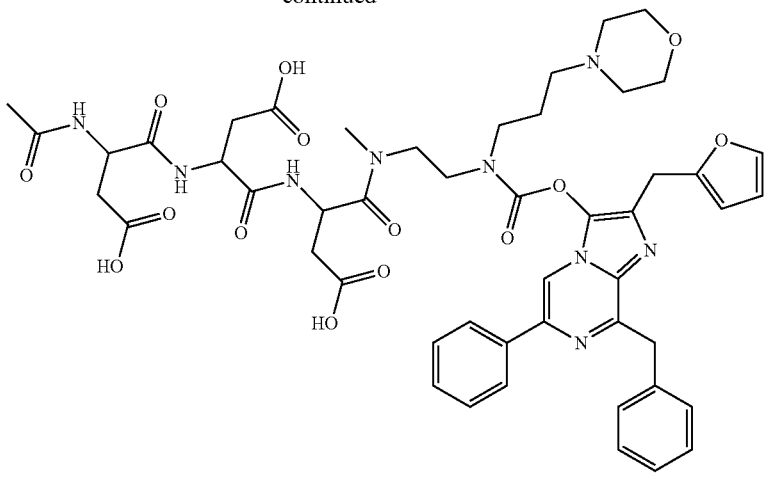

5455

Synthesis of
AcD(tBu)D(tBu)D(tBu)-C2-MOP-furimazine
carbamate

To a solution of AcD(tBu)D(tBu)D(tBu)-COOH (666.7 mg, 1.16 mmol) and isochloroformate (0.158 g, 1.16 mmol) in 40 ml of dry THF, N-methyl morpholine (0.235 g, 2.32 mmol) was added at 0° C. under argon. The mixture was stirred at 0° C. to room temperature for 1 hour, furimazine-[N'-methyl-N-(3-morpholinopropyl)ethylenediamine]carbamate TFA salt (0.21 mg, 0.29 mmol) in 5 ml of methylene chloride was added followed by adding more N-methyl morpholine (0.235 g, 2.32) (Check pH, need to be basic), and the resultant mixture was then stirred for 30 minutes at room temperature. The compound was purified by flash column chromatography using heptane/ethyl acetate and ethyl acetate/THF. The purified compound was then dissolved in 100 ml of methylene chloride, and the solution was washed three times with water to remove N-methyl morpholine HCl salt which might be flushed out by THF solvent from the column. The organic layer was dried with $Na_2SO_4$. After removal of the solvent, the compound was repurified by flash column chromatography using ethyl acetate/THF as eluent to give a yield of 66.4% (0.21 g). MS-ESI (m/e): $[M+H]^+$ 1164.67; HPLC purity: 95.6% at 254 nm.

Synthesis of #5455 (Ac-DDD-MOP-C2-FRZ)

AcD(tBu)D(tBu)D(tBu)-C2-MOP-furimazine carbamate (0.21 g) and triisopropylsilane (0.1 ml) were dissolved in 15 ml of methylene chloride and TFA (1:1 in volume), and the mixture was stirred at room temperature for 4 hours. After removal of the solvent, toluene (20 ml) was added to co-evaporate the residual TFA. The residual solid was triturated three times with ether. After decanting ether, the solid was dried under vacuum. $[M+H]^+$ 996.50; HPLC purity: 95.6% at 254 nm.

Example 15

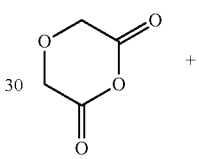

+

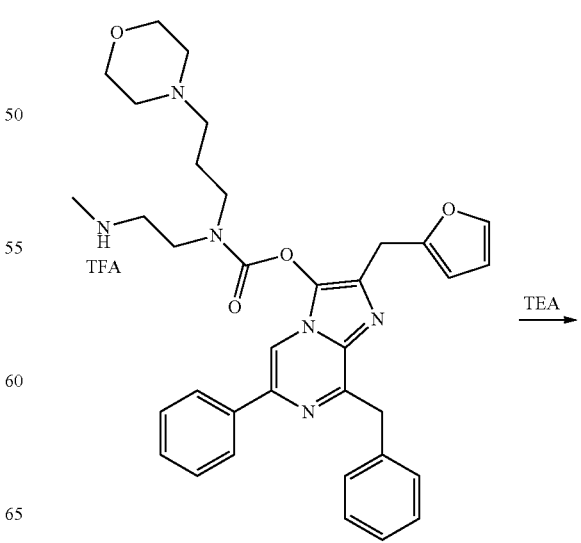

TEA →

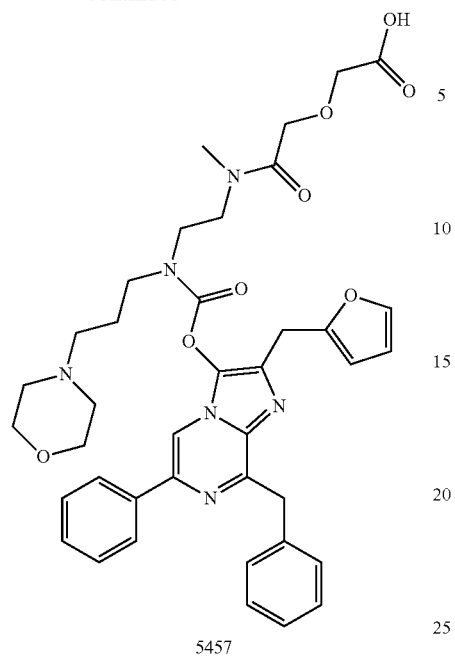

5457

Synthesis of #5457 (COOH-MOP-C2-FRZ)

To the mixture of 1,4-dioxane-2,6-dione (0.25 g, 0.435 mmol) and furimazine-[N'-methyl-N-(3-morpholinopropyl) ethylenediamine]carbamate TFA salt (0.104 g, 0.144 mol) in 20 ml of dry THF, TEA (88 mg, 0.871 mmol) at room temperature was added. The mixture was stirred for 1 hour at room temperature until the starting material amine was completely consumed. (Check pH, basic condition is required and more TEA should be added if needed). The product was purified by flash column chromatography using heptane/ethyl acetate/THF as eluent. MS-ESI (m/e): [M+H]$^+$ 725.44; HPLC purity: 97.8% at 254 nm.

Example 16

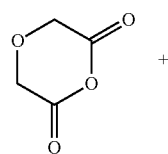

+

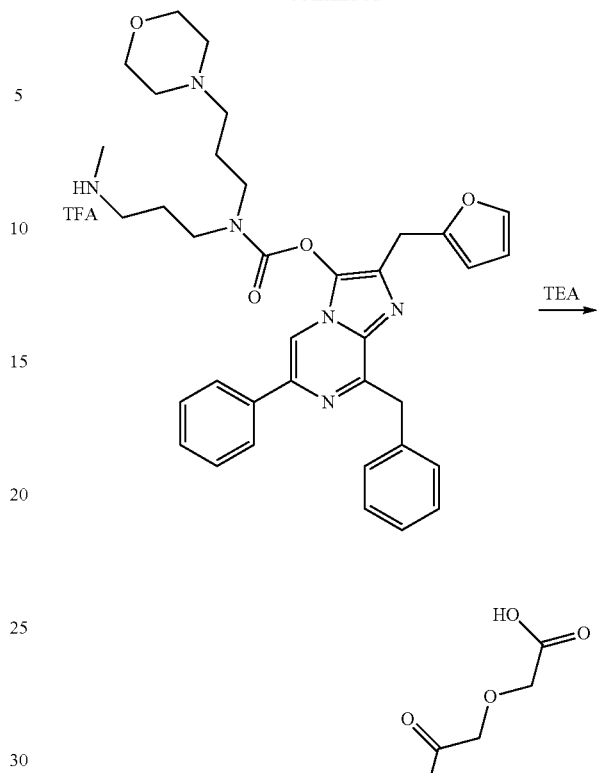

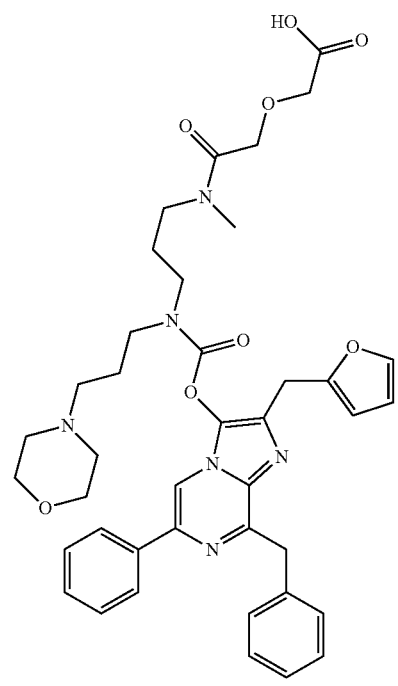

5486

Synthesis of #5486 (COOH-MOP-C3-FRZ)

To the mixture of 1,4-dioxane-2,6-dione (88 mg, 0.760 mmol) and furimazine-[N'-methyl-N-(3-morpholinopropyl) ethylenediamine]carbamate TFA salt (80 mg, 0.109 mmol) in 20 ml of dry THF, TEA (77 mg, 0.76 mmol) at room temperature was added. The mixture was stirred for 1 hour at room temperature until the starting material amine was completely consumed. (Check pH, basic condition is required and more TEA should be added if needed). The product was purified by flash column chromatography using heptane/ethyl acetate/THF as eluent. MS-ESI (m/e): [M+H]$^+$ 739.47; HPLC purity: 85.1% at 254 nm.

Example 17
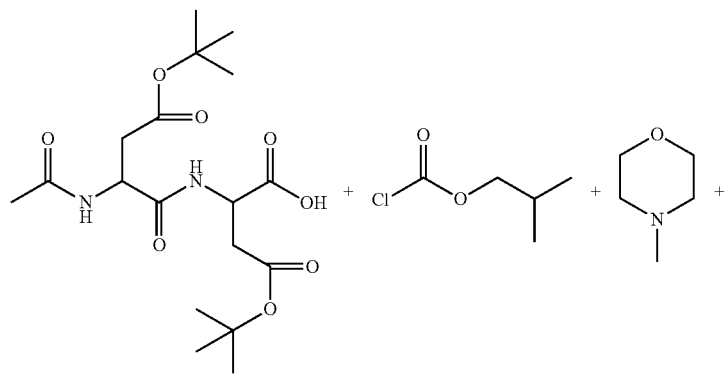
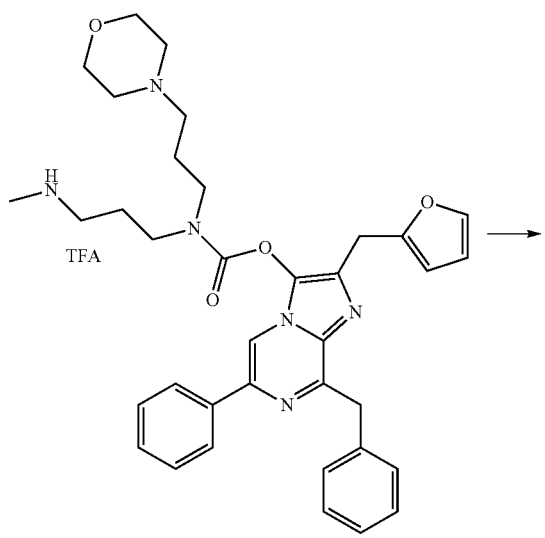
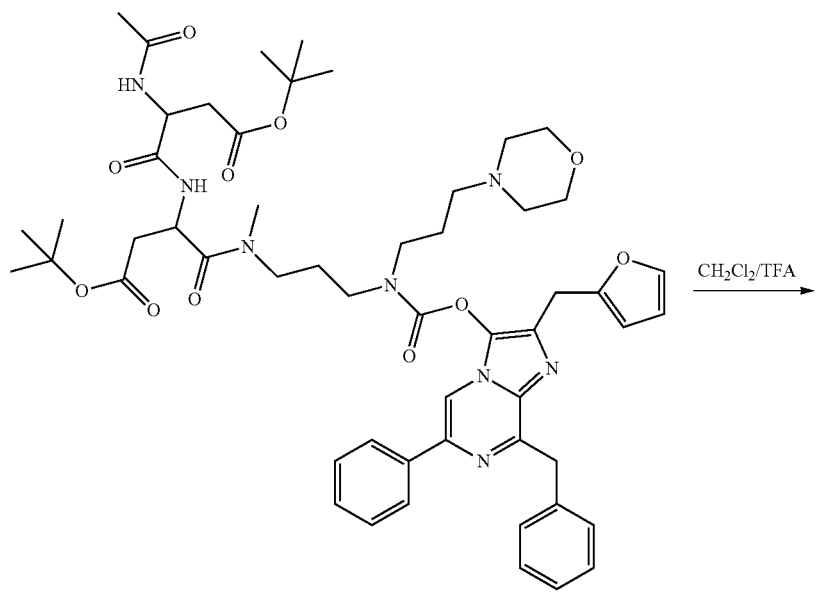

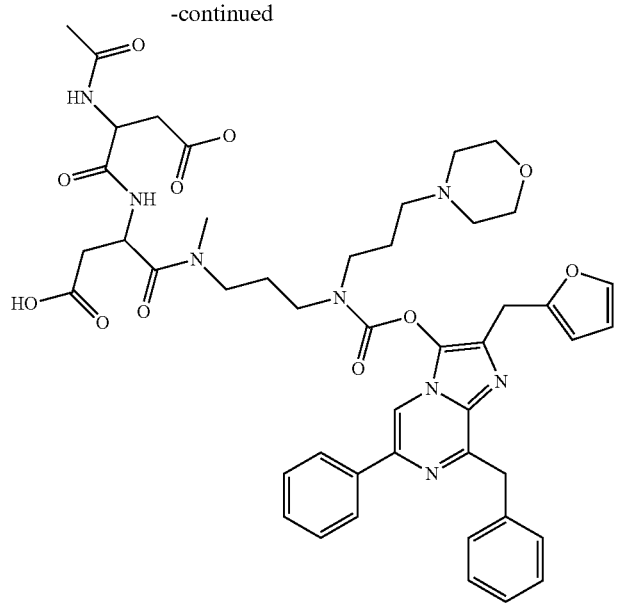

5487

Synthesis of AcD(tBu)D(tBu)-MOP-C3-FRZ

To a solution of AcD(tBu)D(tBu)-COOH (239 mg, 0.593 mmol) and isobutylchloroformate (81 mg, 0.593 mmol) in 40 ml of dry THF, N-methyl morpholine (85.8 mg, 0.848 mmol) at 0° C. was added. The mixture was stirred at 0° C. to room temperature for 1 hour, furimazine-[N'-methyl-N-(3-morpholinopropyl)-1,3-propane-diamine]carbamate TFA salt (125 mg, 0.169 mmol) in 5 ml of methylene chloride was added followed by adding more N-methyl morpholine (86 mg, 0.848 mmol) (Check pH, need to be basic), and the resultant mixture was then stirred for 30 minutes at room temperature. The compound was purified by flash column chromatography using heptane/ethyl acetate and ethyl acetate/THF. The purified compound was then dissolved in 100 ml of methylene chloride, and the solution was washed three times with water to remove N-methyl morpholine HCl salt which might be flushed out by THF solvent from the column. The organic layer was dried with $Na_2SO_4$. After removal of the solvent, the compound was repurified by flash column chromatography using ethyl acetate/THF as eluent to give a yield of 58.2% (0.10 g). MS-ESI (m/e): $[M+H]^+$ 1007.8; HPLC purity: 96.9% at 254 nm.

Synthesis of #5487 (AcDD-MOP-C3-FRZ)

AcD(tBu)D(tBu)-C3-MOP-furimazine carbamate (100 mg) and triisopropylsilane (50 ul) were dissolved in 15 ml of methylene chloride and TFA (1:1 in volume), and the mixture was stirred at room temperature for 4 hours. After removal of the solvent, toluene (20 ml) was added to co-evaporate the residual TFA. The residual solid was triturated three times with ether. After decanting the ether, the solid was dried under vacuum. MS-ESI (m/e): $[M+H]^+$ 895.62; HPLC purity: 98.6% at 254 nm.

Example 18

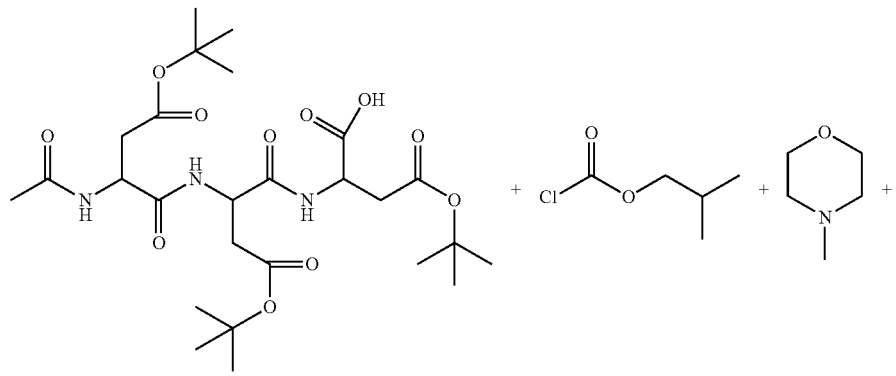

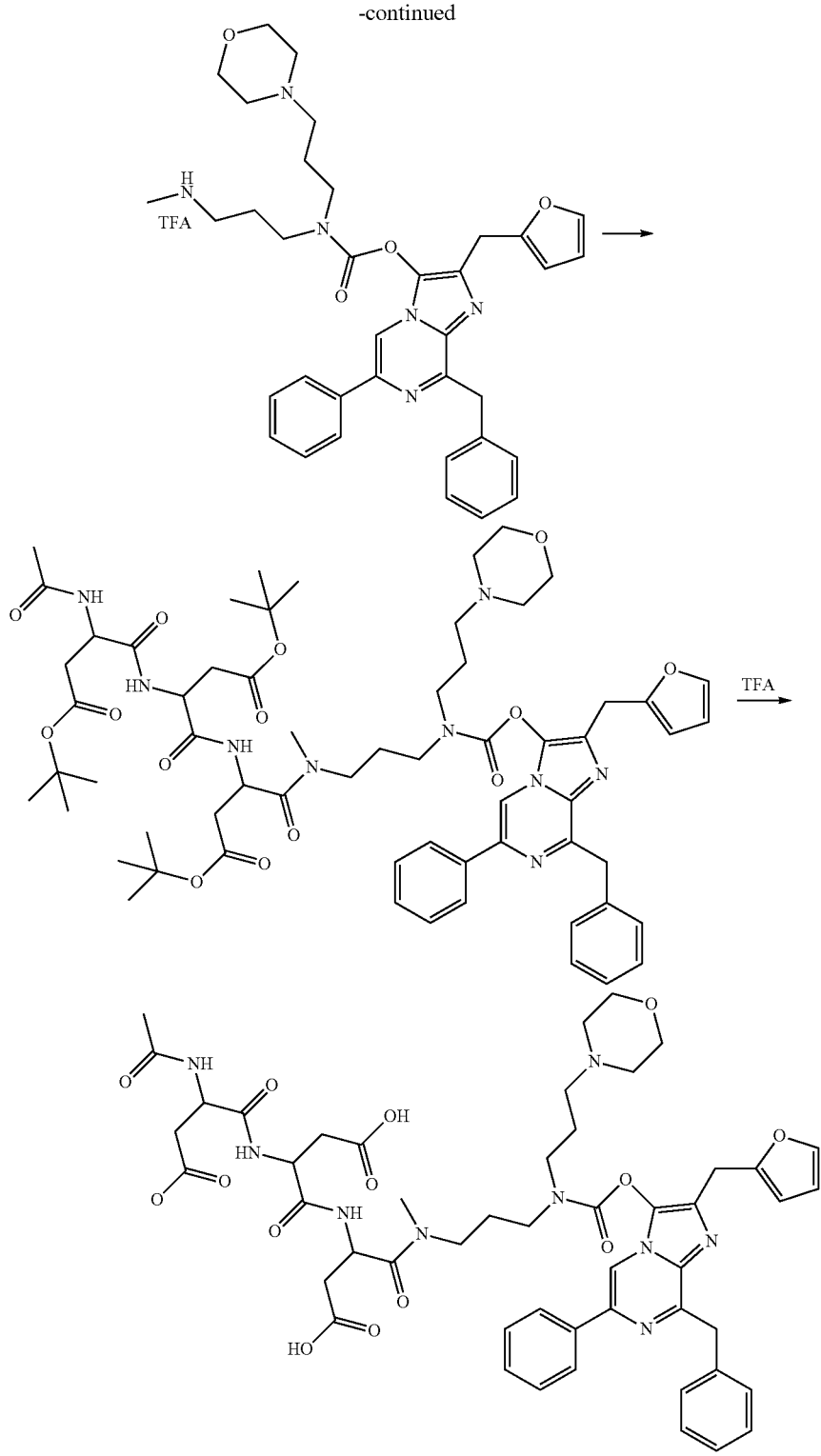

5488

Synthesis of AcD(tBu)D(tBu)D(tBu)-MOP-C3-FRZ

To the solution of AcD(tBu)D(tBu)D(tBu)-COOH (373 mg, 0.651 mmol) and isobutylchloroformate (89 mg, 0.651 mmol) in 40 ml of dry THF, N-methyl morpholine (131 mg, 1.30 mmol) at 0° C. was added. The mixture was stirred at 0° C. to room temperature for 1 hour, furimazine-[N'-methyl-N-(3-morpholinopropyl)-1,3-propane-diamine]carbamate TFA salt (120 mg, 0.162 mmol) in 5 ml of methylene chloride was added followed by adding more N-methyl morpholine (86 mg, 0.848 mmol) (Check pH, need to be basic), and the resultant mixture was then stirred for 30 minutes at room temperature. The compound was purified by flash column chromatography using heptane/ethyl acetate and ethyl acetate/THF. The purified compound was then dissolved in 100 ml of methylene chloride, and the solution was washed three times with water to remove N-methyl morpholine HCl salt which might be flushed out by THF solvent from the column. The organic layer was dried with Na$_2$SO$_4$. After removal of the solvent, the compound was repurified by flash column chromatography using ethyl acetate/THF as eluent to give a yield of 52.1% (0.10 g). MS-ESI (m/e): [M+H]$^+$ 1178.89; HPLC purity: 96.6% at 254 nm.

Synthesis of #5488 (AcDDD-MOP-C3-FRZ)

AcD(tBu)D(tBu)D(tBu)-C3-MOP-furimazine carbamate (100 mg) and triisopropylsilane (50 ul) were dissolved in 15 ml of methylene chloride and TFA (1:1 in volume), and the mixture was stirred at room temperature for 4 hours. After removal of the solvent, toluene (20 ml) was added to co-evaporate the residual TFA. The residual solid was triturated three times with ether. After decanting the ether, the solid was dried under vacuum. MS-ESI (m/e): [M+H]$^+$ 1010.54; HPLC purity: 97.8% at 254 nm.

Example 19

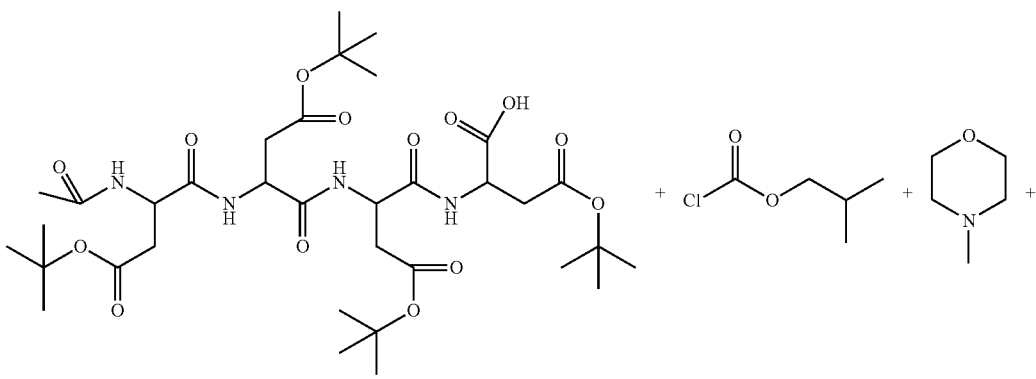

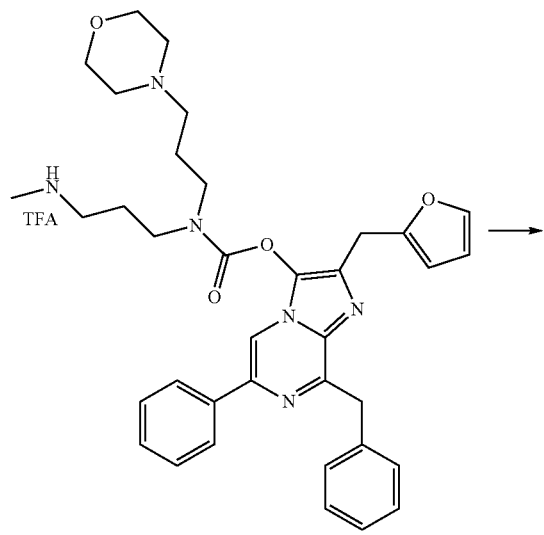

-continued
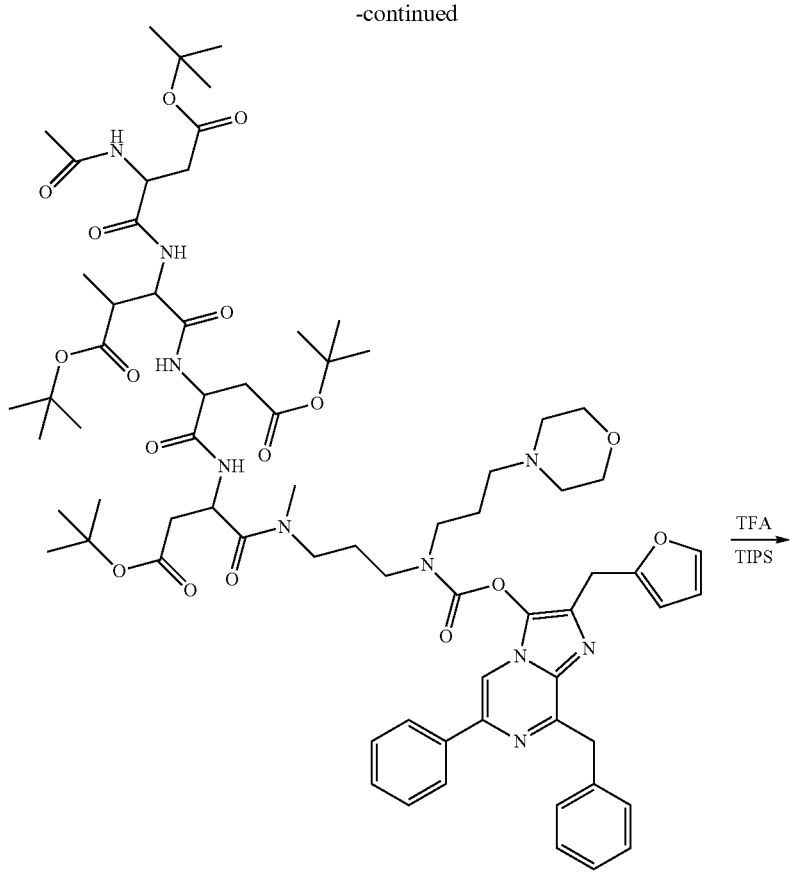
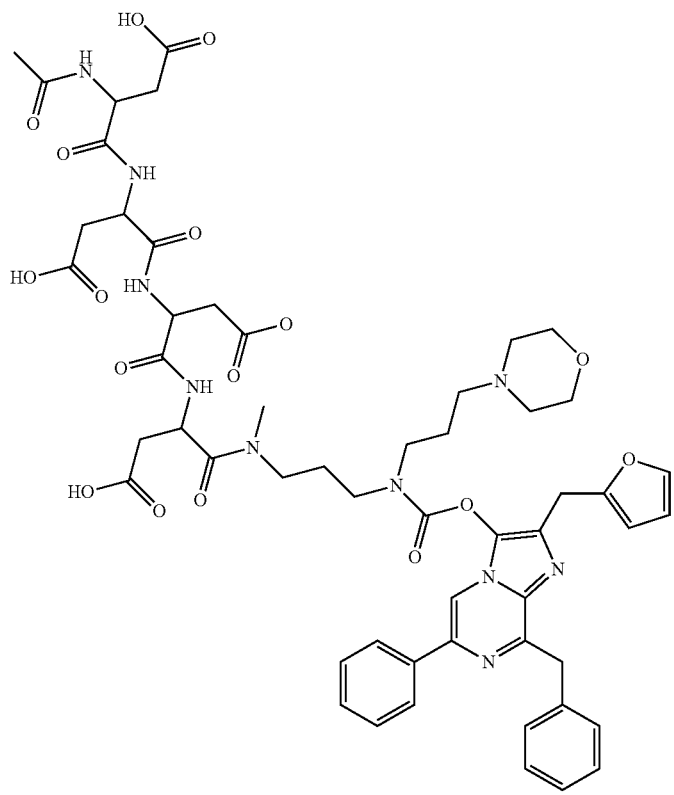

Synthesis of AcD(tBu)D(tBu)D(tBu)D(tBu)-MOP-C3-FRZ

To a solution of AcD(tBu)D(tBu)D(tBu)D(tBu)-COOH (300 mg, 0.403 mmol) and isobutylchloroformate (55 mg, 0.403 mmol) in 30 ml of dry THF was added N-methyl morpholine (81.5 mg, 0.805 mmol) at 0° C. The mixture was stirred at 0° C. to room temperature for 1 hour, furimazine-[N'-methyl-N-(3-morpholinopropyl)-1,3-propane-diamine] carbamate TFA salt (74.2 mg, 0.1 mmol) in 5 ml of methylene chloride was added followed by adding more N-methyl morpholine (86 mg, 0.848 mmol) (Check pH, need to be basic), and the resultant mixture was then stirred for 30 minutes at room temperature. The compound was purified by flash column chromatography using heptane/ethyl acetate and ethyl acetate/THF and gave a yield of 58.8% (80 mg).

Synthesis of #5489 (AcDDDD-MOP-C3-FRZ)

AcD(tBu)D(tBu)D(tBu)D(tBu)-C3-MOP-furimazine carbamate (80 mg) and triisopropylsilane (50 ul) were dissolved in 15 ml of methylene chloride and TFA (1:1 in volume), and the mixture was stirred at room temperature for 4 hours. After removal of the solvent, toluene (20 ml) was added to co-evaporate the residual TFA. The residual solid was triturated three times with ether. After decanting the ether, the solid was dried under vacuum. MS-ESI (m/e): [M+H]/2 563.45; HPLC purity: 84.9% at 254 nm.

Example 20

PBI-5512, PBI-5455, PBI-5487, PBI-5488 in HeLa Cells

Figure 2:
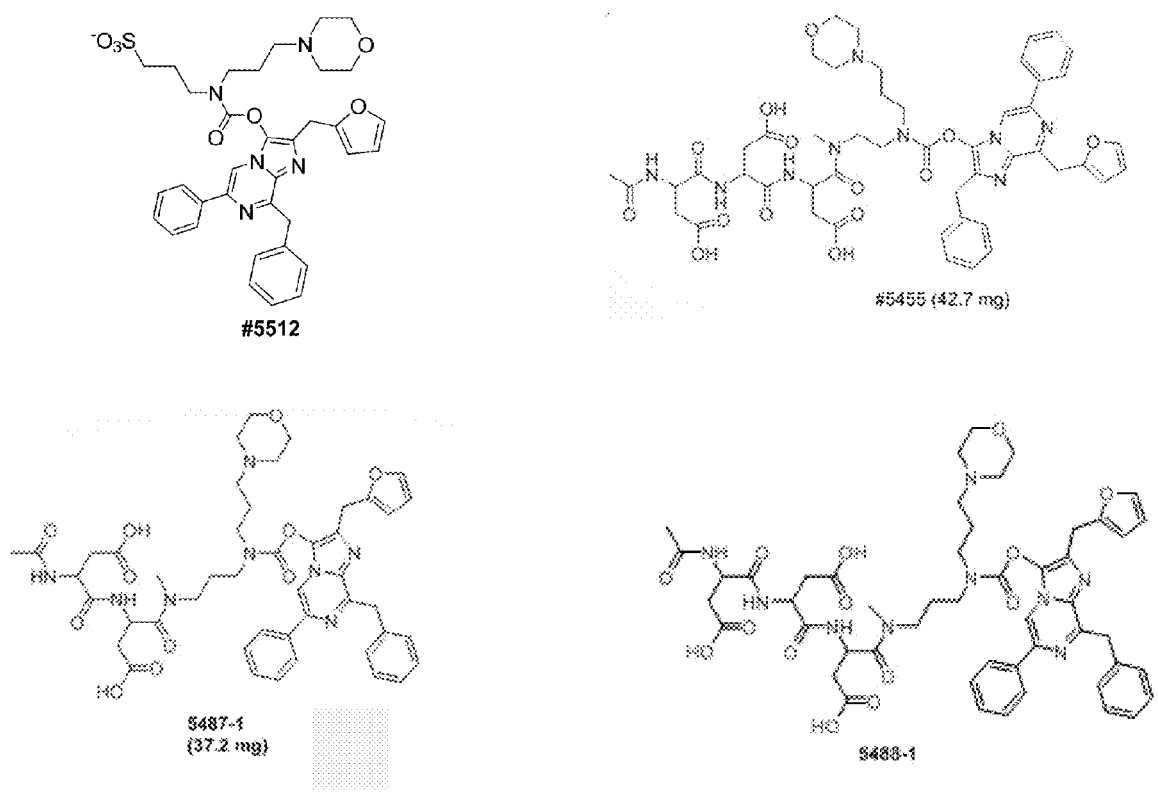
FIG. 2 depicts compounds PBI-5512, PBI-5455, PBI-5487 and PBI-5488, which were added to cells expressing a coelenterazine-utilizing luciferase and luminescence was detected.
Figure 3A:
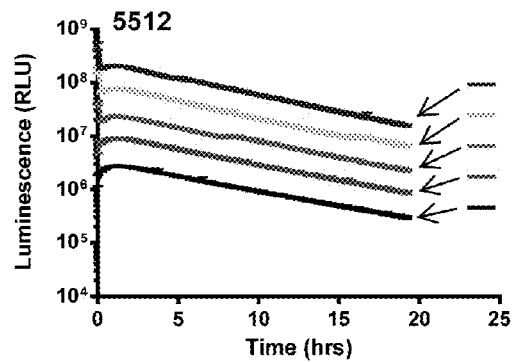
FIGS. 3A-3D depict the ability of the disclosed compounds to act as pro-substrates. Compounds PBI-5512, PBI-5455, PBI-5487 and PBI-5488 were added to cells (3A-D, respectively) expressing a coelenterazine-utilizing luciferase, NANOLUC®, and luminescence detected. See Example 20.
Figure 3B:
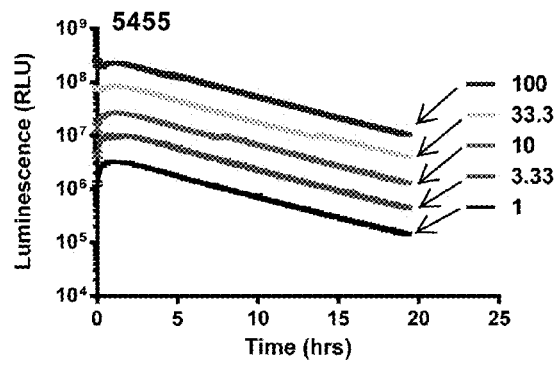
Figure 3C:
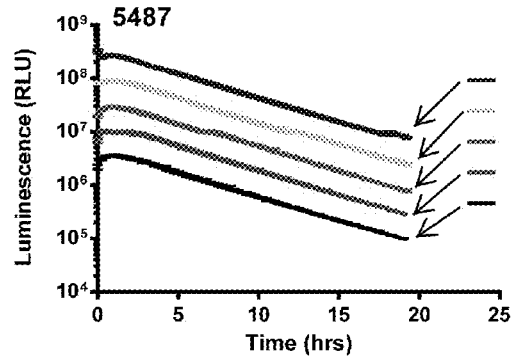
Figure 3D:
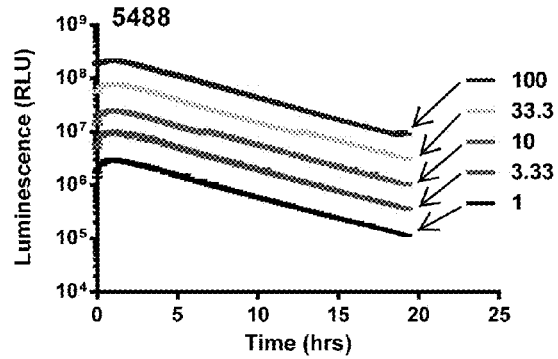
Figure 4A:
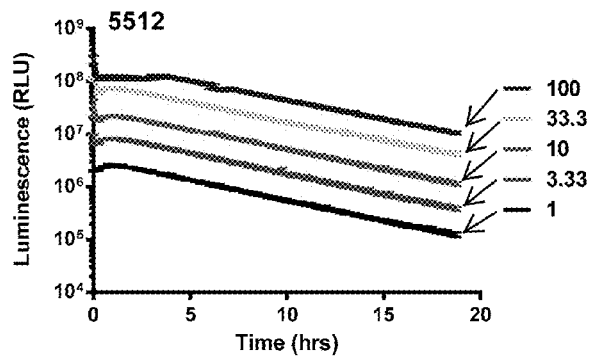
FIGS. 4A-4D depict the ability of the disclosed compounds to act as pro-substrates. Compounds PBI-5512, PBI-5455, PBI-5487 and PBI-5488 were added to cells (4A-D, respectively) expressing a coelenterazine-utilizing luciferase, NANOLUC®, and luminescence detected. See Example 20.
Figure 4B:
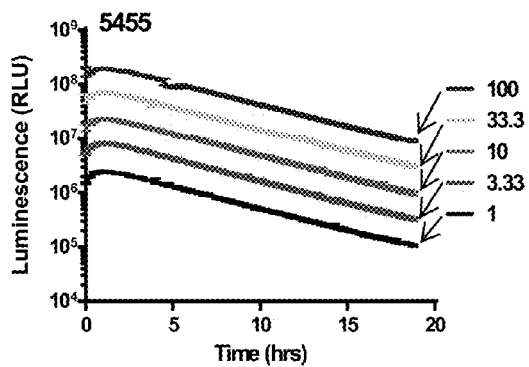
Figure 4C:
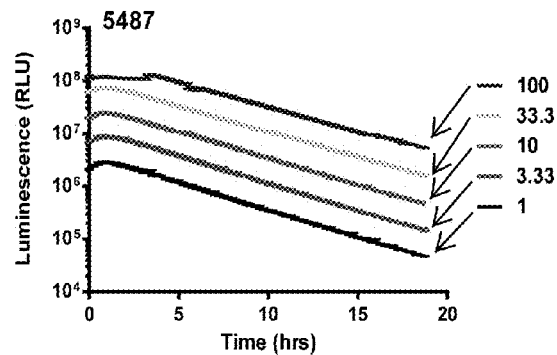
Figure 4D:
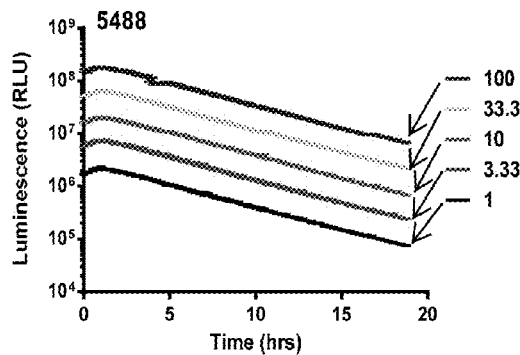

To demonstrate the ability of the disclosed compounds to act as pro-substrates, compounds PBI-5512, PBI-5455, PBI-5487 and PBI-5488 (FIG. 2) were added to cells expressing a coelenterazine-utilizing luciferase, NANOLUC®, and luminescence detected.

HeLa cells were plated into wells of a 96-well plate at 5,000 cells/well. After an overnight incubation at 37° C., 5% $CO_2$, the cells were transiently transfected with a CMV-NANOLUC® construct (pFSK/Nluc) or pGEM-3Z negative control vector using FUGENE® HD (3:1 lipid:DNA ratio; 50 ng plasmid DNA/well) and again incubated overnight at 37° C., 5% $CO_2$.

The following day, cell medium was removed and replaced with $CO_2$ independent medium plus 10% or 0.5% FBS. PBI-5512, PBI-5455, PBI-5487 or PBI-5488 were serially diluted in DMSO to give 500× stocks, followed by 250-fold dilution in $CO_2$ independent medium plus 10% or 0.5% FBS to give 2× stocks. An equivalent volume of 2× substrate stock was then added to existing volume of cells plus medium. Luminescence was measured every 15 minutes at 37° C. on a GloMax® Multi+ luminometer with 2 second integration time. The data in FIGS. 3A-3D (10% FBS) and FIGS. 4A-4D (0.5% FBS) demonstrate that each pro-substrate is capable of a sustained release of a furimazine substrate, making furimazine available for catalytic turnover by intracellular NANOLUC® throughout the time course.

Figure 5A:
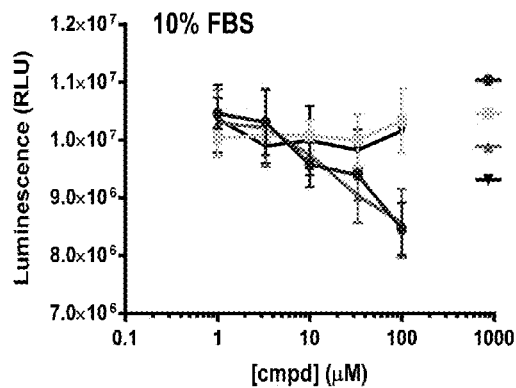
FIGS. 5A-5D depict the luminescence (FIGS. 5A and 5C) and viability of cells (FIGS. 5B and 5D) exposed to compounds PBI-5512, PBI-5455, PBI-5487 and PBI-5488. See Example 20.
Figure 5B:
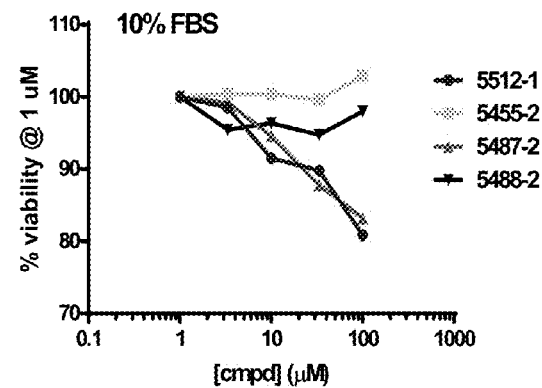
Figure 5C:
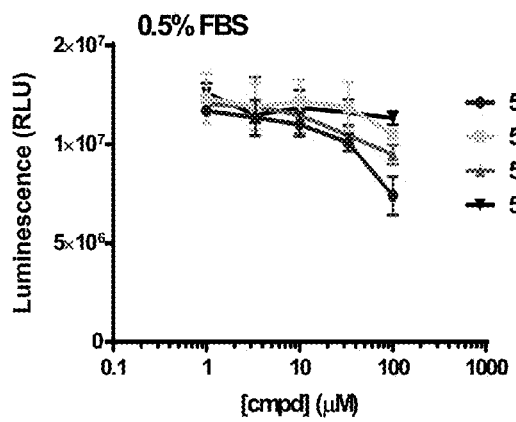
Figure 5D:
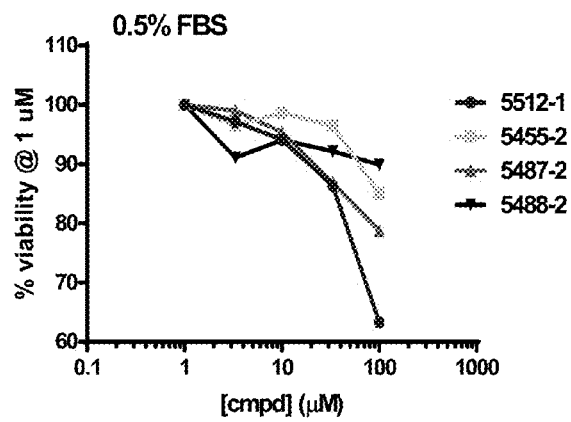

To determine cell viability, the CELLTITER-GLO® Cell Viability reagent (Promega Corporation) was used on pGEM-3Z transfected cells (control DNA lacking luciferase expression) following a modified version of the recommended protocol. Luminescence was measured using a GloMax® Multi luminometer (2 second integration time) after 2 hrs (FIGS. 5A and 5C), showing a distinct toxicity profile for each compound as a function of the concentration tested (FIGS. 5B and 5D).

Example 21

PBI-5457, PBI-5486, PBI-5487, PBI-5488 and 5489 in HeLa Cells

Figure 6:
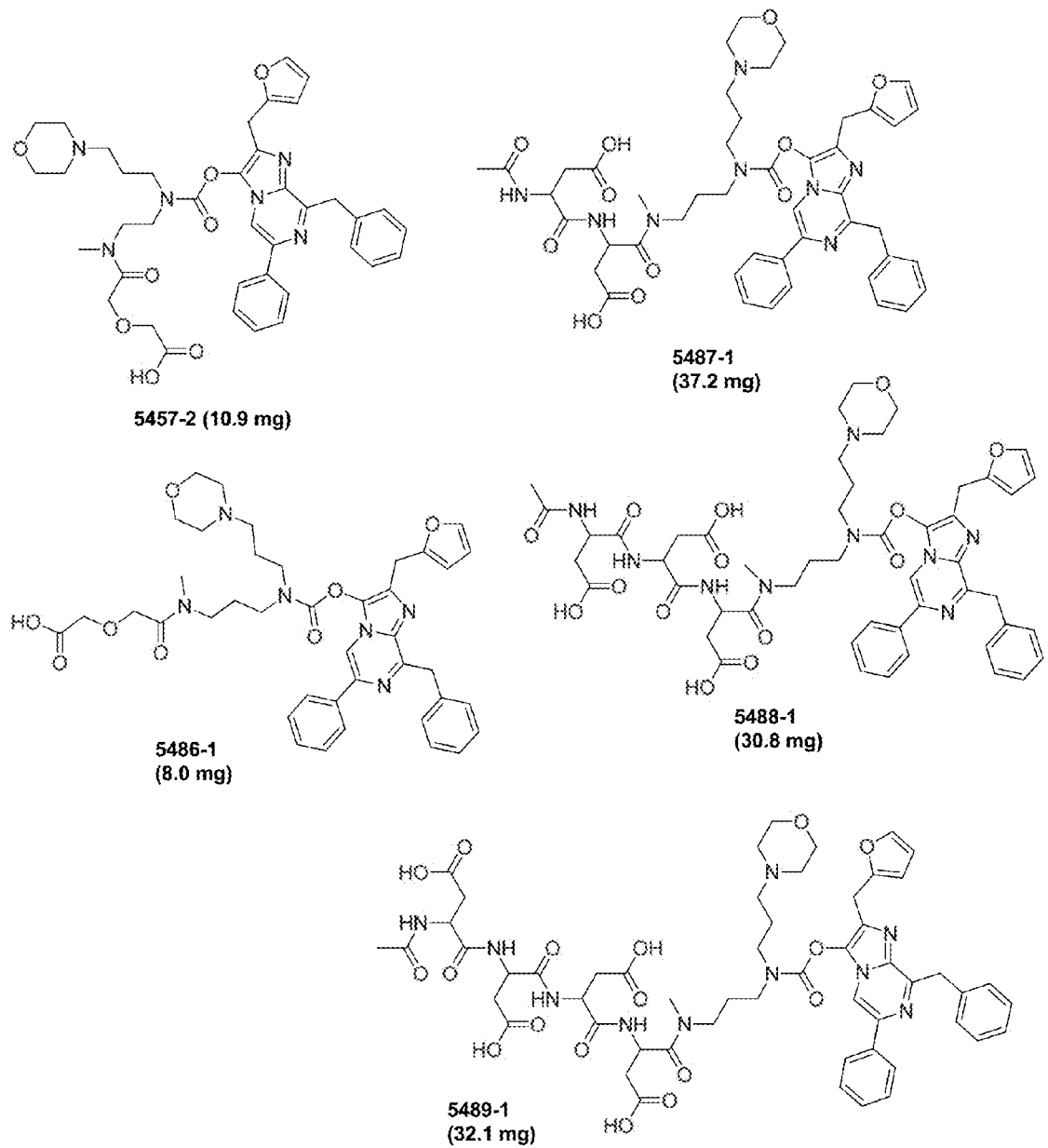
FIG. 6 depicts compounds PBI-5457, PBI-5486, PBI-5487, PBI-5488 and PBI-5489, which were added to cells expressing a coelenterazine-utilizing luciferase and luminescence was detected.
Figure 7A:
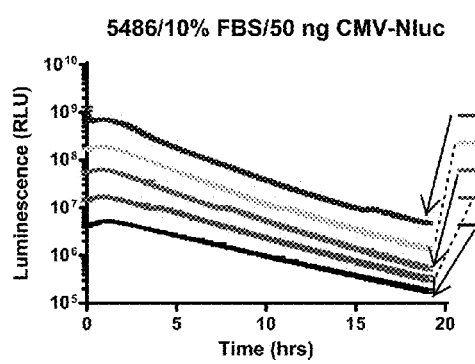
FIGS. 7A-7D depict the ability of the disclosed compounds to act as pro-substrates. Compounds PBI-5486, PBI-5487, PBI-5488, and PBI-5457 (FIG. 6) were added to cells expressing a coelenterazine-utilizing luciferase, NANOLUC®, and luminescence detected. See Example 21.
Figure 7B:
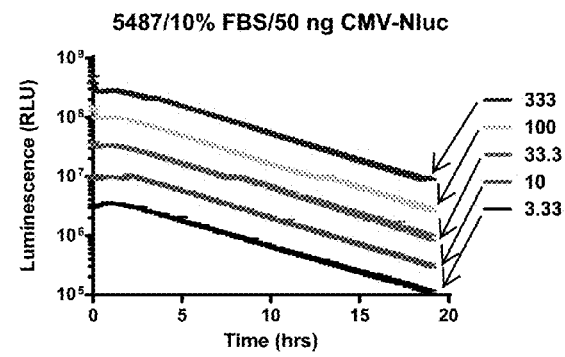
Figure 7C:
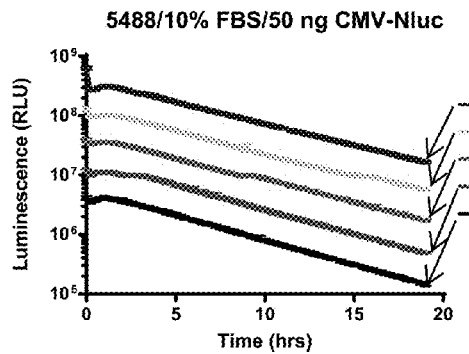
Figure 7D:
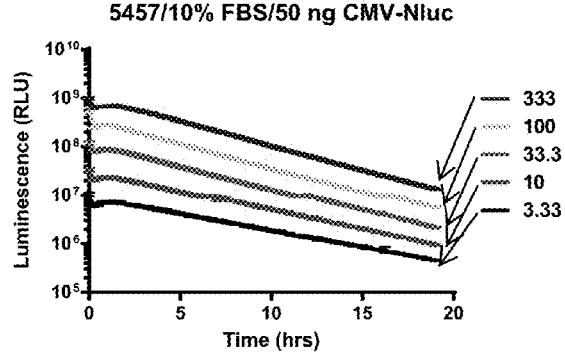
Figure 8A:
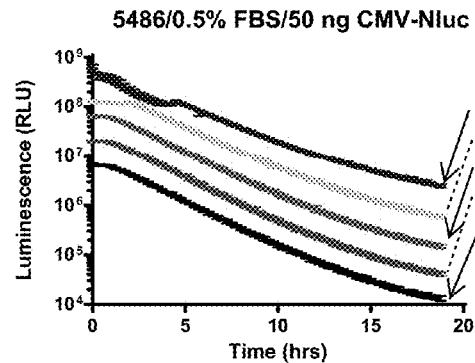
FIGS. 8A-8D depict the ability of the disclosed compounds to act as pro-substrates. Compounds PBI-5486, PBI-5487, PBI-5488, and PBI-5457 (FIG. 6) were added to cells expressing a coelenterazine-utilizing luciferase, NANOLUC®, and luminescence detected. See Example 21.
Figure 8B:
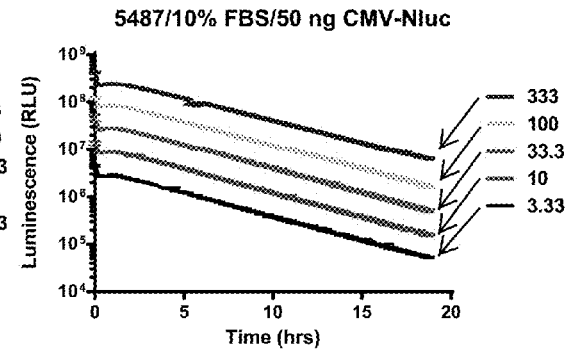
Figure 8C:
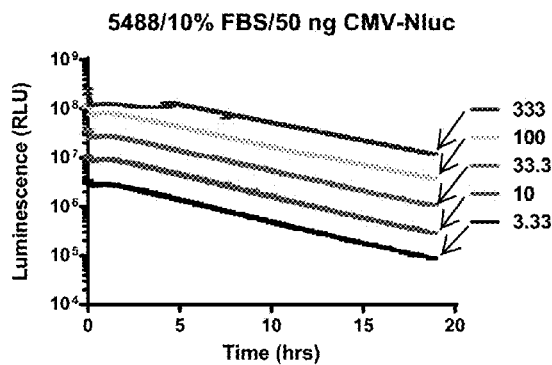
Figure 8D:
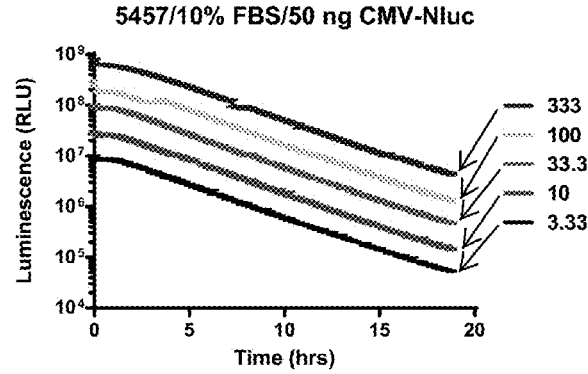

To demonstrate the ability of the disclosed compounds to act as pro-substrates, compounds PBI-5457, PBI-5486, PBI-5487, and PBI-5488 (FIG. 6) were added to cells expressing a coelenterazine-utilizing luciferase, NANOLUC®, and luminescence detected.

HeLa cells were plated into wells of a 96-well plate at 5,000 cells/well. After an overnight incubation at 37° C., 5% $CO_2$, the cells were transiently transfected with a CMV-NANOLUC® construct (pFSK/Nluc) or pGEM-3Z negative control vector using FUGENE® HD (3:1 lipid:DNA ratio; 50 ng plasmid DNA/well) and again incubated overnight at 37° C., 5% $CO_2$.

The following day, cell medium was removed and replaced with $CO_2$ independent medium plus 10% or 0.5% FBS. PBI-5457, PBI-5486, PBI-5487, PBI-5488 or 5489 were serially diluted in DMSO to give 300.3× stocks, followed by 150-fold dilution in $CO_2$ independent medium plus 10% or 0.5% FBS to give 2× stocks. An equivalent volume of 2× substrate stock was then added to existing volume of cells plus medium. Luminescence was measured every 15 minutes at 37° C. on a GloMax® Multi+ luminometer with 2 second integration time. The data in FIGS. 7A-7D (10% FBS) and FIGS. 8A-8D (0.5% FBS) demonstrate that each pro-substrate is capable of a sustained release of a furimazine substrate, making furimazine available for catalytic turnover by intracellular NANOLUC® throughout the time course.

Figure 9A:
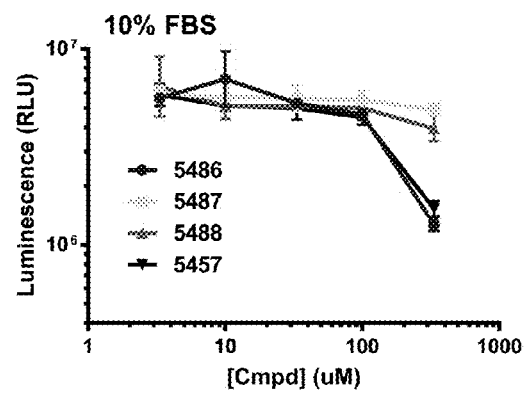
FIGS. 9A-9D depict the luminescence (FIGS. 9A and 9C) and viability of cells (FIGS. 9B and 9C) exposed to compounds PBI-5486, PBI-5487, PBI-5488, and PBI-5457. See Example 21.
Figure 9B:
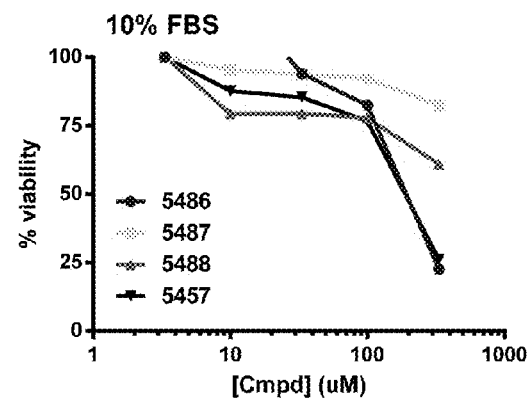
Figure 9C:
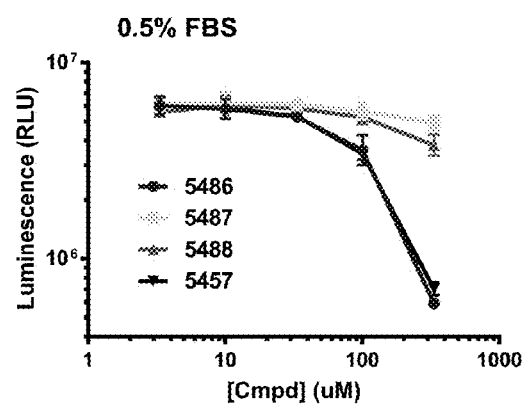
Figure 9D:
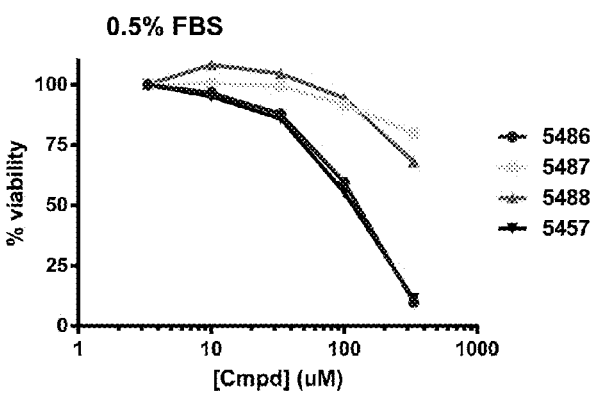

To determine cell viability, the CELLTITER-GLO® Cell Viability reagent (Promega Corporation) was used on pGEM-3Z transfected cells (control DNA lacking luciferase expression) following a modified version of the recommended protocol. Luminescence was measured using a GloMax® Multi luminometer (0.5 second integration time) after 2 hrs (FIGS. 9A and 9C), showing a distinct toxicity profile for each compound as a function of the concentration tested (FIGS. 9B and 9D).

Example 22

Figure 10:
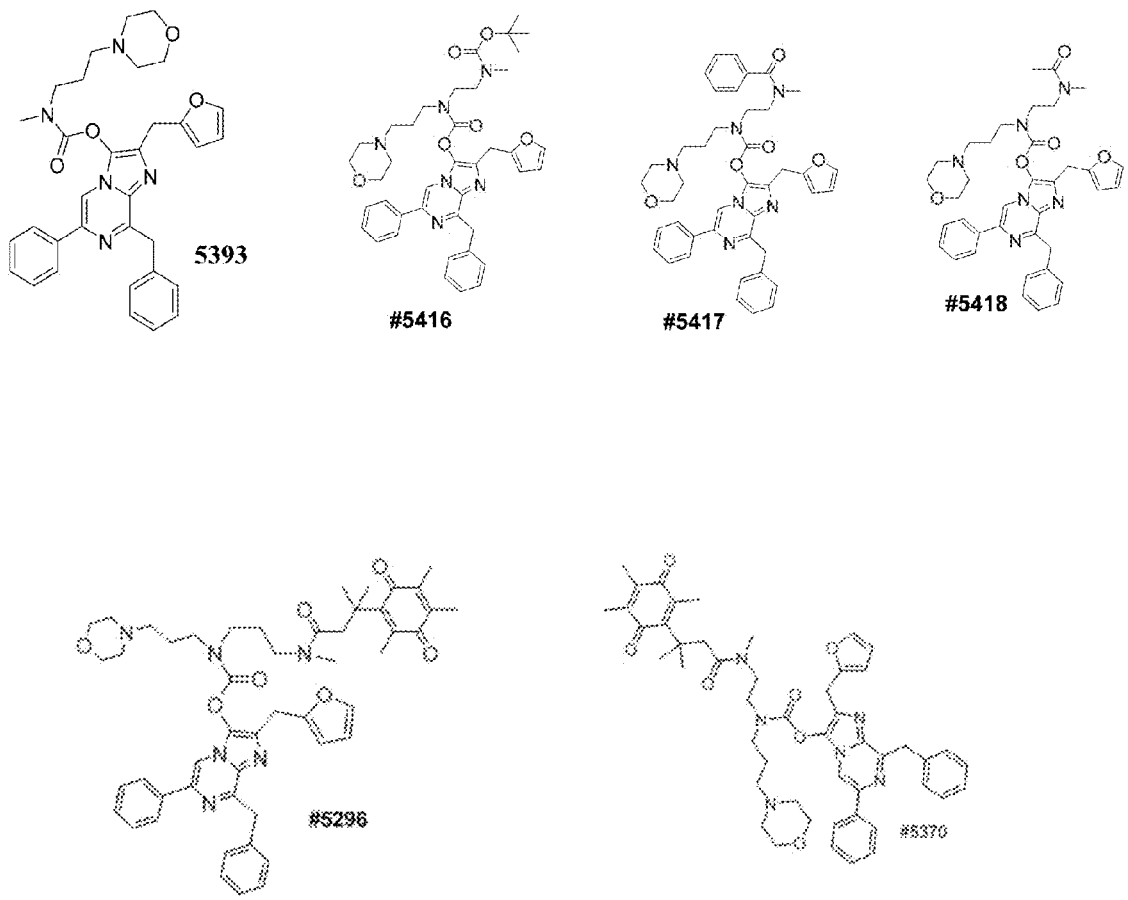
FIG. 10 depicts compounds PBI-5296, PBI-5370, PBI-5393, PBI-5416, PBI-5417 and PBI-5418, which were added to cells expressing a coelenterazine-utilizing luciferase and luminescence was detected.
Figure 11A:
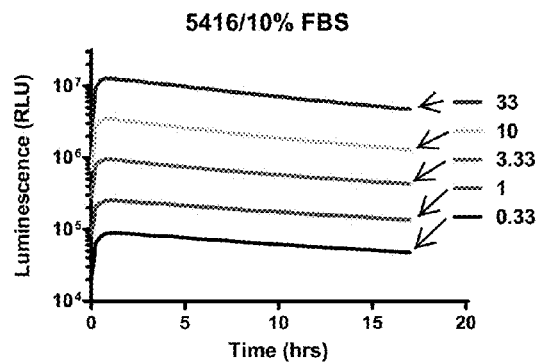
FIGS. 11A-11H depict the ability of the disclosed compounds to act as pro-substrates. Compounds PBI-5296, PBI-5370, PBI-5393, PBI-4377, PBI-5416, PBI-5417 and PBI-5418 were added to cells expressing a coelenterazine-utilizing luciferase, NANOLUC®, and luminescence detected. See Example 22.
Figure 11B:
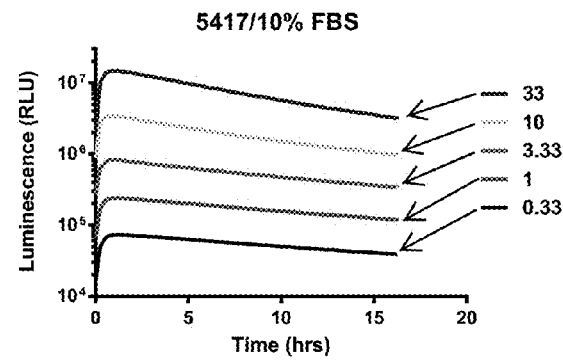
Figure 11C:
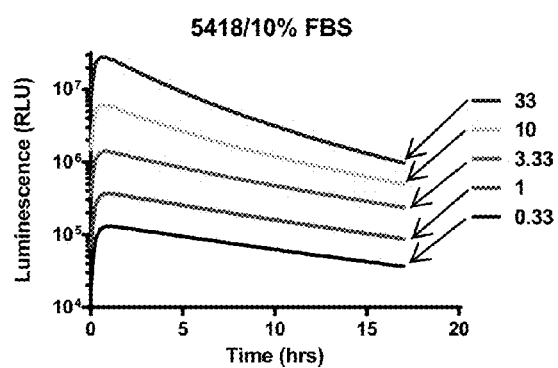
Figure 11D:
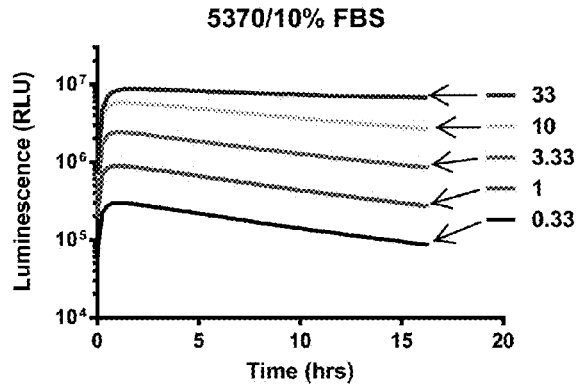
Figure 11E:
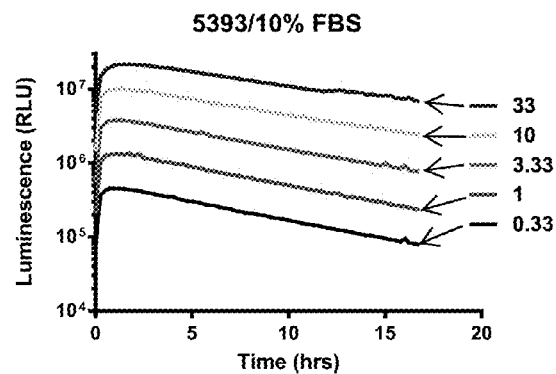
Figure 11F:
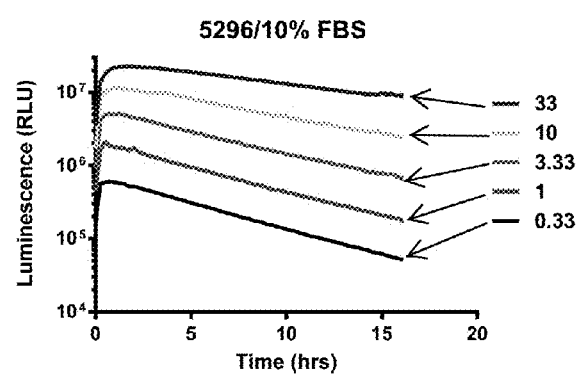
Figure 11G:
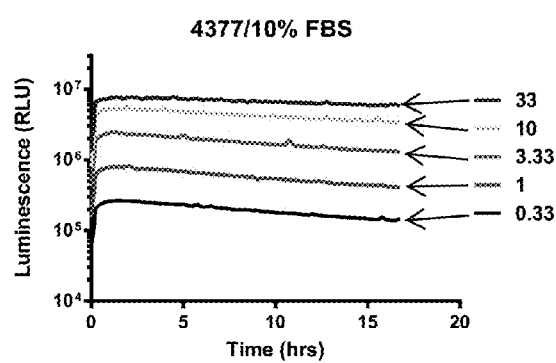
Figure 11H:
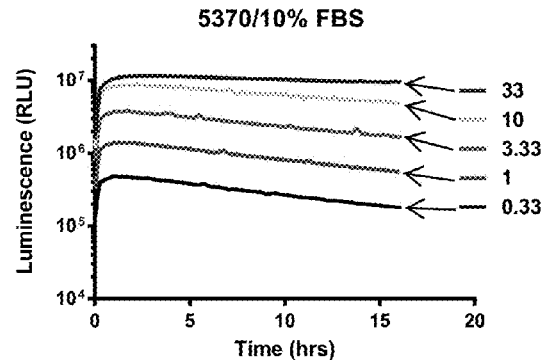
Figure 12A:
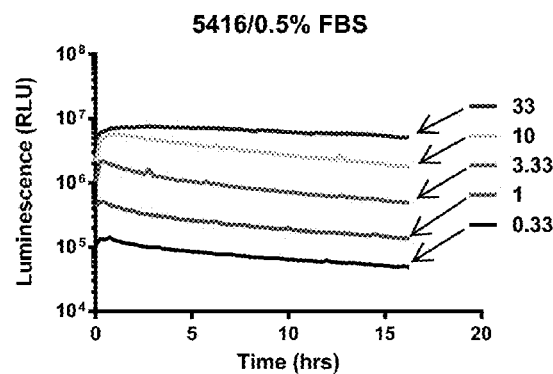
FIGS. 12A-12H depict the ability of the disclosed compounds to act as pro-substrates. Compounds PBI-5296, PBI-5370, PBI-5393, PBI-4377, PBI-5416, PBI-5417 and PBI-5418 were added to cells expressing a coelenterazine-utilizing luciferase, NANOLUC®, and luminescence detected. See Example 22.
Figure 12B:
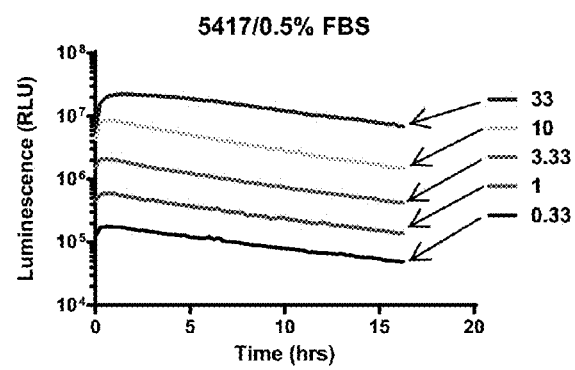
Figure 12C:
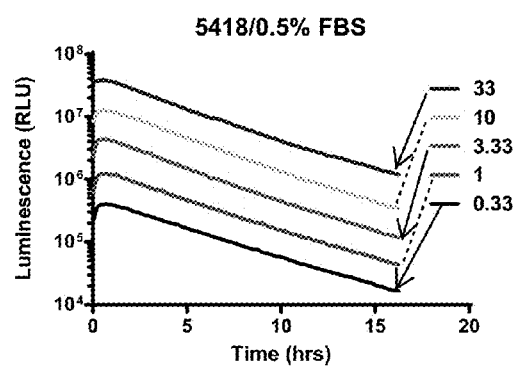
Figure 12D:
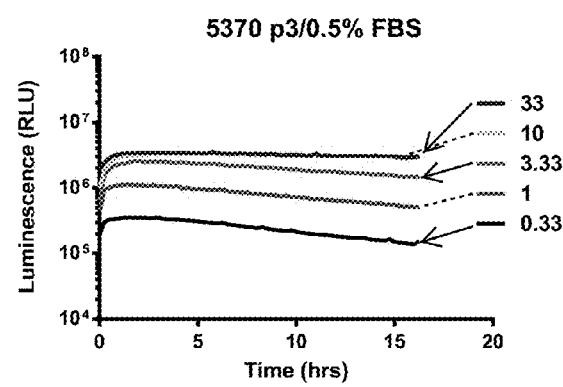
Figure 12E:
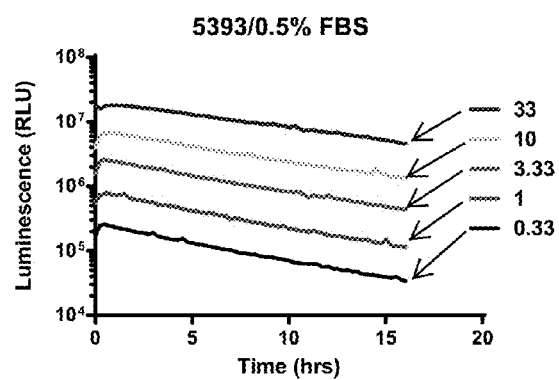
Figure 12F:
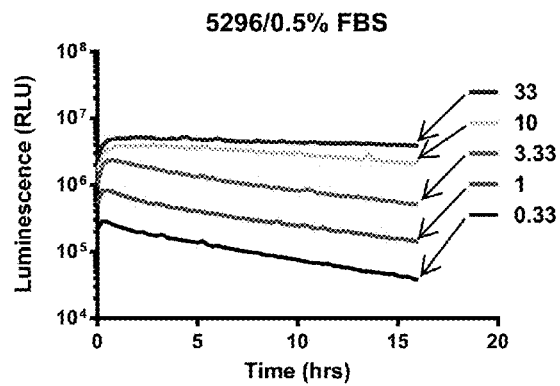
Figure 12G:
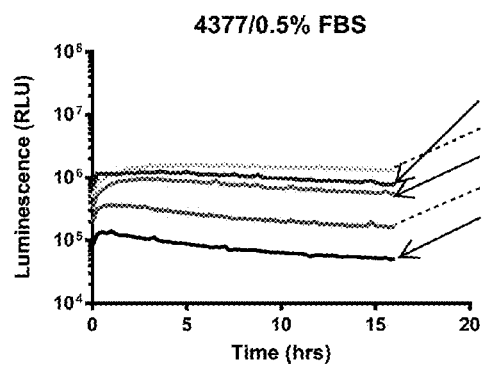
Figure 12H:
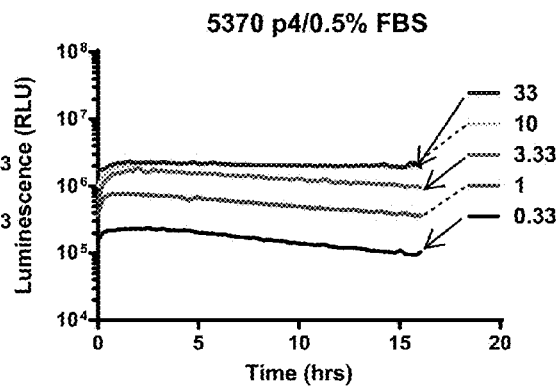

PBI-5296, PBI-5370, PBI-5393, PBI-5416, PBI-5417 and PBI-5418 in HeLa Cells To demonstrate the ability of the disclosed compounds to act as pro-substrates, compounds PBI-5296, PBI-5370, PBI-5393, PBI-5416, PBI-5417 and PBI-5418 (FIG. 10) were added to cells expressing a coelenterazine-utilizing luciferase, NANOLUC®, and luminescence detected.

HeLa cells were plated into wells of a 96-well plate at 5,000 cells/well. After an overnight incubation at 37° C., 5% $CO_2$, the cells were transiently transfected with a CMV-NANOLUC® construct (pFSK/Nluc) or pGEM-3Z negative control vector using FUGENE® HD (3:1 lipid:DNA ratio; 50 ng plasmid DNA/well) and again incubated overnight at 37° C., 5% $CO_2$.

The following day, cell medium was removed and replaced with $CO_2$ independent medium plus 10% or 0.5% FBS. PBI-5296, PBI-5370, PBI-5393, PBI-4377, PBI-5416, PBI-5417 or PBI-5418 were serially diluted in DMSO (606× stocks), followed by 303 fold dilution in $CO_2$ independent medium plus 10% or 0.5% FBS to give 2× stocks. An equivalent volume of 2× substrate stock was then added to existing volume of cells plus medium. Luminescence was measured every 15 minutes at 37° C. on a GloMax® Multi+ or Varioskan Flash luminometer with 2 second integration time. The data in FIGS. 11A-11H (10% FBS) and FIGS. 12A-12H (0.5% FBS) demonstrate that each pro-substrate is capable of a sustained release of a furimazine substrate, making furimazine available for catalytic turnover by intracellular NANOLUC® throughout the time course.

Figure 13A:
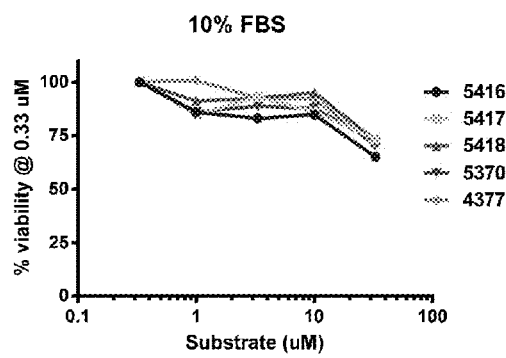
FIGS. 13A-13D depict the viability of cells exposed to compounds PBI-5416, PBI-5417, PBI-5418, PBI-5370, PBI-4377, PBI-5393, and PBI-5296. See Example 22.
Figure 13B:
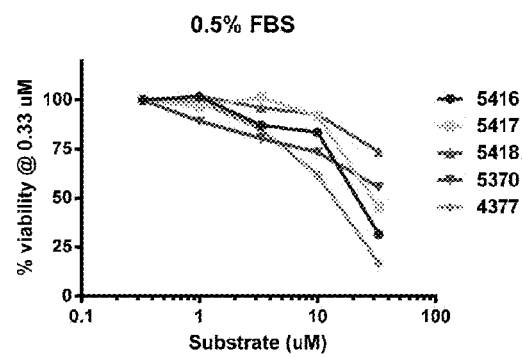
Figure 13C:
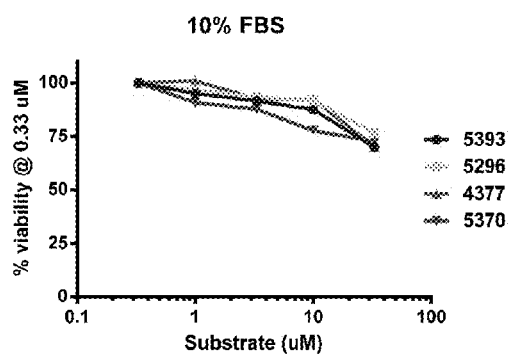
Figure 13D:
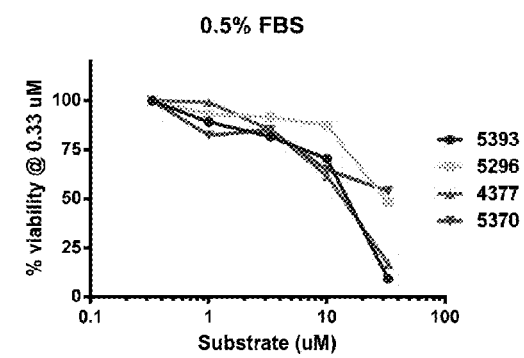

To determine cell viability of the pGEM-3Z transfected cells (control), the CELLTITER-GLO® Cell Viability reagent (Promega Corporation) was used on pGEM-3Z transfected cells (control DNA lacking luciferase expression) following a modified version of the recommended protocol. Luminescence was measured using a GloMax® Multi luminometer (0.5 second integration time) after 16.5 hours (FIGS. 13A and 13C), showing a distinct toxicity profile for each compound as a function of the concentration tested (FIGS. 13B and 13D).

Example 23

Figure 14:
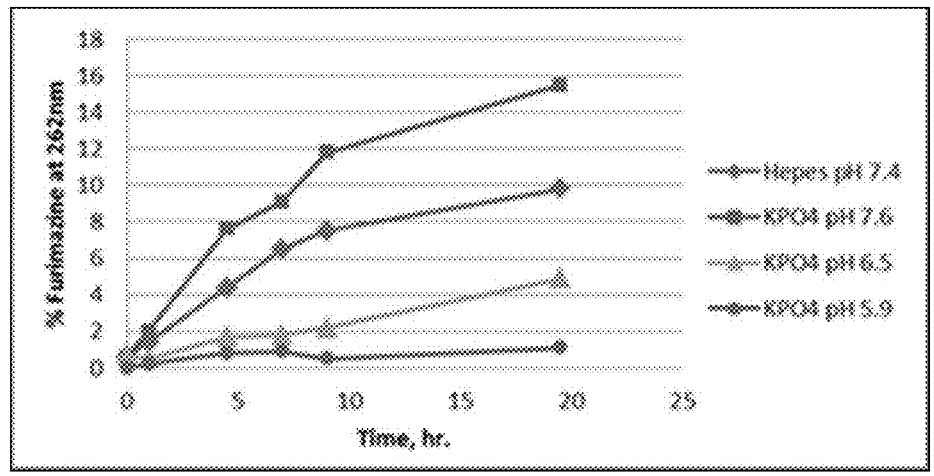
FIG. 14 depicts that the release of furimazine by hydrolysis of PBI-5455 is pH dependent.

The effect of pH on the hydrolysis of the disclosed compounds may be useful for high-throughput screening (HTS). The percent furimazine released in 1 mM of PBI-5455 solutions with different pH values ranging from 5.9 to 7.6 were detected over time using HPLC at 262 nm. FIG. 14 shows that the release of furimazine by hydrolysis of PBI-5455 is pH dependent. These compounds can be used to support HTS operation methods to enhance the initial brightness by adjusting pH or adding an appropriate nucleophile.

Example 24

As shown in Example 23, PBI-5455 is stable in slightly acidic buffer for 10 hrs. The higher the pH, the faster the release. For BRET applications to detect protein-protein and/or ligand-protein interactions, if it is a one-time point reading, the concentration in media could be higher than 100-200 µM. The pH in buffer stock could be utilized to adjust the initial brightness and make it comparable to furimazine and maintain the kinetics of furimazine. FIG. 15 shows a schematic showing an HTS operation using PBI-5455 compared to using furimazine.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

What is claimed is:
1. A compound of formula (I), or a salt thereof,

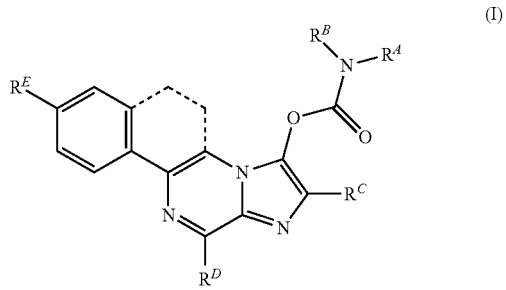

wherein,
$R^A$ is selected from the group consisting of $-(CR^1R^2)_m-N(R^3)C(O)R^4$, $-(CR^5R^6)_m-SO_3R^7$, and $-(CR^{10}R^{11})_m-CO_2R^{12}$, wherein
m at each occurrence is independently 2, 3, or 4;
$R^1$, $R^2$, $R^3$, $R^5$, $R^6$, $R^7$, $R^{10}$, $R^{11}$, and $R^{12}$ at each occurrence are independently hydrogen or $C_1$-$C_4$ alkyl;
$R^4$ is $C_1$-$C_4$ alkyl, $C_1$-$C_4$ alkoxy, carboxy-$C_1$-$C_4$ alkoxy-$C_1$-$C_4$ alkyl, phenyl optionally substituted with 1, 2, 3, 4, or 5 substituents independently selected from the group consisting of halogen, $C_1$-$C_4$ alkoxy, and $C_1$-$C_4$ haloakyl,

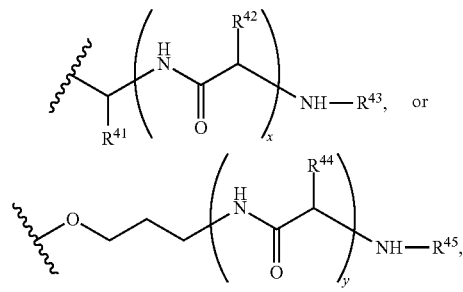

wherein
$R^{41}$, $R^{42}$, and $R^{44}$ at each occurrence are each independently carboxy-$C_1$-$C_4$ alkyl;
$R^{43}$ and $R^{45}$ are each independently selected from the group consisting of hydrogen, $-C(O)$alkyl, and

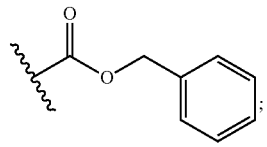 [SMILES: *C(=O)OCc1ccccc1]

x and y are each independently an integer selected from 1 to 20;
$R^B$ is $-(CR^{46}R^{47})_t-NR^{48}R^{49}$, wherein
t is 1, 2, 3, 4, 5, 6, 7, or 8
$R^{46}$ and $R^{47}$ at each occurrence are independently hydrogen or $C_1$-$C_4$ alkyl;
$R^{48}$ and $R^{49}$ at each occurrence are independently hydrogen, alkyl, haloalkyl, hydroxyalkyl, alkoxyalkyl, haloalkoxyalkyl, aminoalkyl, alkylaminoalkyl, di(alkyl)aminoalkyl, cyanoalkyl, —(CR$^{50}$R$^{51}$)$_z$—OC(O)R$^{52}$; or R$^{48}$ and R$^{49}$ together with the nitrogen atom to which they are attached form a heterocyclyl, wherein said heterocyclyl is unsubstituted or substituted with 1, 2, 3, 4, 5 or 6 substituents independently selected from the group consisting of C$_1$-C$_4$ alkyl, C$_1$-C$_4$ alkenyl, C$_1$-C$_4$ alkynyl, —NO$_2$, —CN, halogen, oxo, —OR$^{96}$, —OC(O)R$^{97}$, and —C(O)R$^{116}$, wherein R$^{50}$ and R$^{51}$ at each occurrence are independently hydrogen or C$_1$-C$_4$ alkyl;

R$^{52}$, R$^{96}$, R$^{97}$, and R$^{116}$ at each occurrence are independently hydrogen, C$_1$-C$_6$ alkyl, or aryl;

z is 1, 2, 3, or 4;

R$^C$ is —(CH)$_{0-3}$-T or C$_{1-5}$alkyl; wherein T is aryl, heteroaryl, or cycloalkyl, wherein said aryl, heteroaryl, and cycloalkyl are each independently unsubstituted or substituted with 1, 2, or 3 substituents independently selected from the group consisting of halogen, alkyl, haloalkyl, hydroxyalkyl, alkoxyalkyl, haloalkoxyalkyl, aminoalkyl, alkylaminoalkyl, di(alkylaminoalkyl), cyanoalkyl, alkoxy, haloalkoxy, cyano, hydroxy, amino, alkylamino, and di(alkyl)amino;

R$^D$ is hydrogen, C$_1$-C$_4$ alkyl, benzyl, or C$_3$-C$_6$ cycloalkyl;

R$^E$ is hydrogen, hydroxy, alkoxy, amino, alkylamino, di(alkyl)amino, —OC(O)alkyl, or —OCH$_2$OC(O)alkyl;

wherein the dash bonds together indicate the presence of an optional 6-membered ring in the compound of formula (I), wherein the optional ring is saturated or unsaturated; and wherein the optional 6-membered ring is absent.

2. The compound of claim 1, or a salt thereof, wherein R$^A$ is —(CR$^1$R$^2$)$_m$—N(R$^3$)C(O)R$^4$, wherein m, R$^1$, R$^2$, R$^3$, and R$^4$ are as defined in claim 1.

3. The compound of claim 1, or a salt thereof, wherein R$^A$ is selected from the group consisting of:

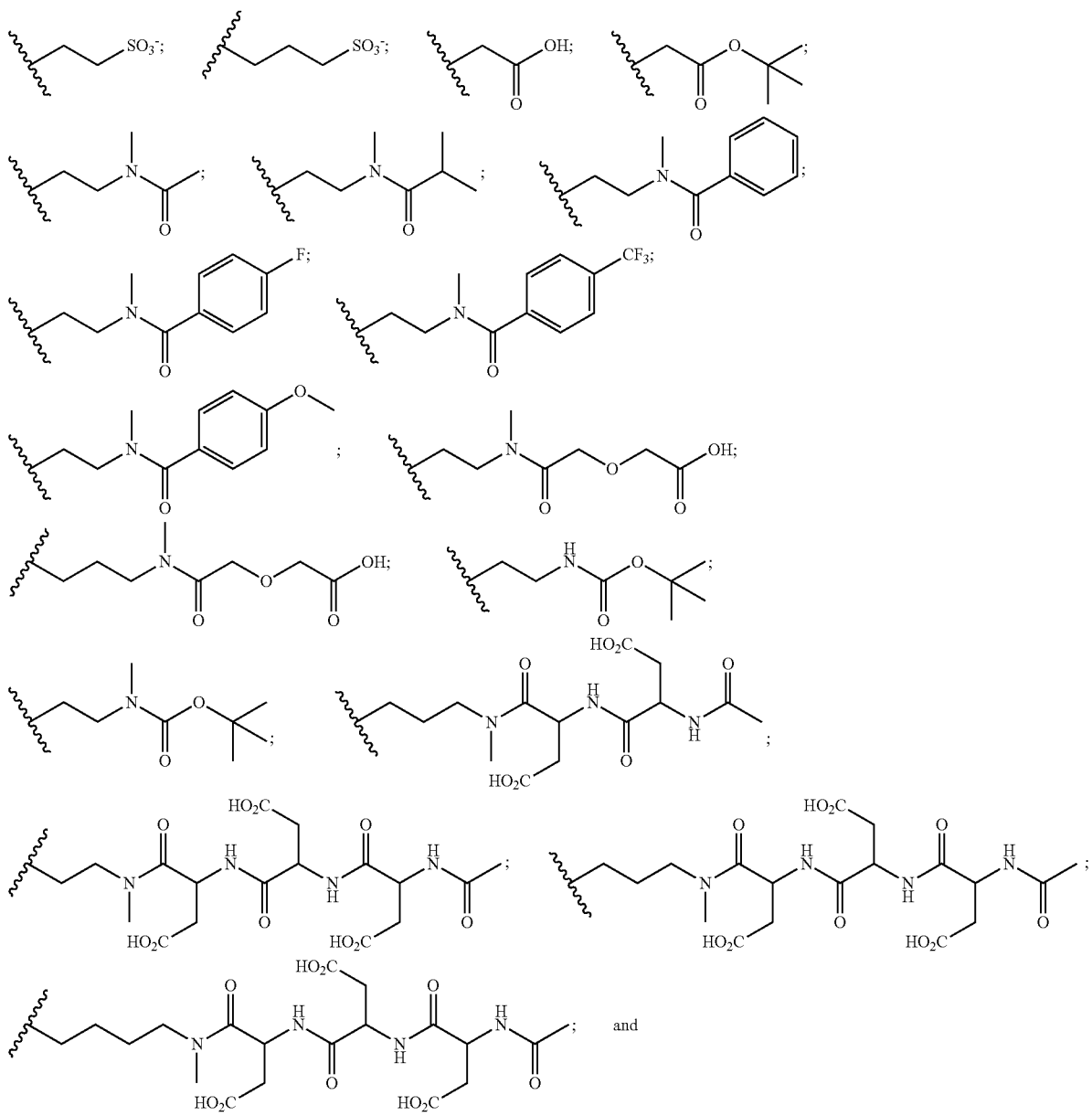

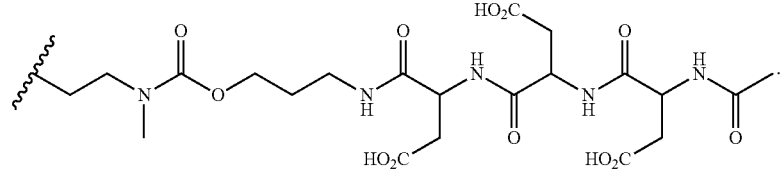

4. The compound of claim 1, or a salt thereof wherein $R^B$ is selected from the group consisting of:

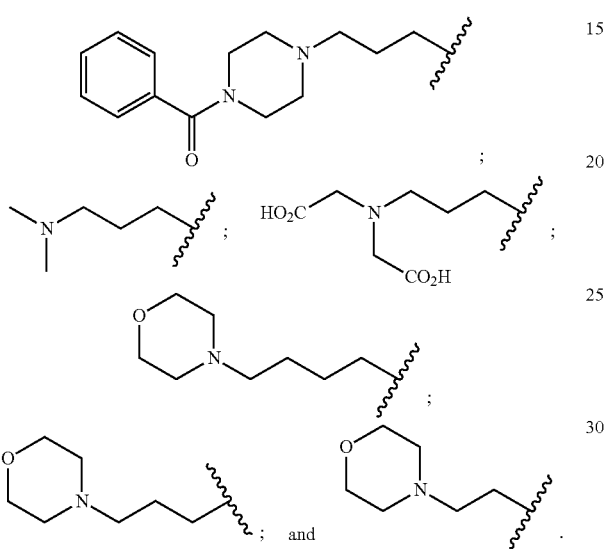

5. The compound of claim 1, or a salt thereof wherein $R^C$ is furylmethyl or benzyl, $R^D$ is benzyl, or $R^E$ is hydrogen.

6. The compound of claim 1, having formula (I-iv), or a salt thereof,

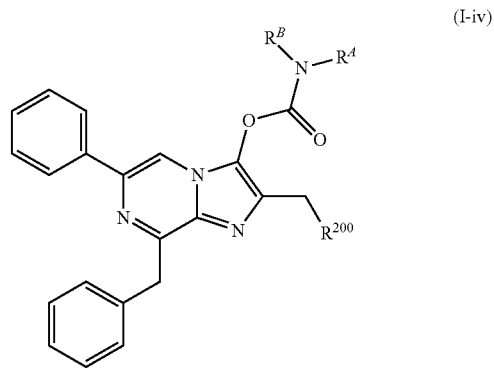

(I-iv)

wherein
$R^{200}$ is aryl or heteroaryl, each optionally substituted with 1, 2, or 3 substituents independently selected from the group consisting of halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino; and
$R^A$, and $R^B$ are as defined in claim 1.

7. The compound of claim 1, having formula (I-x), or a salt thereof,

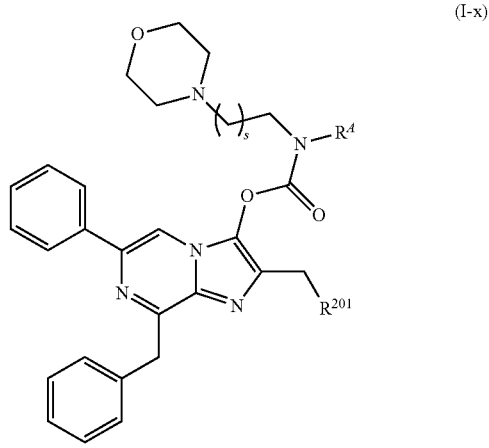

(I-x)

wherein
s is 1 or 2;
$R^{201}$ is aryl or heteroaryl, each optionally substituted with 1, 2, or 3 substituents independently selected from the group consisting of halogen, alkyl, haloalkyl, hydroxyalkyl, alkoxyalkyl, haloalkoxyalkyl, aminoalkyl, cyanoalkyl, alkoxy, haloalkoxy, cyano, hydroxy, and amino; and
$R^A$ is as defined in claim 1.

8. The compound of claim 2, having formula (I-xvii), or a salt thereof,

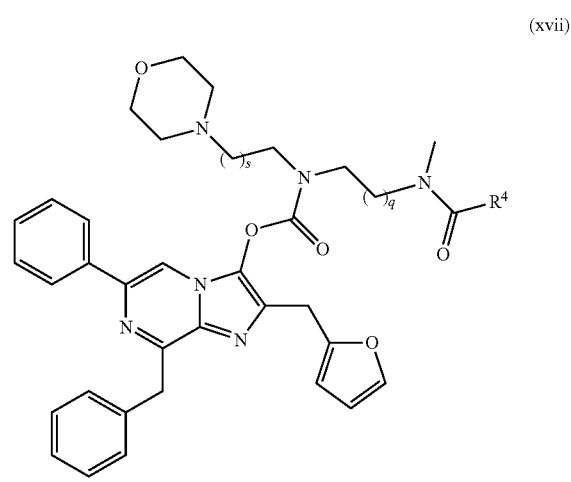

(xvii)

wherein
q is 1 or 2;
s is 1 or 2.

9. The compound of claim 1, or a salt thereof, selected from the group consisting of:

PBI-5442
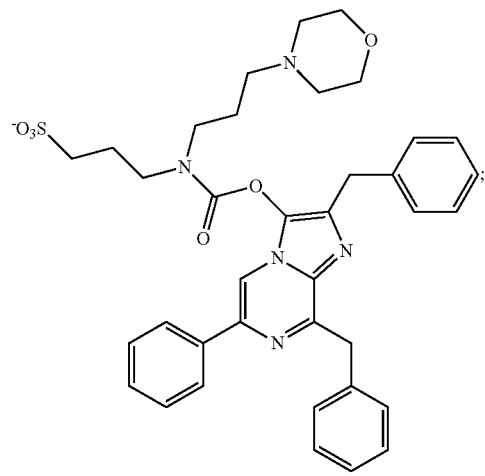
PBI-5455
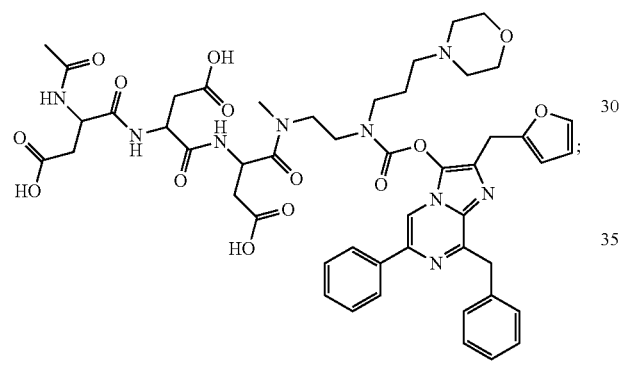
PBI-5456
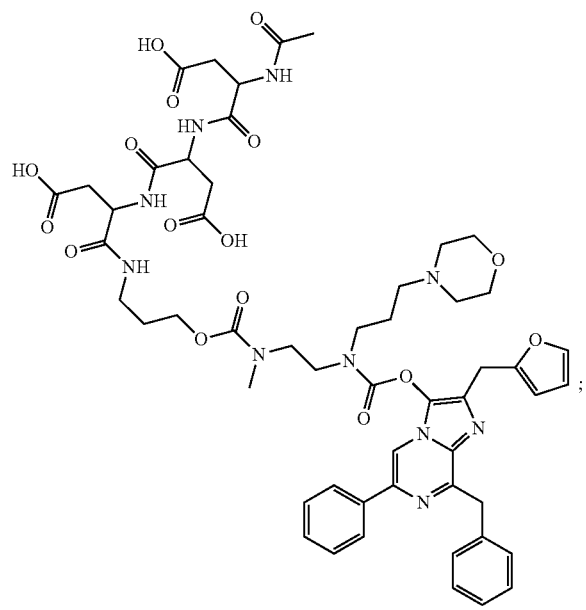
PBI-5457
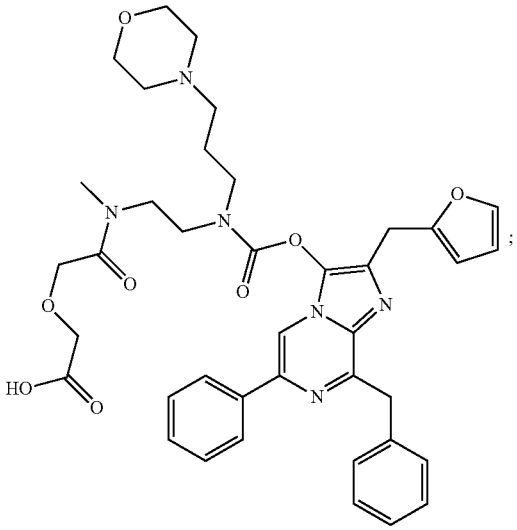
PBI-5488
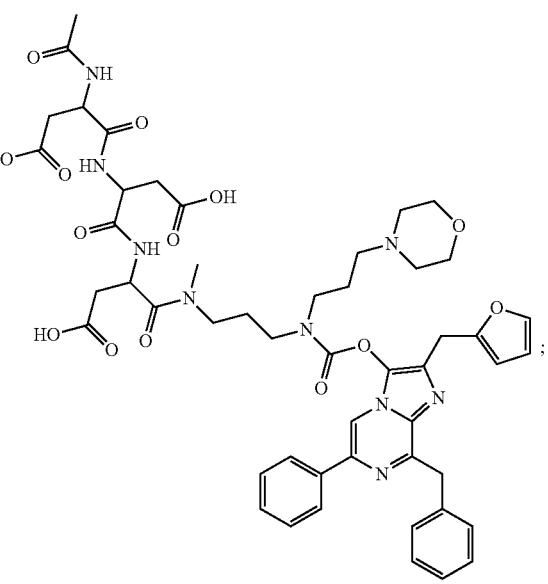

119
-continued
PBI-5489
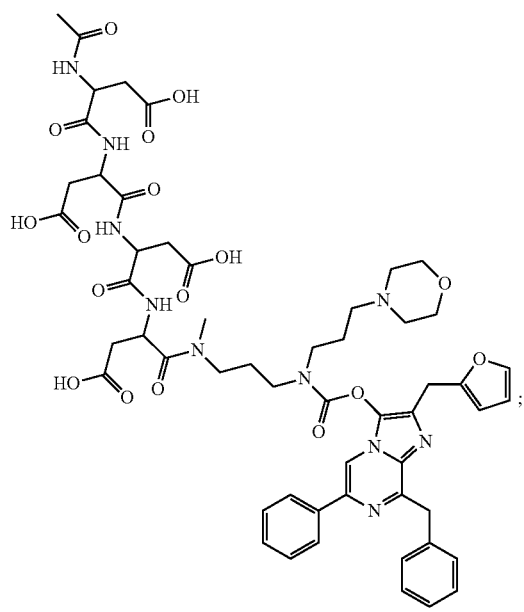
PBI-5545
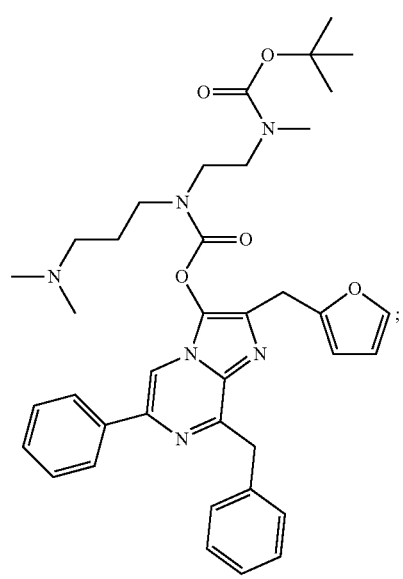
120
-continued
PBI-5416
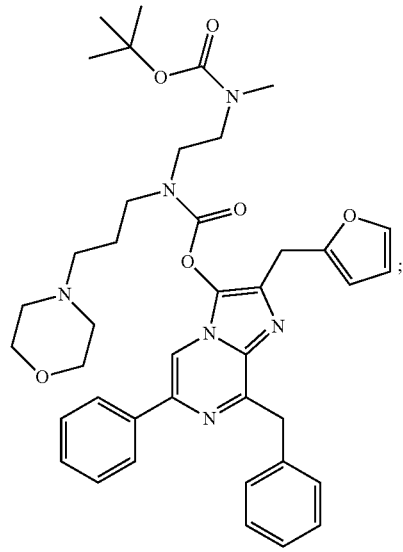
PBI-5417
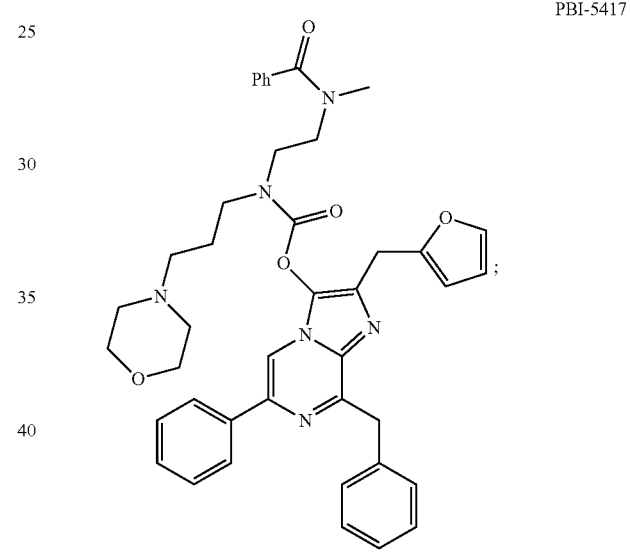
PBI-5418
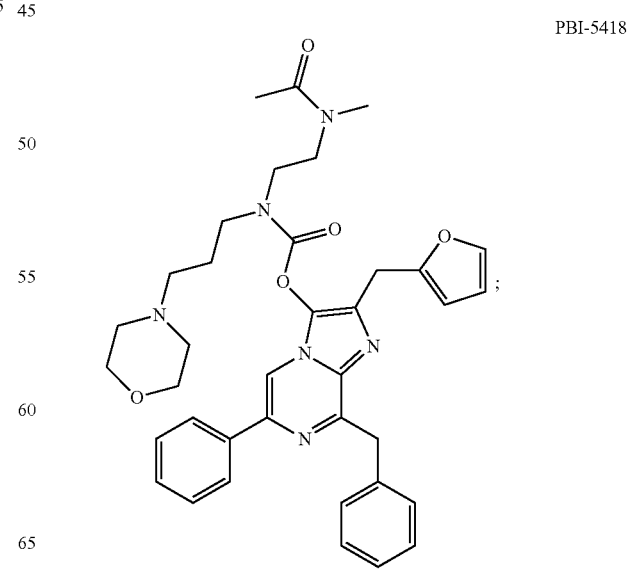

-continued
PBI-5452
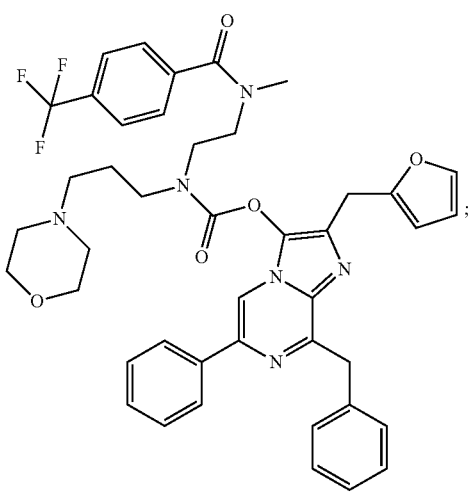
PBI-5451
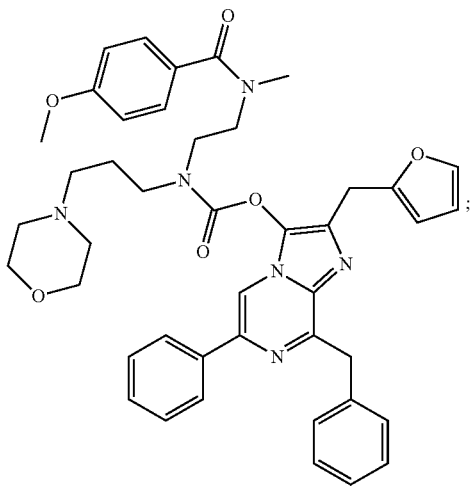
PBI-5453
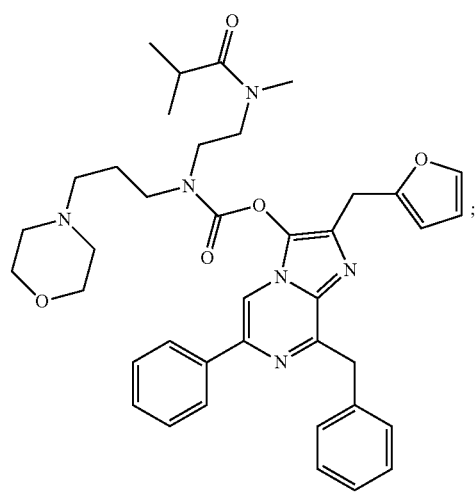
PBI-5454
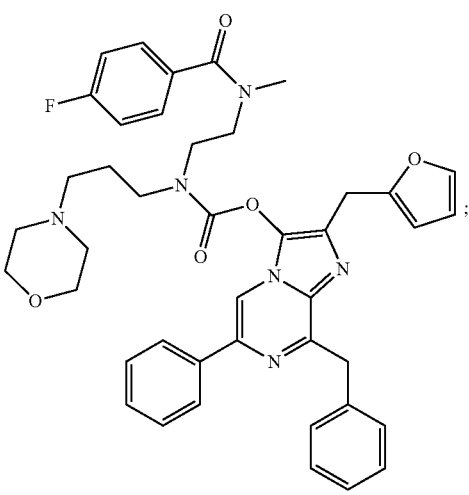
PBI-5450
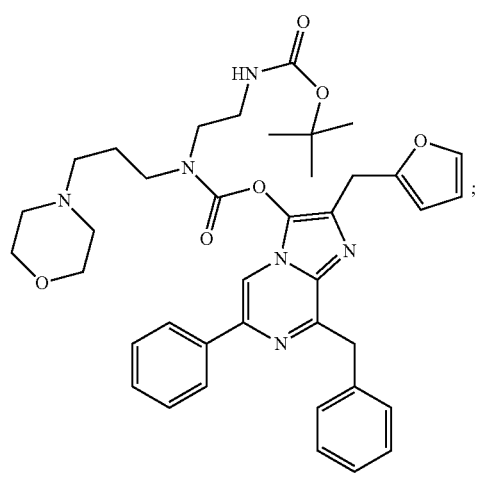
PBI-5512
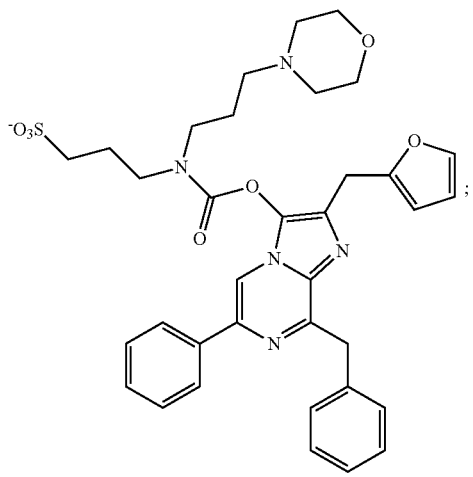

-continued

PBI-5547

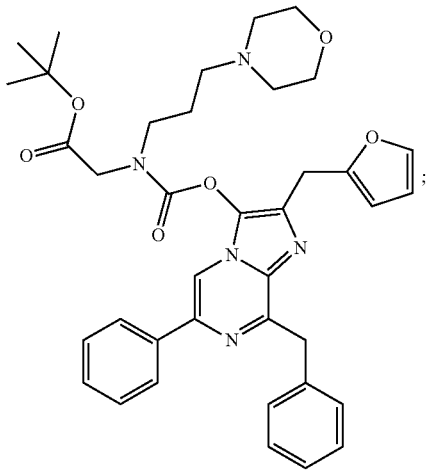

PBI-5486

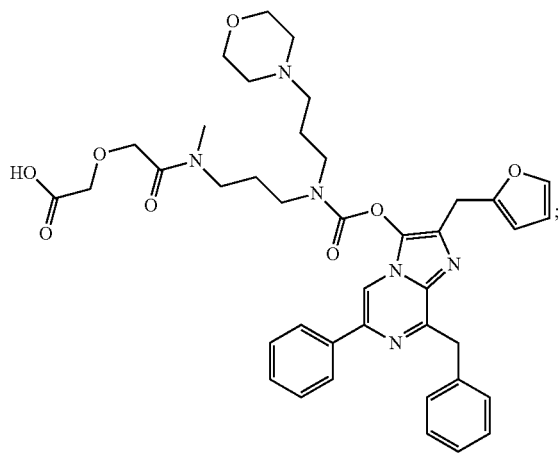

and

PBI-5487

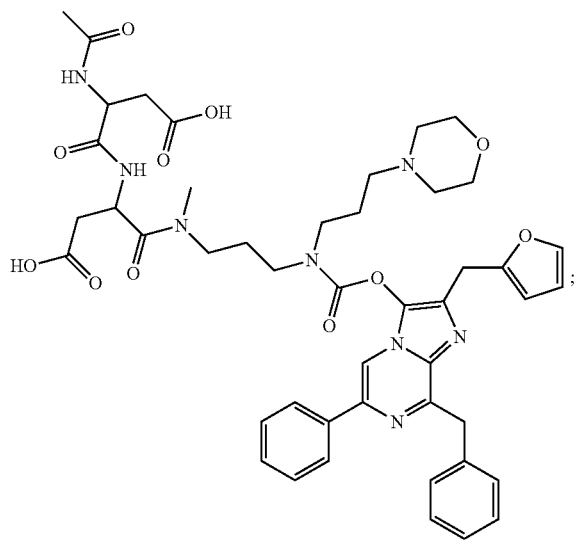

or a salt thereof.

10. The compound of claim 1, or a salt thereof, wherein $R^A$ is

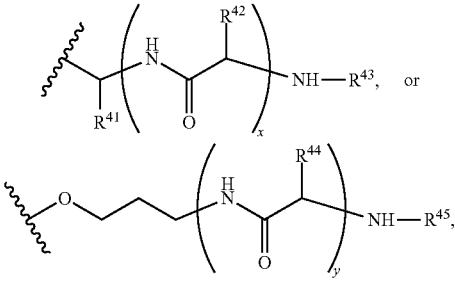

wherein $R^{41}$, $R^{42}$, $R^{43}$, $R^{44}$, $R^{45}$, x, and y are as defined in claim 1; and $R^B$ is

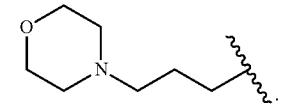 [SMILES: *CCCN1CCOCC1]

11. A composition comprising a mixture of a compound of formula (I) according to claim 1, or a salt thereof, and at least one compound of formula (II),

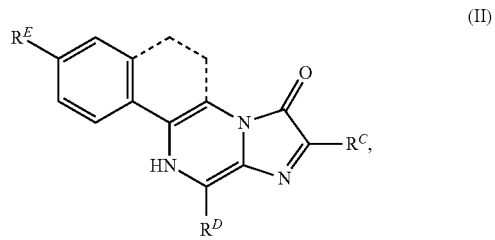

(II)

wherein $R^C$, $R^D$, and $R^E$ in formula (II) are as defined in claim 1; and wherein the dash bonds of formula (II) indicates an optional 6-membered ring, which is absent.

12. The composition according to claim 11, wherein the compound of formula (II) is selected from the group consisting of (II-i), (II-ii), (II-iii), (II-iv), and (II-v), or a combination thereof,

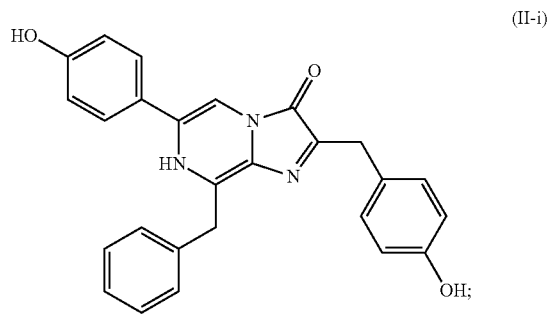

(II-i)

Coelenterazine (II-ii)

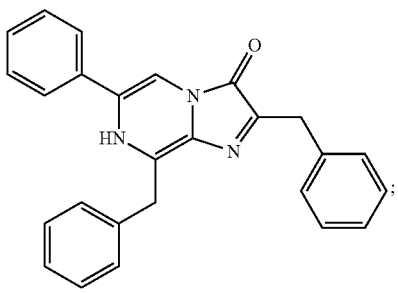

Coelenterazine-hh (II-iii)

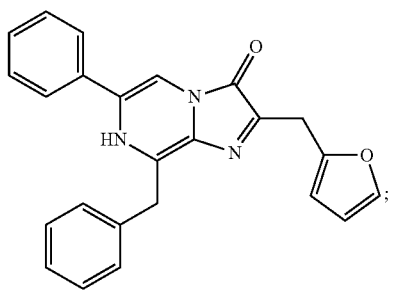

Furimazine (II-iv)

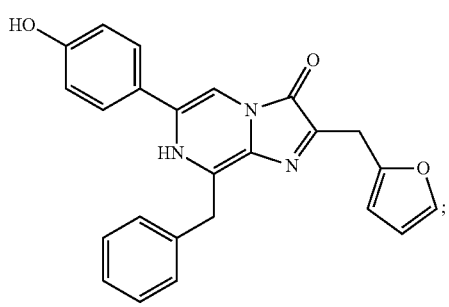

Furimazine Analog

; and (II-v)

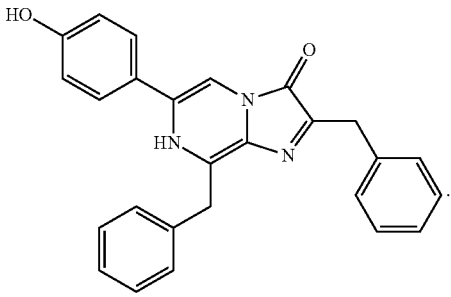

Coelenterazine-h

13. A method to detect an interaction between a first protein and a second protein in a sample, the method comprising:
   (a) contacting a sample with the compound of claim 1, or a salt thereof, wherein the sample comprises:
      (i) a first polynucleotide encoding a first fusion protein, wherein the first fusion protein comprises a first fragment of a luminescent enzyme and a first protein; and
      (ii) a second polynucleotide encoding a second fusion protein, wherein the second fusion protein comprises:
         a. a second fragment of the luminescent enzyme and a second protein; or
         b. a fluorescent acceptor molecule and a second protein; and
   (b) detecting luminescence in the sample if the second fusion protein comprises a second fragment of the luminescent enzyme and a second protein, wherein the detection of luminescence indicates an interaction between the first protein and the second protein, or detecting bioluminescence resonance energy transfer (BRET) in the sample if the second fusion protein comprises a fluorescent acceptor molecule and a second protein, indicating an interaction or close proximity of the bioluminescent donor and the fluorescence acceptor.

14. A bioluminescence resonance energy transfer (BRET) system comprising: a first fusion protein including a first target protein and a bioluminescence donor molecule, wherein the bioluminescence donor molecule is a luminescent enzyme; a second fusion protein including a second target protein and a fluorescent acceptor molecule; and the compound of claim 1, or a salt thereof.

15. A kit comprising a compound of claim 1, or a salt thereof.

* * * * *